United States Patent
Bloom et al.

(10) Patent No.: US 12,156,919 B2
(45) Date of Patent: *Dec. 3, 2024

(54) METHOD FOR DELIVERING RNA TO NEURONS TO TREAT HERPES INFECTIONS

(71) Applicants: University of Florida Research Foundation, Incorporated, Gainesville, FL (US); Board of Supervisors of Louisiana State University and Agricultural and Mechanical College, Baton Rouge, LA (US)

(72) Inventors: David C. Bloom, Gainesville, FL (US); Alfred S. Lewin, Gainesville, FL (US); Donna M. Neumann, Monona, WI (US); Zachary L. Watson, Gainesville, FL (US); Sonal Sanjeev Tuli, Gainesville, FL (US); Gregory Scott Schultz, Gainesville, FL (US)

(73) Assignees: University of Florida Research Foundation, Incorporated, Gainesville, FL (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 41 days.

This patent is subject to a terminal disclaimer.

(21) Appl. No.: 17/738,987

(22) Filed: May 6, 2022

(65) Prior Publication Data

US 2022/0380808 A1    Dec. 1, 2022

Related U.S. Application Data

(62) Division of application No. 16/312,277, filed as application No. PCT/US2017/038618 on Jun. 21, 2017, now Pat. No. 11,351,273.

(60) Provisional application No. 62/353,019, filed on Jun. 21, 2016.

(51) Int. Cl.
| | |
|---|---|
| A61K 48/00 | (2006.01) |
| A61P 31/22 | (2006.01) |
| C12N 5/0793 | (2010.01) |
| C12N 15/113 | (2010.01) |
| C12N 15/86 | (2006.01) |
| C12N 15/861 | (2006.01) |

(52) U.S. Cl.
CPC .......... *A61K 48/0091* (2013.01); *A61P 31/22* (2018.01); *C12N 5/062* (2013.01); *C12N 15/1133* (2013.01); *C12N 15/86* (2013.01); *C12N 15/861* (2013.01); *C12N 2310/121* (2013.01); *C12N 2310/20* (2017.05); *C12N 2320/32* (2013.01); *C12N 2510/00* (2013.01); *C12N 2750/14122* (2013.01); *C12N 2750/14143* (2013.01); *C12N 2750/14145* (2013.01); *C12N 2830/008* (2013.01)

(58) Field of Classification Search
None
See application file for complete search history.

(56) References Cited

U.S. PATENT DOCUMENTS

| | | |
|---|---|---|
| 11,351,273 B2 | 6/2022 | Bloom et al. |
| 2006/0116340 A1 | 6/2006 | Lewin et al. |
| 2008/0069827 A1 | 3/2008 | Fraser et al. |
| 2012/0087973 A1 | 4/2012 | Lieberman et al. |
| 2015/0231168 A1 | 8/2015 | Bloom et al. |

FOREIGN PATENT DOCUMENTS

WO    WO 2015/126927 A2    8/2015

OTHER PUBLICATIONS

International Search Report and Written Opinion for Application No. PCT/US2017/038618 mailed Sep. 28, 2017.
International Preliminary Report on Patentability for Application No. PCT/US2017/038618 mailed Jan. 3, 2019.
Bertke et al., Herpes simplex virus latency-associated transcript sequence downstream of the promoter influences type-specific reactivation and viral neurotropism. J Virol. Jun. 2007;81(12):6605-13. doi: 10.1128/JVI.02701-06. Epub Apr. 4, 2007.
Gupta et al., Anti-apoptotic function of a microRNA encoded by the HSV-1 latency-associated transcript. Nature. Jul. 6, 2006;442(7098):82-5. Epub May 31, 2006. Retraction: Nature. Jan. 31, 2008;451(7178):600. doi: 10.1038/nature06621.
Liu et al., Reduction in severity of a herpes simplex virus type 1 murine infection by treatment with a ribozyme targeting the UL20 gene RNA. J Virol. Aug. 2008;82(15):7467-74. doi: 10.1128/JVI.02720-07. Epub May 28, 2008.
Rossmiller et al., 132. Gene Therapy With Self-Complementary Recombinant Adeno-Associated Virus in Models of Autosomal Dominant Retinitis Pigmentosa Cause by RHO Mutations. Molecular Therapy. May 1, 2015;23:S54.
Tedeschi et al., Hammerhead ribozymes in therapeutic target discovery and validation. Drug Discov Today. Aug. 2009;14(15-16):776-83. doi: 10.1016/j.drudis.2009.05.003. Epub May 27, 2009.

*Primary Examiner* — Kimberly Chong
(74) *Attorney, Agent, or Firm* — Wolf, Greenfield & Sacks, P.C.

(57) ABSTRACT

Aspects of the application relate to methods and compositions for delivering therapeutic nucleic acids to neural cells or tissue in a subject. Additional aspects of the application relate to therapeutic nucleic acids, for example therapeutic ribozymes, that are useful for inhibiting viral reactivation in a subject.

14 Claims, 20 Drawing Sheets

Specification includes a Sequence Listing.

FIG. 8A

```
GAUCGCGGGUGGUGCGAAAGACUUUCCGGGCGCGUCCGGGUGCCGCGGCUCUCCGGGCCCCCCU
GCAGCCGGGGCGGCCAAGGGGCGUCGGCGACAUCCUCCCCCUAAGCGCCGGCCGGCCGCUGGUC
UGUUUUUCGUUUUCCCCGUUUCGGGGGUGGUGGGGGUGCGGUUUCUGUUUCUUUAACCCGUC
UGGGGUGUUUUUCGUUCCGUCGCCGGAAUGUUUCGUUCGUCUGUCCCCUCACGGGGCGAAGGCC
GCGUACGGCCCGGGACGAGGGGCCCCCGACCGCGGCGGUCCGGCCCCGUCCGGACCCGCUCGC
CGGCACGCGACGCGAAAAAGGCCCCCCGGAGGCUUUUCCGGGUUCCCGGCCCGGGGCCUGAGAU
GAACACUCGGGUUACCGCCAACGGCCGGCCCCCGUGGCGGCCCGGCCCGGGCCCCGGCGGAC
CCAAGGGGCCCCGGCCCGGGGCCCCACAACGGCCCGGCGCAUGCGCUGUGGUUUUUUUUCCUC
GGUGUUCUGCCGGGCUCCAUCGCCUUUCCUGUUCUCGCUUCUCCCCCCCCCCUUCUUCACCCCC
AGUACCUCCUCCCUCCCUUCCUCCCCCGUUAUCCCACUCGUCGAGGGCGCCCCGGUGUCGUUC
AACAAAGACGCCGCGUUUCCAG
```

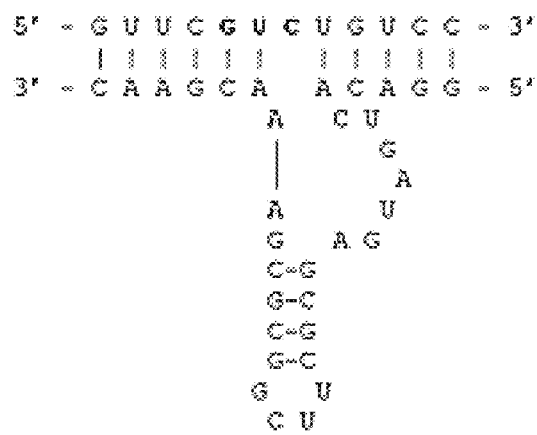

FIG. 8B

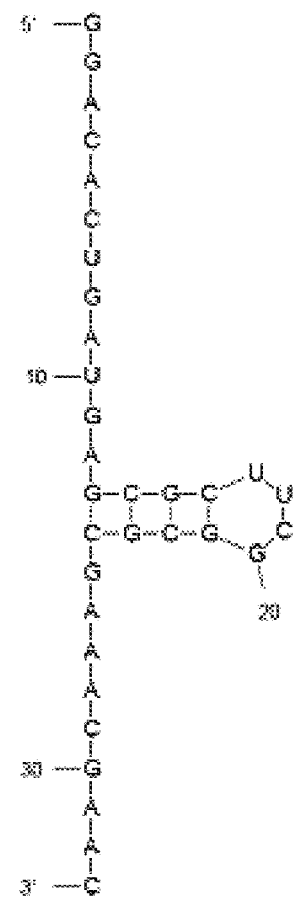

FIG. 8C

LAT intron

ICP0 gC

| Time | Acute (4dpi) | Intermediate (8dpi) | Latency (28dpi) |
|---|---|---|---|
| LAT | + | ++ | +++ |
| TAL | +++ | ++ | +/- |
| ATAL | +++ | ++ | ++ |

METHOD FOR DELIVERING RNA TO NEURONS TO TREAT HERPES INFECTIONS

RELATED APPLICATIONS

This application is a divisional of U.S. application Ser. No. 16/312,277, filed Dec. 20, 2018, which is a national stage filing under 35 U.S.C. § 371 of international application number PCT/US2017/038618, filed Jun. 21, 2017, which claims priority under 35 U.S.C. § 119(e) to U.S. Provisional Patent Application No. 62/353,019, filed Jun. 21, 2016, each of which is hereby incorporated by reference in its entirety.

FEDERALLY SPONSORED RESEARCH

This invention was made with government support under Grant No. AI048633 awarded by the Nation Institutes of Health. The government has certain rights in the invention.

REFERENCE TO A SEQUENCE LISTING SUBMITTED AS A TEXT FILE

This application contains a Sequence Listing which has been submitted in ASCII format via EFS-Web and is hereby incorporated by reference in its entirety. Said ASCII copy, created on May 2, 2022 is named U120270027US02-SEQ-EPG and is 29,532 bytes in size.

BACKGROUND

Neurological disorders and pathogenic infections of the peripheral and central nervous systems are difficult to treat, in part due to challenges in delivering therapeutic agents to the nerve cells or tissue.

SUMMARY

Disclosed herein are methods of delivering a recombinant nucleic acid to a neural cell in a subject. In some embodiments, methods comprise removing and/or disrupting epithelial cells from a tissue of a subject, and applying an agent to the tissue. In some embodiments, the agent is a nucleic acid. In some embodiments, the agent is a vector comprising a nucleic acid of interest. In some embodiments, the agent is a recombinant, non-replicative vector comprising a nucleic acid of interest.

In some embodiments, epithelial cells are removed by abrading an epithelial surface. In some embodiments, an epithelial surface can be mechanically abraded (e.g., scraping, scratching, cutting), chemically abraded (e.g., by the use of a solvent, such as acetone or ethanol), or via any other technique that can remove epithelial cells (e.g., techniques involving laser treatment, techniques involving temperature changes, for example by exposing the epithelium to freezing temperatures), or a combination of two or more different techniques. In a non-limiting example, an emery board is used to abrade the epithelial cells and expose nerve termini (e.g., in the underlying dermis). The epithelial surface can be located on any tissue of the subject. Non-limiting examples include an epithelial surface of the cornea, soft tissues of the eye, lip, mouth, nose, hand, arm, vagina, rectum, or foot of the subject.

In some aspects, the vector is an AAV vector. In some embodiments, the AAV vector is a recombinant AAV (rAAV), a single-stranded AAV (ssAAV), a self-complementary AAV (scAAV), a wildtype AAV, or an AAV (e.g., an rAAV) having a modified capsid.

In some embodiments, the neural cell is a sensory neuron. In some embodiments, the sensory neuron is a dorsal root ganglion neuron. In some embodiments, the neural cell is in the peripheral nervous system. In some embodiments, the neural cell is in the central nervous system.

In some embodiments, a vector comprises a nucleic acid encoding a ribozyme. In some embodiments, the ribozyme specifically binds and/or cleaves a latency-associated region transcript (e.g., a latency-associated RNA transcript (LAT), a TAL transcript, an ATAL transcript, or any combination of two or more thereof). In some embodiments, the ribozyme specifically binds and/or cleaves a latency-associated RNA transcript (LAT). In some embodiments, the ribozyme specifically binds and/or cleaves a TAL transcript. In some embodiments, the ribozyme specifically binds and/or cleaves an ATAL transcript. In some embodiments, the ribozyme has a nucleic acid sequence of SEQ ID NO. 14. In some embodiments, the ribozyme has a nucleic acid sequence selected from Table I. In some embodiments, the ribozyme has a nucleic acid sequence selected from Table IV.

Also disclosed herein are isolated nucleic acids that specifically bind and/or cleave a latency-associated region transcript (e.g., a LAT transcript, a TAL transcript, an ATAL transcript, or any combination of two or more thereof) of a virus (e.g., a herpes virus). In some embodiments, the latency-associated region transcript comprises one or more of a LAT transcript, a TAL transcript, or an ATAL transcript. In some embodiments, the isolated nucleic acids comprise a sequence selected from SEQ ID NO. 14, Table I, or Table IV. In some embodiments, the nucleic acids are RNA molecules. In some embodiments, the RNA is a ribozyme. In some embodiments, the ribozyme comprises SEQ ID NO. 14. In some embodiments, the ribozyme comprises a sequence selected from Table I. In some embodiments, the ribozyme comprises a sequence selected from Table IV.

In some aspects, methods and compositions are provided to target a nucleic acid (e.g., a gene or RNA transcript, such as a LAT transcript, a TAL transcript, an ATAL transcript, or other transcript, or any combination of two or more thereof) of a microorganism (e.g., of a bacterium or a virus). Non-limiting examples of viruses include herpes simplex virus-1 (HHV-1), herpes simplex virus-2 (HHV-2), Varicella zoster virus (HHV-3), Epstein-Barr virus (HHV-4), Cytomegalovirus (HHV-5), Roseolovirus (HHV-6), HHV-7, and Kaposi's sarcoma-associated herpesvirus (HHV-8). In some embodiments, the virus is a herpes virus.

Also disclosed herein are methods of treating a neurotropic virus, comprising delivering a viral vector that comprises a nucleic acid encoding a molecule that specifically binds and/or cleaves a latency-associated region transcript of a virus (e.g., a LAT transcript, a TAL transcript, an ATAL transcript, or other transcript, or any combination of two or more thereof). In some embodiments, the nucleic acid encodes a ribozyme. In some embodiments, the nucleic acid encodes an interfering RNA. In some embodiments, the latency-associated region transcript comprises one or more of a LAT transcript, a TAL transcript, or an ATAL transcript. In some aspects of the invention, the neurotropic virus is herpes virus. Non limiting-examples of neurotropic viruses that can be treated include herpes simplex virus-1 (HHV-1), herpes simplex virus-2 (HHV-2), Varicella zoster virus (HHV-3), Epstein-Barr virus (HHV-4), Cytomegalovirus (HHV-5), Roseolovirus (HHV-6), HHV-7, and Kaposi's sarcoma-associated herpesvirus (HHV-8). Accordingly, in some embodiments, the nucleic acid encodes a molecule (e.g., an RNA) that specifically binds and/or cleaves an RNA transcript that is orthologous to a transcript described herein (e.g., a LAT transcript, a TAL transcript, an ATAL transcript, or other transcript, or any combination of two or more thereof). Also provided herein are methods of treating a herpes virus infection comprising administering a nucleic acid that specifically cleaves the latency associated RNA transcript (LAT) of a virus (e.g., a LAT transcript, a TAL transcript, an ATAL transcript, or other transcript, or any combination of two or more thereof), thereby preventing, reducing or delaying the recurrence of pathologies associated with the reactivation of latent virus.

In some embodiments, methods and compositions can be used to deliver detectable molecules to neural cells (e.g., for diagnostic or imaging purposes). In some embodiments, a gene encoding a detectable marker (e.g., a detectable protein, for example a fluorescent or bioluminescent protein) can be delivered to neural cells or tissue using a recombinant virus (e.g., an rAAV) as described in this application.

These and other aspects are described in more detail herein.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIGS. 2A-2B show mice infected with ssAAV-GFP only. DRG were harvested 14 days post-inoculation (dpi). Tissue sections were incubated with anti-GFP primary antibody (FIG. 2A) or no primary antibody (FIG. 2B). Primary antibody was detected by FITC-labeled secondary antibody. FIGS. 2C-2D show mice infected with KOS/62 only. DRG were harvested 4 dpi. Tissue sections were incubated with anti-β-gal primary antibody (FIG. 2C) or no primary antibody (FIG. 2D). Primary antibody was detected by Texas Red-labeled secondary antibody.

FIG. 3A depicts a green channel image: anti-GFP primary antibody was detected by FITC-labeled secondary antibody. Green cells have been transduced by AAV. FIG. 3B shows a red channel image: anti-β-gal primary antibody was detected by Texas Red-labeled secondary antibody. Red cells have been infected by HSV-1. FIG. 3C is a merged image of the red and green images. Yellow indicates co-localization of GFP and β-gal expression from cells co-infected with both AAV and HSV-1.

FIG. 4A shows primary antibody incubation performed using mouse anti-GFP (Abcam), followed by incubation with a biotinylated HRP secondary (Vector Labs). FIG. 4B shows a control slide was prepared from the TG of naïve rabbit without AAV treatment, subjected to both primary and secondary antibody incubation.

FIGS. 8A-8C show the design of a synthetic hammerhead ribozyme targeting the LAT 5' exon. The 5' exon of the HSV-1 LAT shown in FIG. 8A was analyzed for hammerhead cleavage sequences. The selected GUC triplet is boxed. The sequence corresponds to SEQ ID NO: 12. FIG. 8B shows antisense flanking regions designed around the conserved catalytic domain to hybridize with the region surrounding the selected triplet. The sequences, from top to bottom, correspond to SEQ ID NOs: 13 and 14. FIG. 8C shows MFOLD predicted base pairing in stem II, but not in the flanking regions. The sequence corresponds to SEQ ID NO: 14.

DETAILED DESCRIPTION

Figure 1:
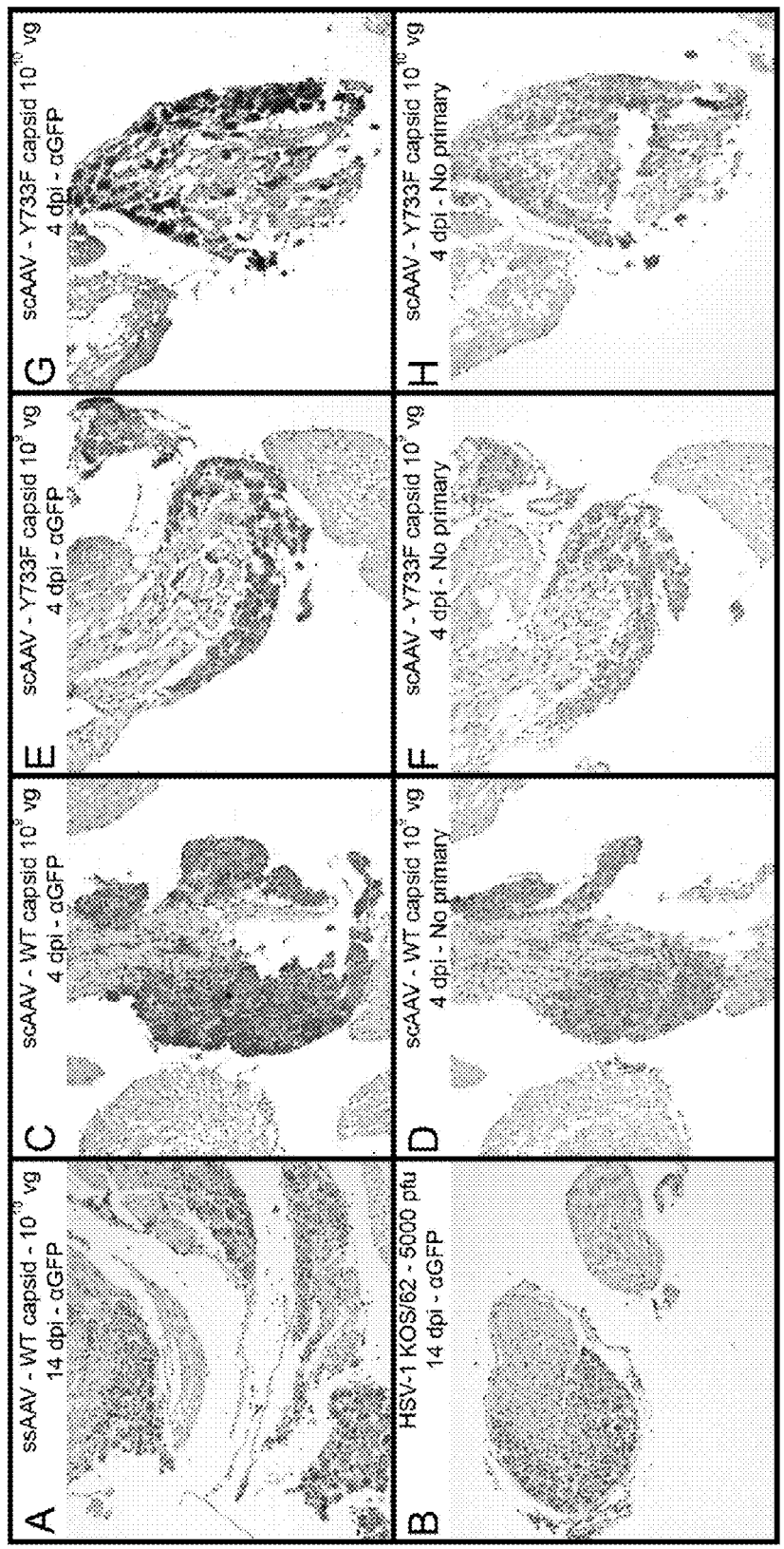
FIG. 1 shows that, following footpad inoculation, rAAV8 vectors transduce nearly 100% of sensory neurons in mouse DRG. Vectors with modified capsids are at least 10-fold more efficient than wild-type. The immunohistochemistry of infected mouse DRG is shown. Mice were infected with rAAV or KOS/62 at the given dose and tissues were harvested as shown. Anti-GFP primary antibody was incubated with sections A, B, C, E, and G to detect the presence of GFP. No primary antibody was incubated with sections D, F, and H. All sections were stained by HRP enzymatic cleavage of DAB substrate (brown) for 8 minutes. Hematoxylin (blue) was used as a counterstain.

Aspects of the application relate to compositions and methods for delivering a nucleic acid to neural cells or neural tissue in a subject. In some embodiments, compositions and methods described in this application are useful to provide a therapeutic nucleic acid to neural cells or neural tissue in a subject. In some embodiments, a therapeutic nucleic acid targets a gene or other nucleic acid of a pathogen (e.g., a virus) that infects neural cells or neural tissue in a subject. In some embodiments, a therapeutic nucleic acid targets a disease-associated nucleic acid in neural cells or neural tissue in a subject. In some embodiments, the disease-associated nucleic acid is a viral specific gene. In some embodiments, the disease-associated nucleic acid is a subject specific gene. In some embodiments, a therapeutic nucleic acid is a ribozyme or interfering RNA that degrades and/or inactivates the targeted nucleic acid (e.g., siRNA, shRNA, microRNA, antisense RNA). In some embodiments, the therapeutic nucleic acid is useful to treat a viral infection (e.g., a herpes infection) in a subject.

In some embodiments, a nucleic acid (e.g., a therapeutic nucleic acid) is encoded by a recombinant viral vector. In some embodiments, the recombinant viral vector is viral particle comprising a recombinant viral genome encapsidated in a viral particle (e.g., comprising viral capsid proteins). The recombinant viral vector can be a recombinant adeno-associated viral vector (rAAV vector). However, other viral vectors can be used. In some embodiments, the recombinant viral vector is replication deficient. In some embodiments, the capsid proteins include one or more amino acid substitutions relative to their wild-type sequence.

In some embodiments, a nucleic acid (e.g., RNA) and/or a recombinant viral vector that encodes the nucleic acid, is delivered to neural cells or neural tissue in a subject by contacting the recombinant viral vector to an exposed tissue surface (e.g., after treatment to remove epithelial cells) of the subject.

The exposed tissue surface can be any suitable tissue. Non-limiting examples of suitable tissue types include skin, soft tissues of the eye, cornea, mucosal tissue, nervous tissue, muscle tissue, and adipose tissue.

In some embodiments, the tissue can be exposed by treating the surface of the tissue to remove and/or disturb epithelial cells, and/or scratch the underlying epidermis. Removing and/or disturbing epithelial cells, and/or scratching the underlying epidermis, exposes the nerve termini and/or allows for or enhances exposure of the vector to the nerve termini. In some embodiments treating the surface of the tissue includes removing and/or disturbing cornified (e.g., keratinized or dead) epithelial cells. In some embodiments, a tissue surface is treated by physical abrasion, chemical treatment, or a combination thereof. In some embodiments, physical abrasion comprises abrasion with an abrasive material (e.g., emery board or sandpaper).

In some embodiments, the surface of the tissue is treated to facilitate uptake of the vector. In some embodiments, the surface of the tissue is injected intradermally with a saline solution. In some embodiments, the saline induces an inflammatory process or sensitizes the nerve termini to promote vector uptake. In some embodiments, the saline treatment dramatically improves uptake of the vector. In one embodiment, the surface of the tissue is injected intradermally with 0.05 mL of sterile 10% saline solution. In some embodiments, the epithelial surface is stroked to remove the cornified cells 30 minutes, 1 hour, 2 hours, 3, hours, or longer after pre-treatment of the surface of the tissue with a saline solution.

Other non-limiting methods of treatment of the surface of the tissue to facilitate vector uptake include application of a solvent (for example an organic solvent, e.g., acetone) to the surface of the tissue. In some embodiments, the surface of the tissue is rubbed with solvent (e.g., acetone) on an applicator (e.g., gauze) to dissolve and remove the cornified layer, induce scratches, and/or induce inflammation. In some embodiments, vector uptake is facilitated by direct intradermal injection of AAV into the tissue. In some embodiments, an injection of 10% saline intradermally at the time of AAV delivery enhances uptake by 10-fold (AAV in saline solution vehicle).

In some embodiments, soft tissues of the eye are treated to abrade and/or disrupt epithelial cells. In some embodiments, the corneal epithelial cells are abraded and/or disrupted prior to or concurrently with application of the vector. In one particular embodiment, corneal epithelial cells are abraded and/or disrupted with a blunted beveled needle in a multiple cross-hatched (grid) pattern. In a particular embodiment, after abrasion and/or disruption of the epithelial cells of the cornea or soft tissues of the eye, the vector is applied to the abraded/treated area in 10% saline vehicle, which facilitates uptake. In some embodiments, inducing mild inflammatory processes and/or sensitizing the nerve termini promotes vector uptake. This may occur at not just the corneal surface, but also the soft mucosal surfaces of the conjunctiva and underside of the eye lid.

In some aspects, treatment of the eye surface to facilitate uptake of the vector includes treatment of corneal epithelium with alcohol (e.g., isopropyl alcohol or ethanol rub), scraping off corneal epithelium with physical tool (e.g., a razor blade or other sharp blade), removal of corneal epithelium with excimer laser, and/or direct intrastromal injection of AAV vector (e.g., in 10% saline), or a combination of two or more such techniques.

In some embodiments, without wishing to be limited by theory, physical or chemical techniques remove epithelial cells to expose neural tissue, for example nerve endings, at or near the surface of the tissue being treated.

In some embodiments, nucleic acids (e.g., DNA or RNA), and/or recombinant viral vectors that are contacted to the treated tissue surface can migrate to neural cells or tissue distant from the site of administration (e.g., to central nervous system (CNS) and/or peripheral nervous system (PNS) cells or tissue).

In some embodiments, a recombinant viral vector includes capsid proteins that are neurotropic (e.g., that preferentially bind to and/or penetrate neural cells or tissue).

In some embodiments, a vector is a recombinant adeno-associated viral vector. In some embodiments, the subject has or is suspected of having a neurological condition or an infection (e.g., a viral infection) of the central or peripheral nervous system, and a replication defective recombinant viral vector is administered (e.g., topically) to the subject.

In some embodiments, one or more rAAV-based compositions disclosed herein is administered in a pharmaceutically acceptable form for administration to a cell or an animal, either alone or in combination with one or more other modalities of therapy, and in particular, for therapy of human cells, tissues, and diseases affecting humans.

If desired, vectors (e.g., rAAV particles or nucleic acid vectors) may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, provided that the additional agents do not cause a significant adverse effect upon contact with the target cells or host tissues. Recombinant viral particles (e.g., rAAV particles) may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, for example, but not limited to, topical treatment regimens. In some embodiments, one or more compositions described in this application may be administered (e.g., alternatively or in addition to topically) via oral, parenteral, intravenous, intranasal, intraarticular, and/or intramuscular routes of administration.

In some embodiments, one or more compositions described herein (e.g., rAAV particles and/or nucleic acids) may be administered by any means suitable for optimal nerve transduction. For example, in some embodiments, suitable modes of administration include intravenous, intracisternal, sub-cutaneous, intradermal, intraganglionic, intrathecal, peripheral nerve terminal, or other neural routes of delivery (e.g., ocular, corneal, intranasal). In some embodiments, one or more compositions described herein (e.g., rAAV particles and/or nucleic acids) may be administered by contacting the one or more compositions with an exposed dermis layer of the skin for transdermal delivery. In some embodiments, one or more compositions described herein (e.g., rAAV particles and/or nucleic acids) may be administered by contacting the one or more compositions with exposed nerve termini.

Suitable routes of administration can be selected by those skilled in the art, e.g., based on the virus being targeted for treatment and/or the site of manifestation of symptoms of infection. For example, in some embodiments, ocular infections (e.g., as a manifestation of alphaherpesvirus) can be treated by removing or abrading the corneal epithelium (e.g., by means such as ethanol, scalpel blade debridement, or excimer laser treatment), followed by topical application of one or more compositions described herein. In some embodiments, ocular infections can be treated by intrastromal injection of one or more compositions described herein. As a further example, in some embodiments, skin infections (e.g., herpes virus oral or genital or other skin lesion, Varicella zoster virus shingles) can be treated by abrading the skin, scratching the skin, or rubbing solvent (e.g., acetone) on the skin, followed by topical application of one or more compositions described herein. In some embodiments, skin infections can be treated by subdermal injection of one or more compositions described herein. As yet a further example, in some embodiments, Epstein-Barr virus and Cytomegalovirus infections can be treated by intravenous injection of one or more compositions described herein.

Typically, these formulations may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver a recombinant viral particle (e.g., an rAAV particle) in suitably formulated pharmaceutical compositions for a particular route of administration.

Non-limiting examples of pharmaceutical forms include compositions suitable for topical administration, and include aqueous solutions or dispersions, creams, ointments, gels, or other suitable topical formulations. In some embodiments, the composition is stable under the conditions of manufacture and storage and is preserved against the contaminating action of microorganisms, such as bacteria and fungi. In some embodiments, the composition is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the composition is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. In some embodiments, inflammation modulators and/or adjuvants are used as liquid carriers.

The amount of vector (e.g., recombinant viral particle) compositions and time of administration of such compositions will be within the purview of the skilled artisan having benefit of the present teachings. It is likely, however, that the administration of therapeutically-effective amounts of the disclosed compositions may be achieved by a single administration, such as for example, a single topical application of sufficient numbers of viral particles to provide therapeutic benefit to the patient undergoing such treatment. Alternatively, in some circumstances, it may be desirable to provide multiple, or successive administrations of the compositions, either over a relatively short, or a relatively prolonged period of time, as may be determined by the medical practitioner overseeing the administration of such compositions.

In some embodiments, the number of viral (e.g., rAAV) particles administered to a subject may be on the order ranging from $10^6$ to $10^{14}$ particles/mL or $10^2$ to $10^{16}$ particles/mL, or any values there between for either range, such as for example, about $10^6$, $10^7$, $10^8$, $10^9$, $10^{10}$, $10^{11}$, $10^{12}$, $10^{13}$, or $10^{14}$ particles/mL. In one embodiment, viral particles of higher than $10^{13}$ particles/mL are be administered. In some embodiments, the number of viral particles administered to a subject may be on the order ranging from $10^6$ to $10^{14}$ vector genomes (vgs)/mL or $10^2$ to $10^{16}$ vgs/mL, or any values there between for either range, such as for example, about $10^6$, $10^7$, $10^8$, $10^9$, $10^{10}$, $10^{11}$, $10^{12}$, $10^{13}$, or $10^{14}$ vgs/mL. In some embodiments, 0.01 mL to 10 mLs of a composition are applied to a subject.

To "treat" or "treating" a disease as the term is used herein, means to reduce the frequency, severity, and/or duration of at least one sign or symptom of a disease or disorder experienced by a subject (e.g., reducing the frequency, severity, or other symptom of viral reactivation in a subject previously infected by a virus). The compositions described above are typically administered to a subject in an effective amount, that is, an amount capable of producing a desirable result. The desirable result will depend upon the active agent being administered. For example, an effective amount of a recombinant viral particle (e.g., rAAV particle) may be an amount of the particle that is capable of transferring a heterologous nucleic acid to a host organ, tissue, or cell (e.g., to a central or peripheral nervous system cell or tissue). In some embodiments, a composition may be administered to a subject as a preventative measure to prevent or reduce the risk of an infection. In some embodiments, a composition may be useful to assist in the treatment of an infection, for example, along with one or more other therapies.

In some embodiments, methods and/or compositions disclosed herein are used to treat a disease or disorder in a subject. Non-limiting examples of diseases and disorders that can be treated by compositions and/or methods disclosed herein include viral meningitis, Eastern equine encephalitis, St Louis encephalitis, Japanese encephalitis, West Nile encephalitis, Herpes simplex encephalitis, Rabies, Lyssavirus, Calif. encephalitis virus, Varicella-zoster encephalitis, La Crosse encephalitis, Measles encephalitis, Poliomyelitis, Dengue virus, Slow virus infections, Subacute sclerosing panencephalitis, Progressive multifocal leukoencephalopathy, Acquired immunodeficiency syndrome (AIDS), Cryptococcal meningitis, Toxoplasmosis, Malaria, Primary amoebic meningoencephalitis, Tuberculosis, Leprosy, Neurosyphilis, Bacterial meningitis, Lyme disease, and/or Neuroborreliosis.

In some embodiments, methods and compositions described herein are used to treat neurological disorders. Non-limiting examples of neurological disorders that are treated using methods and compositions of the present invention include amyotrophic lateral sclerosis, Huntington's disease, Alzheimer's disease, or Parkinson's disease. In some embodiments, other genetic disorders that affect the peripheral nervous system and/or central nervous system can be targeted using methods and compositions described in the application.

Toxicity and efficacy of the compositions utilized in methods of the application can be determined by standard pharmaceutical procedures, using either cells in culture or experimental animals to determine the LD50 (the dose lethal to 50% of the population). The dose ratio between toxicity and efficacy the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Aspects of the disclosure relate to recombinant adeno-associated virus (rAAV) particles for delivery of one or more nucleic acid vectors comprising a gene of interest into various tissues, organs, and/or cells. In some embodiments, the rAAV particles comprise an rAAV capsid protein as described herein, e.g., comprising one or more amino acid substitutions. In some embodiments, the gene of interest encodes a nucleic acid that targets a transcript (e.g., a LAT transcript, a TAL transcript, an ATAL transcript, or other transcript, or any combination of two or more thereof). In some embodiments, the gene of interest encodes an RNA of interest (e.g., a therapeutic siRNA, shRNA, microRNA, antisense RNA, or a ribozyme). In some embodiments, a gene of interest is a replacement gene (e.g., of a gene expressed in nerve cells). In some embodiments, a gene of interest is under the control of a promoter (e.g., an inducible promoter or a constitutive promoter that is active in nerve cells).

Recombinant AAV (rAAV) particles may comprise at a minimum (a) one or more heterologous nucleic acid regions comprising a sequence encoding a gene of interest, and (b) one or more regions comprising inverted terminal repeat (ITR) sequences (e.g., wild-type ITR sequences or engineered ITR sequences) flanking the one or more heterologous nucleic acid regions. In some embodiments, the nucleic acid vector is between 4 kb and 5 kb in size (e.g., 4.2 to 4.7 kb in size). This nucleic acid vector may be encapsidated by a viral capsid, such as an AAV1, AAV2, AAV3, AAV4, AAV5, AAV6, AAV7, AAV8, AAV9, or other AAV capsid, which may comprise a modified capsid protein as described herein. In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complementary vector that contains a region of the nucleic acid vector that is complementary to another region of the nucleic acid vector, initiating the formation of the double-strandedness of the nucleic acid vector.

The rAAV particle may be of any AAV serotype, including any derivative or pseudotype (e.g., 1, 2, 3, 4, 5, 6, 7, 8, 9, 10, 2/1, 2/5, 2/8, or 2/9). As used herein, the serotype of an rAAV viral vector (e.g., an rAAV particle) refers to the serotype of the capsid proteins of the recombinant virus. In some embodiments, the rAAV particle is selected based on neural tropism. AAV serotypes and pseudotypes having a high relative neural tropism are known in the art. For example, in some embodiments, AAV1, AAV5, AAV7, and AAV8 have more favorable neural tropism and increased expression and spread of viral transgene when compared to AAV2 (see, e.g., McFarland, N. R., et al. (2009) J. Neurochem. 109(3): 838-845). In some embodiments, the rAAV particle is AAV8. In some embodiments, the rAAV particle is of an AAV8 serotype or a pseudotype or derivative thereof. AAV serotypes and derivatives/pseudotypes, and methods of producing such derivatives/pseudotypes are known in the art (see, e.g., Mol Ther. 2012 April; 20(4): 699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV1, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector may be combined with one or more helper plasmids, e.g., that contain a rep gene (e.g., encoding Rep78, Rep68, Rep52 and Rep40) and a cap gene (e.g., encoding VP1, VP2, and VP3, including a modified VP3 region as described herein), and transfected into a producer cell line such that the rAAV particle can be packaged and subsequently purified.

In some embodiments, the one or more helper plasmids include a first helper plasmid comprising a rep gene and a cap gene (e.g., encoding a rAAV capsid protein as described herein) and a second helper plasmid comprising a E1a gene, a E1b gene, a E4 gene, a E2a gene, and a VA gene. In some embodiments, the rep gene is a rep gene derived from AAV2 or AAV6 and the cap gene is derived from AAV2 or AAV6 and may include modifications to the gene in order to produce the modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

A non-limiting example of an rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HS Vs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

The disclosure also contemplates host cells that comprise at least one of the disclosed rAAV particles or nucleic acid vectors. Such host cells include mammalian host cells, with human host cells being preferred, and may be either isolated, in cell or tissue culture. In the case of genetically modified animal models (e.g., a mouse), the transformed host cells may be comprised within the body of a non-human animal itself. In some embodiments, the host cell is a cell of erythroid lineage, such as a CD36+ burst-forming units-erythroid (BFU-E) cell or a colony-forming unit-erythroid (CFUE-E) progenitor cell.

In some embodiments, a nucleic acid that targets a gene of interest (e.g., a viral gene or other pathogen gene) is a ribozyme (a catalytic RNA). In some embodiments, the ribozyme is a ribonucleic acid (RNA) enzyme that catalyzes the cleavage or degradation of a target nucleic acid (e.g., a target DNA or RNA of interest). In some embodiments, the ribozyme is a hammerhead ribozyme. In some embodiments, a hammerhead ribozyme catalyzes a specific cleavage in a target RNA (e.g., a viral RNA, for example the LAT RNA, TAL RNA, ATAL RNA, or LAT region miRNAs, TAL region miRNAs, ATAL region miRNAs, or one or more of their precursor RNAs).

In some embodiments, a nucleic acid that targets a viral gene is an interfering RNA. RNAi is a remarkably efficient process whereby double-stranded RNA (dsRNA) induces the sequence-specific degradation of homologous mRNA in animals and plant cells (Hutvagner and Zamore (2002), Curr. Opin. Genet. Dev., 12, 225-232; Sharp (2001), Genes Dev., 15, 485-490). In mammalian cells, RNAi can be triggered by a variety of RNAi agents including 21-nucleotide (nt) duplexes of small interfering RNA (siRNA) (Chiu et al. (2002), Mol. Cell., 10, 549-561; Elbashir et al. (2001), Nature, 411, 494-498), or by micro-RNAs (mRNA), functional small-hairpin RNA (shRNA), or other dsRNAs which are expressed in-vivo using DNA templates with RNA polymerase III promoters (Zeng et al. (2002), Mol. Cell, 9, 1327-1333; Paddison et al. (2002), Genes Dev., 16, 948-958; Lee et al. (2002), Nature Biotechnol., 20, 500-505; Paul et al. (2002), Nature Biotechnol., 20, 505-508; Tuschl, T. (2002), Nature Biotechnol., 20, 440-448; Yu et al. (2002), Proc. Natl. Acad. Sci. USA, 99(9), 6047-6052; McManus et al. (2002), RNA, 8, 842-850; Sui et al. (2002), Proc. Natl. Acad. Sci. USA, 99(6), 5515-5520.)

The molecular mechanism of RNAi is remarkably conserved among eukaryotic organisms. The dsRNA or hairpin RNA structure of an RNAi agent is recognized and processed by Dicer, an enzyme of the RNase III family, into 21-25 nucleotide small interfering RNAs (siRNAs). The siRNAs interact with the cellular proteins Dicer and R2D2, to form a complex (RISC-loading complex or RLC) which in turn facilitates the formation of a siRNA/multi-protein complex called RISC(RNA-induced silencing complex). The RLC then interacts with additional other proteins including Ago2 to form the active RISC that contains one of the two siRNA strands termed the guide strand. The active RISC complex is capable of recognizing the target RNA via Watson-Crick base pairing with the guide strand. The RISC complex then cleaves the target RNA, which is then released, thereby regenerating a RISC complex which is free to catalyze a new cycle of target recognition and cleavage (Tomari & Zamore, 2005).

RNA interference can also be triggered by micro RNAs (miRNAs). miRNAs are generated from long transcripts, called pri-miRNA, which are synthesized by RNA polymerase II (BRACHT et al., 2004; CAI et al., 2004; Lee et al., 2004). Pri-miRNA is processed by RNase III enzyme Drosha and its partner Pasha to form pre-miRNA, which is 70 nt long and folds into a hairpin structure (Lee et al., 2003; Denli et al., 2004). It is then exported by Exportin 5 from the nucleus to the cytoplasm (Yi et al., 2003; BOHNSACK et al., 2004; Lund et al., 2004; Zeng & Cullen, 2004), where it is further processed by Dicer to form single stranded miRNA (Grishok et al., 2001; Hutvagner et al., 2001; Ketting et al., 2001). This processing step may be tightly coupled with loading of the miRNA into the RISC, which is then capable of either cleaving the target RNA via RNAi (if the target perfectly complements the miRNA in sequence) or mediating translational silencing of the target RNA (if the miRNA contains mismatches multiple sequences in the target RNA). This process has been mimicked by shRNAs synthesized from either Pol III or Pol II promoters (Xia et al., 2002; Shi, 2003; Zeng & Cullen, 2003; Zhou et al., 2005).

In some embodiments, a nucleic acid targets a latency-associated region transcript of a virus. As used herein, in some embodiments, a "latency-associated region transcript" refers to a non-coding regulatory RNA transcribed during viral latency with diverse functions including viral reactivation. In some embodiments, examples of such transcripts include a LAT transcript, a TAL transcript, an ATAL transcript, or other transcript, or any combination of two or more thereof. In some embodiments, the latency-associated region transcript is encoded between positions 117,344 and 127,151 of the human herpesvirus 1 genome as given in the non-limiting example of an HSV-1 genome GenBank: X14112.1. It should be appreciated that such transcripts encoded by this region are not limited to a particular directionality and/or sense. For example, in some embodiments, the transcript is transcribed in a direction toward position 127,251, such as a LAT transcript described herein. In some embodiments, the transcript is transcribed in a direction toward position 117,344, such as a TAL transcript described herein. In some embodiments, the transcript is antisense to a transcript that is transcribed in either direction (e.g., as an ATAL transcript described herein, which is antisense to a TAL transcript). It is envisioned that any non-coding regulatory transcript involved in viral reactivation can be targeted in accordance with the technology provided in the disclosure.

In some embodiments, the LAT transcript is encoded between positions 118,777 and 127,251 of the HSV-1 genome as given in the non-limiting example of an HSV-1 genome Genbank NC_001806.2. In some embodiments, the LAT transcript is encoded between positions 118,805 and 127,151 of the human herpesvirus 1 genome as given in the non-limiting example of an HSV-1 genome GenBank: X14112.1 (SEQ ID NO: 15). In another embodiment, the nucleic acid targets the 5' exon and intron regions of LAT. In some embodiments, the nucleic acid targets the LAT intron. In some embodiments, the nucleic acid targets the LAT 3' exon.

```
Gene sequencing encoding LAT:
                                                                    (SEQ ID NO: 15)
cgcgggtggtgcgaaagactttccgggcgcgtccgggtgccgcggctctccgggcccccctgcagccggggcggccaaggggcgtcggcgacat cctcccctaagcgccggccggccgctggtctgttttttcgttttccccgtttcgggggtggtgggggttgcggtttctgtttctttaacccgt ctggggtgtttttcgttccgtcgccggaatgtttcgttcgtctgtccctcacggggcgaaggccgcgtacggcccgggacgaggggcccccga ccgcggcggtccgggcccgtccggacccgctcgccggcacgcgacgcgaaaaaggcccccggaggcttttccggttccggcccggggcct gagatgaacactcggggttaccgccaacgccggccccgtggcggcccggcccggggccccggcggacccaaggggcccggcccggggcccc acaacgcccggcgcatgcgctgtggttttttttttcctcggtgttctgccgggctccatcgcctttcctgttctcgcttctccccccccttc ttcaccccagtaccctcctccctcccttcctccccgttatcccactcgtcgagggcgcccggtgtcgttcaacaaagacgccgcgtttcca ggtaggttagacacctgcttctccccaatagaggggggggacccaaacgacaggggcgcccagaggctaaggtcggccacgccactcgcggg tgggctcgtgttacagcacaccagcccgttcttttccccccctcccacccttagtcagactctgttacttacccgtccgaccaccaactgcccc cttatctaagggccggctggaagaccgccaggggtcggccggtgtcgctgtaaccccccacgccaatgacccacgtactccaagaaggcatgt gtcccacccccgcctgtgttttgtgcctggctctctatgcttgggtcttactgcctgggggggggagtgcggggagggggggtgtggaagga aatgcacggcgcgtgtgtaccccccctaaagttgttcctaaagcgaggatacggaggagtggcgggtgccggggggaccggggtgatctctggca cgcgggggtgggaagggtcgggggaggggggatggagtaccggcccacctggccgcgcgggtgcgcgtgcctttgcacaccaacccacgtcc cccggcggtctctaagaagcaccgcccccctccttcataccaccgagcatgcctgggtgtgggttggtaaccaacacgccatcccctcgtct cctgtgattctctggctgcaccgcattcttgttttctaactatgttcctgtttctgtctcccccccccaccccctccgccccacccccaaca cccacgtctgtggtgtggccgacccccttttgggcgcccgtcccgcccgccacccctcccatccttgttgccctatagtgtagttaaccc cccgccctttgtggcggccagaggccaggtcagtccgggcgggcaggcgctcgcggaaacttaacaccacacccaacccactgtggttctgg ctccatgccagtggcaggatgctttcggggatcggtggtcaggcagcccgggccgcggctctgtggttaacaccagagcctgcccaacatggca cccccactcccacgcaccccactcccacgcaccccactcccacgcaccccactcccacg caccccactcccacgcaccccactcccacgcaccccactcccacgcaccccactcccacgcatcccgcgatacatccaacacagacagg gaaaagatacaaaagtaaacctttatttcccaacagacagcaaaaatcccctgagttttttttattagggccaacacaaaagacccgctggtg tgtggtgcccgtgtctttcacttttcccctccccgacacggattggctggtgtagtgggcgcggccagagaccacccagcgcccgacccccc tccccacaaacacggggggcgtcccttattgttttccctcgtcccgggtcgacgcccctgctcccggaccacgggtgccgagaccgcaggct gcggaagtccagggcgcccactagggtgccctggtcgaacagcatgttccccacgggggtcatccagaggctgttccactccgacgcgggggcc gtcgggtactcggggggcatcacgtggttacccgcggtctcggggagcagggtgcggcggctccagccggggaccgcggcccgcagccgggtcg ccatgtttcccgtctggtccaccaggaccacgtacgcccgatgttcccgtctccatgtccaggatgggcaggcagtcccccgtgatagtctt gttcacgtaaggcgacagggcgaccacgctagagaccccgagatgggcaggtagcgcgtgaggccgcccgcggggacggccccggaagtctcc gcgtggcgcgtcttccgggcacacttcctcggccccccgcggcccagaagcagcgcgggggccgagggaggtttcctcttgtctccctcccaggg caccgacggccccgcccgaggaggcggaagcggaggaggacgcggcccggcggcggaagaggcggccccgcgggggtcggggccgaggagga agaggcagaggaggaagaggcggaggccgccgaggacgtcagggggtcccgggcccaccctggccgcgcccccccggccctgagtcggaggg gggtgcgtcgccgccctcttggcccctgccggcgcgaggggggacgcgtggactgggggagggtttcctggcccgacccgcgcctcttcc tcggacgcaccgccgcctcctgctcgacagaggcggcggaggggagcggggcggcgccggaggggcggcgccgcgggagggcccgtgcccacc
```

-continued

```
ctccacgcccggccccccgagccgcgcgccaccgtcgcacgcgcccggcacagactctgttcttggttcgcggcctgagccagggacgagtgc gactggggcacacggcgcgcgtccgcggggcgggcggccggctccgccccggggccggggcgcggggccgggcccgaggcggcgctcgca cgcacggggccacggccgcgcggggggcgcgcgggtcccgacgcggccgcggacgcggggggcccggggcgggggcggagcctggcatgggcgc cgcgggggggcctgtggggagaggccggggggggagtcgctgatcactatgggtctctgttgtttgcaaggggggcgggtctgttgacaaggggg cccgtccggcccctcggccgcccgcctccgcttcaacaaccccaaccccaaccccaaccccccggaggggccagacgccccccgcggcgccg cggctcgcgactggcgggagccgccgccgctgctgttggtggtggtgttggtgttactgctgccgtgtggcccgatgggcgccgaggggggg cgctgtccgagccgcggccggctggggggctgcgtgagacgcccgcccgtcacggggggcgcggcggcgcctctgcgtgggggggcgcgggc gtccggcggggggcgggcggtacgtagtctgctgcaagagacaacggggggcgcgatcaggttacgcccctccccggcccgcccttcctcgc ccgcccgcctattcctccctccccccccctcctcctcctcctcccccagggtccttgccgccccccgcctcaccgtcgtccaggtcgtcgtcat cctcgtccgtggtgggctccgggtgggtgggcgacagggccctcaccgtgtgcccccccagggtcaggtaccgcggggcgaaccgctgattgcc cgtccagataaagtccacggccgtgcccgccctgacggcctcctcggcctccatgcgggtctgggggtcgttcacgatcgggatggtgctgaac gacccgctgggcgtcacgcccactatcaggtacaccagcttggcgttgcacagcgggcaggtgttgcgcaattgcatccaggttttcatgcacg ggatgcagaagcggtgcatgcacgggaaggtgtcgcagcgcaggtggggcgcgatctcatccgtgcacacggcgcacacgtcgccctcgtcgct cccccgtcctctcgagggggggcgccccgcaactgccgggtcttcctcgcggggggggctcccccgagaccgccccccatccacgccc tgcggccccagcagcccgtctcgaacagttccgtgtccgtgctgtccgcctcggaggcggagtcgtcgtcatggtggtcggcgtccccgcc cccccacttcggtctccgcctcagagtcgctgctgtccggcaggtctcggtcgcaggggaaacacccagacatccggggcgggctaaggggaaaa aaggggggcgggtaagaatggggggggatttcccgcgtcaatcagcacccacgagttccccctctcccccccccgcctcacaaagtcctgcccc cctgctggcctcggaagaggggggagaaaggggtctgcaaccaaaggtggtctgggtccgtcctttggatcccgaccctcttcttccctcttc tcccgccctccagacgcaccggagtcgggggtcccacggcgtcccccaaatatggcgggcggctcctccccaccccctagatgcgtgtgagta aggggggcctgcgtatgagtcagtggggaccacgcccccaacacggcgacccggtccttgtgtgtttgttgtgggggcgtgtctctgtgtatg agtcaggggtcccacggcgaccccgggccctgcgtctgagtcaaaggggccatgtgtatgtgttgggggtctgtatatataaagtcaggggt cacatggcgaccccaacagggcgaccccggtccctgtatatataggtcaggggttccgcacccctaacatggcgccccggtccctgtat atatagtgtcacggggttccacgcccctaacatggcgcccaacatggcgcccggctcccgtgtatgagtgggggtccccaacatggcggcc ggttccagtgtaagggtcgggggtccccaacatggcgccccccaatatggcgccccccaatatggcgcccagacatggcgcccggccctca cctcgcgctgggggcggccctcaggccggcgggtactcgctccggggcggggctccatgggggtcgtatgcggctggagggtcgcggacggagg gtccctgggggtcgcaacgtaggcggggcttctgtggtgatgcggagaggggcggcccgagtctgcctggctgctgcgtctcgctccgagtgc cgaggtgcaaatgcgaccagactgtcgggccagggctaacttataccccacgcctttcccctccccaaaggggcggcagtgacgattccccaa tggccgcgcgtcccaggggaggcaggcccaccgcggggcggccccgtccccggggaccaacccggcgcccccaaagaatatcattagcatgcac ggcccggcccccgatttgggggcccaaccccggtgtccccaaagaacccattagcatgcccctcccgccgacgcaacaggggcttggcctgcg tcggtgccccggggcttcccgccttcccgaagaaactcattaccataccggaaccccaggggaccaatgcgggttcattgagcgacccgcggg ccaatgcgcgaggggccgtgtgttccgccaaaaaagcaattagcataacccggaaccccaggggagtggttacgcgcggcgcgggaggcgggga ataccggggttgcccattaagggccgcgggaattgccggaagcgggaagggcggccggggccgcccattaatgagtttctaattac cataccgggaagcggaacaaggcctcttgcaagttttaattaccataccgggaagtgggcggcccggcccattgggcggtaactcccgcccaa tgggccgggccccgaagactcggcggacgctggttggccgggccccgccgcgctggcggccgccgattggccagtcccgcccccgaggcggccc gccctgtgagggcgggctggctccaagcgtatatatgcgcggctcctgccatcgtctctccggagagcggcttggtgcggagctcccgggagct ccgcggaagacccaggccgcctcgggtgtaacgttagaccgagttcgccgggccggctccgcggggccagggcccgggcacgggcctcgggcccc aggcacggcccgatgaccgcctcggcctccgccaccggcgccgaaccgagcccggtcggcccgctcgcgggcccacgagccgcggcgcgcca ggcggcggccgaggcccagaccaccaggtggcgcacccggacgtggggcgagaagcgcaccccgcgcgggggtcgcggggtcgcgggggtcgc gggggtcgcggggggtcgcggggggctccggcgcccctccccgcccgcgcgtcgcaggcgcaggcgcgccaggtgctccgcggtgacgcgcag gcggagggcgaggcgcggcggaaggcggaaggggcgcgagggggggtgggaggggtcagcccccgccccccgggcccacgccgggcggtgg
```

-continued
```
gggccggggccggggggcggcggcggtgggccgggcctctggcgccggctcgggcgggggctgtccggccagtcgtcgtcatcgtcgtcgtcg gacgcggactcgggaacgtggagccactggcgcagcagcagcgaacaagaaggcggggcccaccggcggggggcggcggcggggcggcc gcgggcgcgctcctgaccgcgggttccgagttgggcgtggaggttacctgggactgtgcggttgggacggcgcccgtgggccgggcggccggg ggcggcgggggccgcgatggcggcggcggcgggccatggagacagagagcgtgccggggtggtagagtttgacaggcaagcatgtgcgtgcaga ggcgagtagtgcttgcctgtctaactcgctagtctcggccgcgggggggcccgggctgcccgccgccaccgctttaaagggccgcgcgcgacccc cgggggggtgtgttttgggggggcccgttttcggcgtctggccgctcctcccccgctcctcccccgctcctcccccgctcctcccccgct cctcccccgctcctcccccgctcctcccccgctcctcccccgctcctcccccgctcctcccccgctcctcccccgctcctcccccg ctcctcccccgctcctcccccgctcctcccccgctcctcccccgctcctcccccgctcccgcggcccgcccccccac gcccgccgcgcgcgcacgccgcccggaccgccgcccgccttttttgcgcgcgcgcgcccgcggggggcccgggctgccacaggtgaaacc aacagagcacggcgcactccgcacgtcacacgtcacgtcatccaccacacctgcccaacaacacaactcacagcgacaactcaccgcgcaacaa ctcctgttcctcatccacacgtcaccgcgcacctcccgctcctccagacgtaccccggcgcaacacaccgctcctgctacacaccaccgccccc tccccagcccagccctcccccagcccagccctccccggcccagccctccccggcccagccctccccggcccagccctccccggcccagc cctccccggcccagccctccccggcccagccctccccggcgcgtcccgcgctccctcggggggttcgggcatctctacctcagtgccgcca atctcaggtcagagatccaaaccctccggggggcgcccgcgcaccaccaccgcccctcgcccctcccgcccctcgcccctcccgcccctcgcc ccctcccgcccctcgcccctcccgcccctcgcccctcccgcccctcgcccctcccgcccctcgcccctcccgcccctcgcccctcccgc ccctcgcccctcccgcccctcgcccctcccgcccctcgcccctcccgcccctcgcccctcccgcccctcgcccctcccgcccctcgccc cctcccgcccctcgcccctcccgcccctcgcccctcccgcccctcgcccctcccgcccctcgcccctcccgcccctcgcccctcccgcc cctcgaataaaca
```

In some embodiments, a non-limiting example of a sequence of the 5' exon and intron regions of LAT was searched for GUC, CUC or UUC triplets as potential cleavage targets (see, for example, FIG. 8A). Ribozyme binding arms complementary to the sequence flanking the potential cleavage targets were designed (for example FIG. 8B). Subsequent in silico simulation of the modified ribozymes was used to select candidate ribozymes predicted to have a correctly folded catalytic core and open hybridizing arms (for example FIG. 8C). One skilled in the art will understand that the example of the LAT sequence does not limit the scope of the application, and that homologous transcripts in viruses other than HSV-1 could be targeted for cleavage in a similar manner based on this disclosure. Similarly, the example of the GUC codon selected does not limit the scope of this application, and one skilled in the art will appreciate that other codons could have been selected and addressed with a specific, rationally-designed ribozyme, following the teachings of this application. As used herein, in some embodiments, "LAT" generally refers to any latency-associated transcript of a virus that comprises a non-coding sequence. However, in some embodiments, "LAT" may be used in a more specific context to refer to the transcript targeted in accordance with FIGS. 8A-8C (e.g., a transcript encoded by SEQ ID NO: 15).

In some embodiments, a ribozyme is used to target LAT. In some embodiments, the ribozyme comprises 5'-GGACA-CUGAUGAGCGCUUCGGCGCGAAACGAAC-3' (SEQ ID NO: 14). However, one skilled the art will appreciate that other ribozyme designs that also comprise hybridization regions flanking the target codon that are not self-complementary will have desirable hybridization function. Similarly, one skilled in the art will appreciate that selection of ribozymes that maintain correct structure of the catalytic domain will have desirable LAT cleavage function. In addition, one skilled in the art will appreciate that selection of ribozymes with the greatest catalytic activities to the target RNAs is desirable.

In some embodiments, the nucleic acid targets a region upstream of the 5' exon region of LAT. In some embodiments, the nucleic acid targets a latency-associated transcript that comprises long non-coding RNA that overlaps with the 5' exon region of LAT. For example, in some embodiments, the latency-associated transcript is encoded between positions 116,800 and 119,200 of the HSV-1 genome as given in the non-limiting example of an HSV-1 genome Genbank X14112.1. In some embodiments, a transcript encoded in this region is referred to as a "TAL" transcript—a latency-associated transcript encoded by a region overlapping LAT but present as a transcript independent of LAT (e.g., "LAT" as used in the more specific context described above). In yet other embodiments, a transcript encoded in this region that is antisense to TAL is referred to as "ATAL."

In some embodiments, a TAL transcript is encoded between positions 119,044 and 117,344 of the human herpesvirus 1 genome as given in the non-limiting example of an HSV-1 genome GenBank: X14112.1 (SEQ ID NO: 16).

```
Gene sequencing encoding TAL:
                                                                                  (SEQ ID NO: 16)
    tgaggggacagacgaacgaaacattccggcgacggaacgaaaaacacccccagacgggttaaagaaacagaaaccgcaaccccccaccacccccga aacggggaaaacgaaaaaacagaccagcggccggccggcgcttaggggggaggatgtcgccgacgccccttggccgccccggctgcaggggggc
```

-continued

```
ccggagagccgcggcacccggacgcgcccggaaagtctttcgcaccaccgcgatcggcacggccgcgccccgcttttataaaggctgagatga
cgcagcaaaaacaggccacagcaccacgtgggtaggtgatgtaattttattttcctcgtctgcggcctaatggatttccgggcgcggtgccct
gtctgcagagcacttaacggattgatatctcgcgggcacgcgcgcccttaatggaccggcgcggggcgggggccggatacccacacgggcggg
ggggggtgtcgcgggccgtctgctggcccgcggccacataaacaatgactctgggcctttctgcctctgccgcttgtgagtgcgcgcgccggc
tctgcggtgtcggcggcggctgcggcggctgcggcggccgccgtgttcggtctcggtagccggccggcgggtggactcgcggggggccggaggg
tggaaggcagggggtgtaggatgggtatcaggacttccacttcccgtccttccatccccgttccctcggttgttcctcgcctcccccaaca
ccccgccgctttccgttggggttgttattgttgtcgggatcgtgcgggccgggggtcgccggggcaggggcggggcgtgggcggggtgctcg
tcgatcgaccgggctcagtgggggcgtggggtgggtgggagaaggcgaggagactgggtggggtgtcggtgggtggttgttttttgtggttgt
ttttgtgtctgttcccgtccccgtcaccccctcctccgtccctccgtcccccgtcgcgggtgtttgtgtttgtttattccgacattggtt
tatttaaataaacacagccgttctgcgtgtctgttcttgcgtgtggctggggcttatatgtggggtcccggggggcgggatggggtttagcggc
ggggggcggcgcgccggacggggcgctggagataacggccccgggaacggggaccgggctgggtatcccgaggtgggtgggtgggcggcg
gtggccgggccgggccgggccgggccgggtgggcggggtttggaaaaacgaggaggaggaggagaaggcgggggggggggagacggggg
gaaagcaaggacacggcccggggggtgggagcgcgggccgggccgctcgtaagagccgcgacccggccgccgggagcgttgtcgccgtcggtc
tgccggccccgtccctcccttttttgaccaaccagcgccccccccctcaccaccattcctactaccaccaccaccaccaccgacacct
cccgcgcaccccgcccacatcccccccaacccgcaccaccagcacgggttgggggtagcaggggatcaaagggggcaaagccggcggggcg
gttcggggggggggggggggcgggaaaccaagtaggcccgcccatccgcggcccctcccggcagccacgccccagcgtcgggtgtcacggg
gaaagagc
```

In some embodiments, an ATAL transcript is encoded between positions 117,400 and 118,710 of the human herpesvirus 1 genome as given in the non-limiting example of an HSV-1 genome GenBank: X14112.1 (SEQ ID NO: 17).

```
Gene sequencing encoding ATAL:
                                                                        (SEQ ID NO: 17)
tgggcgggcctacttggtttcccgccccccccccccccccgaaccgccccgccggctttgc Accordingly, aspects of the disclosure relate to the discovery of these TAL and ATAL transcripts as targets for preventing or eliminating viral reactivation. In some embodiments, TAL and/or ATAL may be targeted in addition to LAT or as an alternative to LAT. For example, in some embodiments, the disclosure provides techniques useful for preventing or eliminating viral reactivation. In some embodiments, these techniques can involve targeting one or more of LAT, TAL, and ATAL (e.g., targeting LAT; targeting TAL; targeting ATAL; targeting LAT and TAL; targeting LAT and ATAL; targeting TAL and ATAL; or targeting LAT, TAL, and ATAL). In some embodiments, these techniques can involve targeting any region of LAT, TAL, ATAL, or two or more (e.g., 2, 3, 4, 5, 6, 7, 8, 9, 10, or more) regions in LAT, TAL, ATAL, or any combination of two or three of the transcripts thereof.

Figure 17:
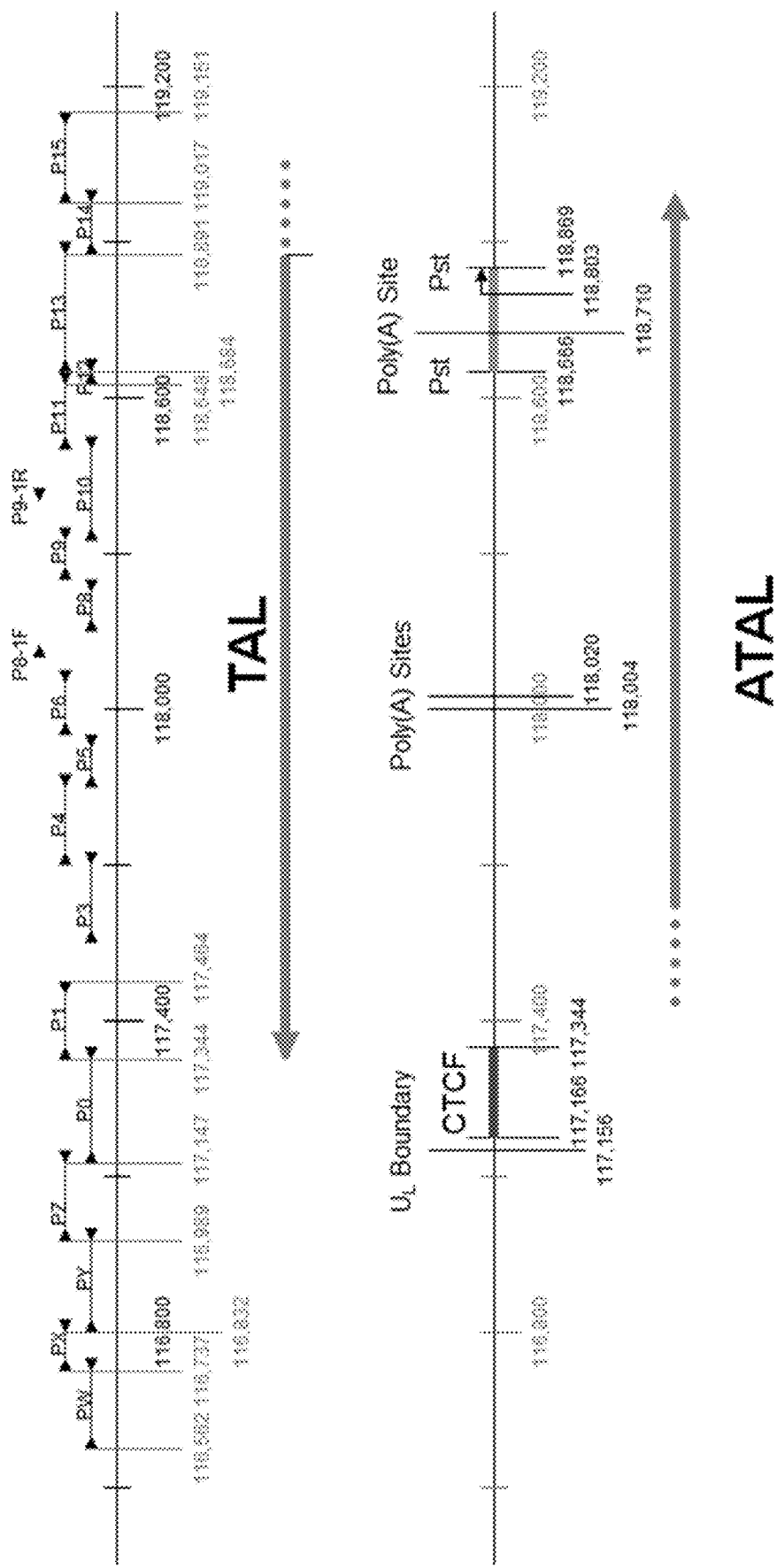
FIG. 17 illustrates mapping of the TAL and ATAL transcripts.
Figure 18:
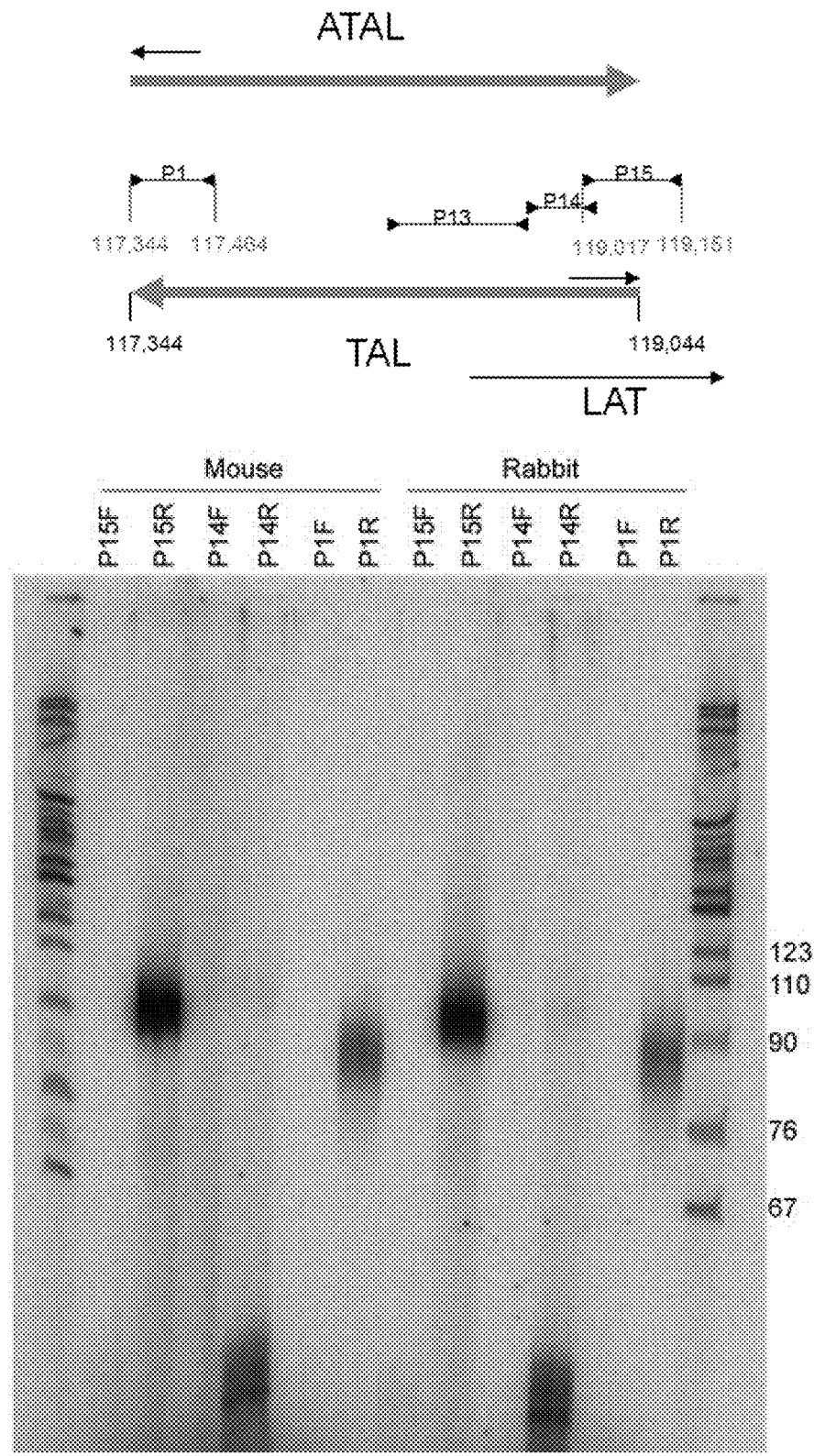
FIG. 18 shows primer extension to map the 5' and 3' ends of the ATAL and TAL transcripts. P1R was used to map the 5' end of the ATAL transcript while P15R was used to map the 5' end of the TAL transcript. The map for both constructs and the resulting Northern blot analysis are shown.

As depicted in FIGS. 17-18, a region of TAL overlaps with a region of LAT, and the molecules are transcribed in opposite directions. Because ATAL is antisense to TAL, and ATAL is transcribed in the same direction as LAT, it is envisioned that a single targeting nucleic acid can be used to target more than one type of transcript (e.g., a single ribozyme can hybridize with either LAT or ATAL).

In some embodiments, a non-limiting example of a sequence of TAL was searched for GUC, CUC, UUC, UUA, CUU, AUU, UUU, AUC, or GUU triplets as potential cleavage targets. Ribozyme binding arms complementary to the sequence flanking the potential cleavage targets were designed. Examples of ribozyme sequences useful for targeting TAL are shown in Table I. These TAL-targeting ribozymes were designed based on the corresponding TAL target sequences listed in Table II.

TABLE 1

Non-limiting examples of TAL Ribozyme Sequences

| Identifier | SEQ ID NO. | Ribozyme Sequence |
|---|---|---|
| 57a | 18 | UGUUUCUUCUGAUGAGGCCGAAAGGCCGAAAACCCG |
| 57b | 19 | CUGUUUCUUCUGAUGAGGCCGAAAGGCCGAAAACCCGU |
| 223 | 20 | UGCGACUGAUGAGGCCGAAAGGCCGAAAGACUUU |
| 325 | 21 | GGAAAAUAACUGAUGAGGCCGAAAGGCCGAAAUUACAUC |
| 327 | 22 | AGGAAAAUCUGAUGAGGCCGAAAGGCCGAAAAAUUACAU |
| 328 | 23 | AGGAAAACUGAUGAGGCCGAAAGGCCGAAAAAUUACA |
| 330 | 24 | GAGGAACUGAUGAGGCCGAAAGGCCGAAAUAAAAUUAC |
| 396 | 25 | GAGAUAUCCUGAUGAGGCCGAAAGGCCGAAAUCCGUUA |
| 685 | 26 | AAGUCCUCUGAUGAGGCCGAAAGGCCGAAAUACCCA |
| 775 | 27 | GACAACAAUCUGAUGAGGCCGAAAGGCCGAAACAACCC |
| 781 | 28 | CCCGACCUGAUGAGGCCGAAAGGCCGAAACAAUAACA |
| 1063 | 29 | CAAGAACACUGAUGAGGCCGAAAGGCCGAAACACGC |

TABLE II

Non-limiting examples of TAL Target Sequences

| Identifier | SEQ ID NO. | Target Sequence |
|---|---|---|
| 57a | 30 | CGGGUUaAAGAAACA |
| 57b | 31 | ACGGGUUaAAGAAACAG |
| 223 | 32 | AAAGUCUuUCGCA |
| 325 | 33 | GAUGUAAUuUUAUUUUCC |
| 327 | 34 | AUGUAAUUUuAUUUUCCU |
| 328 | 35 | UGUAAUUUUaUUUUCCU |
| 330 | 36 | GUAAUUUUAUuUUCCUC |
| 396 | 37 | UAACGGAUuGAUAUCUC |
| 685 | 38 | UGGGUAUcAGGACUU |
| 775 | 39 | GGGUUGUuAUUGUUGUC |
| 781 | 40 | UGUUAUUGUuGUCGGG |
| 1063 | 41 | GCGUGUcUGUUCUUG |

It should be appreciated that, in some embodiments, the ribozymes and corresponding target sequences listed in Tables I and II, respectively, are non-limiting and may be used to illustrate a general strategy for targeting TAL. For example, in some embodiments, TAL-targeting ribozyme sequences differing from those listed in Table I can be designed to target the TAL target sequences listed in Table II (e.g., by using a hybridization sequence overlapping with one or more of the sequences listed in Table I). In yet other embodiments, alternative TAL target sequences can be identified by any suitable means, whereupon a TAL-targeting nucleic acid (e.g., TAL-targeting ribozyme) can be appropriately designed to hybridize with TAL.

Several physical parameters were determined by computational methods for each TAL-targeting sequence in order to evaluate the ribozymes and are listed in Table III. Computational techniques that can be used to reproduce these calculations and conduct similar analyses are known in the art (e.g., the parameters shown were calculated using ALADDIN, "SeArch computing tooL for hAmmerheaD ribozyme DesIgN"; see Mercatanti, A., et al. (2012) Methods Mol. Bio. 848:337-356; Kharma, N., et al. (2016) Nucleic Acids Res. 44(4): e39). In some embodiments, the TAL ribozyme folds with a delta G value of between about −13.0 kcal/mol and about −10.0 kcal/mol. In some embodiments, the left and right arms of the TAL ribozyme bind to a target sequence with a comparable delta G value. For example, as shown in Table III, the TAL ribozyme binds to a left substrate binding domain (LSBD) and a right substrate binding domain (RSBD) of a target sequence with comparable delta G values. In some embodiments, the difference between LSBD and RSBD is less than 1.5 kcal/mol (e.g., approximately 0.0, 0.1, 0.2, 0.3, 0.4, 0.5, 0.6, 0.7, 0.8, 0.9, 1.0, 1.1, 1.2, 1.3, 1.4, or 1.5 kcal/mol). In some embodiments, the TAL ribozyme is characterized by a folding score of at least 0.80. In some embodiments, the TAL ribozyme is characterized by a folding score of between about 0.80 and about 1.0. In some embodiments, the folding score is between about 0.90 and about 1.0 (e.g., a folding value of approximately 0.90, 0.91, 0.92, 0.93, 0.94, 0.95, 0.96, 0.97, 0.98, 0.99, or 1.0).

TABLE III

Non-limiting examples of TAL Ribozyme Properties

| Identifier | NUX | LSBD | RSBD | L Accessibility | R Accessibility | L Uniqueness | R Uniqueness | Delta G | Folding Score |
|---|---|---|---|---|---|---|---|---|---|
| 57a | UUA | −12.1 | −11.5 | 49.8 | 63.7 | 1551 (0.2%) | — | −11.3 | 0.98 |
| 57b | UUA | −14.3 | −13.6 | 56.9 | 67.7 | 1550 (14.5%) | — | −11.3 | 0.98 |
| 223 | CUU | −10.6 | −10.3 | 57.1 | 39.9 | — | — | −11.3 | 0.94 |
| 325 | AUU | −11.1 | −11.7 | 81.7 | 78.8 | — | — | −12.4 | 0.74 |
| 327 | UUU | −10.5 | −11.6 | 87.8 | 71.6 | — | — | −11.3 | 0.91 |
| 328 | UUA | −10.3 | −10.5 | 87.8 | 67.6 | — | — | −11.3 | 0.94 |
| 330 | AUU | −10.6 | −11.1 | 92.7 | 45.5 | — | 733 (33.3%) | −11.3 | 0.98 |
| 396 | AUU | −13.6 | −12.8 | 41 | 48.3 | — | — | −13.1 | 0.8 |
| 685 | AUC | −13.3 | −13 | 42.9 | 71.4 | 1192 (57%) | — | −11.3 | 0.93 |
| 775 | GUU | −14 | −13.9 | 40.8 | 41.9 | — | — | −11.3 | 0.94 |
| 781 | GUU | −12.8 | −13.6 | 35.9 | 43.9 | — | 1678 (33.2%) | −11.3 | 0.96 |
| 1063 | GUC | −12.3 | −12.7 | 50 | 37.7 | 1073 (16.7%) | — | −11.3 | 0.95 |

In some embodiments, a non-limiting example of a sequence of ATAL was searched for GUC, CUC, UUC, AUU, or AUC triplets as potential cleavage targets. Ribozyme binding arms complementary to the sequence flanking the potential cleavage targets were designed. Examples of ribozyme sequences useful for targeting ATAL are shown in Table IV. These ATAL-targeting ribozymes were designed based on the corresponding ATAL target sequences listed in Table V.

TABLE IV

Non-limiting examples of ATAL Ribozyme Sequences

| Identifier | SEQ ID NO. | Ribozyme Sequence |
|---|---|---|
| 262 | 42 | CCCUUUUUUCUGAUGAGGCCGAAAGGCCGAAACCAACC |
| 813 | 43 | UGGGACUGAUGAGGCCGAAAGGCCGAAAAGGCGA |
| 1182 | 44 | AUAAACAAUCUGAUGAGGCCGAAAGGCCGAAACUCUG |
| 1185 | 45 | CACAUAAACCUGAUGAGGCCGAAAGGCCGAAAUGACUC |
| 1304 | 46 | CACUUAACGCUGAUGAGGCCGAAAGGCCGAAAUUGAUAUCU |
| 1380a | 47 | GUAGGUCUGAUGAGGCCGAAAGGCCGAAAUGUAAUUU |
| 1380b | 48 | GUAGGUCUGAUGAGGCCGAAAGGCCGAAAUGUAAUUUU |
| 1380c | 49 | GGUAGGUCUGAUGAGGCCGAAAGGCCGAAAUGUAAUUUUAU |
| 1380d | 50 | GGUAGGUCUGAUGAGGCCGAAAGGCCGAAAUGUAAUUUUAUU |
| 1419 | 51 | UGAGAUCUGAUGAGGCCGAAAGGCCGAAACGCA |
| 1424 | 52 | AAAGGCUCUGAUGAGGCCGAAAGGCCGAAAGAUGAC |
| 1686 | 53 | GACAGACCUGAUGAGGCCGAAAGGCCGAAAACGAAACA |
| 1680 | 54 | GGACACUGAUGAGGCCGAAAGGCCGAAACGAAC |

TABLE V

Non-limiting examples of ATAL Target Sequences

| Identifier | SEQ ID NO. | Target Sequence |
|---|---|---|
| 262 | 55 | GGUUGGUcAAAAAAGGG |
| 813 | 56 | UCGCCUUcUCCCAC |
| 1182 | 57 | CAGAGUcAUUGUUUAU |
| 1185 | 58 | GAGUCAUuGUUUAUGUG |
| 1304 | 59 | AGAUAUCAAUcCGUUAAGUG |
| 1380a | 60 | AAAUUACAUcACCUAC |
| 1380b | 61 | AAAAUUACAUcACCUAC |
| 1380c | 62 | AUAAAAUUACAUcACCUACC |
| 1380d | 63 | AAUAAAAUUACAUcACCUACC |
| 1419 | 64 | UGCGUcAUCUCA |
| 1424 | 65 | GUCAUCUcAGCCUUU |
| 1686 | 66 | UGUUUCGUUcGUCUGUC |
| 1680 | 67 | GUUCGUcUGUCC |

It should be appreciated that, in some embodiments, the ribozymes and corresponding target sequences listed in Tables IV and V, respectively, are non-limiting and may be used to illustrate a general strategy for targeting ATAL. For example, in some embodiments, ATAL-targeting ribozyme sequences differing from those listed in Table IV can be designed to target the ATAL target sequences listed in Table V (e.g., by using a hybridization sequence overlapping with one or more of the sequences listed in Table IV). In yet other embodiments, alternative ATAL target sequences can be identified by any suitable means, whereupon an ATAL-targeting nucleic acid (e.g., ATAL-targeting ribozyme) can be appropriately designed to hybridize with ATAL.

Several physical parameters were determined by computational methods for each ATAL-targeting sequence in order to evaluate the ribozymes and are listed in Table VI. Computational techniques that can be used to reproduce these calculations and conduct similar analyses are known in the art (e.g., the parameters shown were calculated using ALADDIN, "SeArch computing tooL for hAmmerheaD ribozyme DesIgN"; see Mercatanti, A., et al. (2012) Methods Mol. Bio. 848:337-356; Kharma, N., et al. (2016) Nucleic Acids Res. 44(4): e39). In some embodiments, the ATAL ribozyme folds with a delta G value of between about −13.0 kcal/mol and about −10.0 kcal/mol. In some embodiments, the left and right arms of the ATAL ribozyme bind to a target sequence with a comparable delta G value. For example, as shown in Table VI, the ATAL ribozyme binds to a left substrate binding domain (LSBD) and a right substrate binding domain (RSBD) of a target sequence with comparable delta G values. In some embodiments, the difference between LSBD and RSBD is less than 1.5 kcal/mol (e.g., approximately 0.0, 0.1, 0.2, 0.3, 0.4, 0.5, 0.6, 0.7, 0.8, 0.9, 1.0, 1.1, 1.2, 1.3, 1.4, or 1.5 kcal/mol). In some embodiments, the ATAL ribozyme is characterized by a folding score of at least 0.80. In some embodiments, the ATAL ribozyme is characterized by a folding score of between about 0.80 and about 1.0. In some embodiments, the folding score is between about 0.90 and about 1.0 (e.g., a folding value of approximately 0.90, 0.91, 0.92, 0.93, 0.94, 0.95, 0.96, 0.97, 0.98, 0.99, or 1.0).

TABLE VI

Non-limiting examples of ATAL Ribozyme Properties

| Identifier | NUX | LSBD | RSBD | L Accessibility | R Accessibility | L Uniqueness | R Uniqueness | Delta G | Folding Score |
|---|---|---|---|---|---|---|---|---|---|
| 262 | GUC | −14 | −13.2 | 42 | 66 | — | — | −11.3 | 0.97 |
| 813 | UUC | −14.5 | −13.3 | 72.2 | 99.7 | — | 355 (97.1%) | −11.9 | 0.84 |
| 1182 | GUC | −10.9 | −10.5 | 56.5 | 55.5 | — | — | −11.3 | 0.98 |
| 1185 | AUU | −12.3 | −12.8 | 59.6 | 37.8 | — | — | −11.3 | 0.94 |
| 1304 | AUC | −14.5 | −14.1 | 50 | 55.6 | — | — | −11.5 | 0.85 |
| 1380a | AUC | −10.5 | 11.1 | 66.7 | 66.7 | — | — | −11.3 | 0.97 |
| 1380b | AUC | −11.4 | 11.1 | 70 | 66.7 | — | — | −11.3 | 0.97 |
| 1380c | AUC | −13.8 | −14.4 | 75 | 71.4 | — | — | −11.3 | 0.98 |
| 1380d | AUC | −14.7 | −14.4 | 76.9 | 71.4 | — | — | −11.3 | 0.98 |
| 1419 | GUC | −10.1 | −10.1 | 36.4 | 44.7 | — | — | −11.3 | 1 |
| 1424 | CUC | −12.3 | −12.7 | 66.43 | 51.6 | — | — | −12.6 | 0.73 |
| 1686 | UUC | −14 | −13.4 | 77.8 | 100 | — | — | −11.3 | 1 |
| 1680 | GUC | −10.1 | −10 | 100 | 100 | — | 372 (40%) | −11.3 | 0.81 |

It should be appreciated that, in some embodiments, the examples described above are illustrative of general strategies that can be used by one skilled in the art to design a nucleic acid (e.g., a ribozyme) that targets one or more of the latency-associated region transcripts described herein (e.g., one or more of a LAT, a TAL, or an ATAL gene transcript). For example, the nucleic acid can be designed based on one or more of SEQ ID NOs: 15-17 (e.g., based on one or more transcripts encoded by one or more of SEQ ID NOs: 15-17). One skilled in the art will understand, however, that these example sequences do not limit the scope of the application, and that homologous transcripts in viruses other than HSV-1 could be targeted for cleavage in a similar manner based on this disclosure. Similarly, the example of the codons selected for targeting does not limit the scope of this application, and one skilled in the art will appreciate that other codons could have been selected and addressed with a specific, rationally-designed ribozyme, following the teachings of this application.

In some embodiments, the nucleic acid (e.g., the ribozyme) is complementary to one or more RNA molecules encoded by one or more of SEQ ID NOs: 15-17. In some embodiments, the ribozyme comprises a nucleic acid having a catalytic core flanked by left and right binding arms that hybridize with a target sequence (e.g., as depicted in FIGS. 8B and 8C). In some embodiments, the left and right binding arms each independently comprise at least 4 nucleotides. In some embodiments, the left and right binding arms each independently comprise between 4 and 15 nucleotides (e.g., each arm comprises 4, 5, 6, 7, 8, 9, 10, 11, 12, 13, 14, or 15 nucleotides). In some embodiments, the left and right binding arms are complementary to one or more RNA molecules encoded by one or more of SEQ ID NOs: 15-17. In some embodiments, the left and right binding arms are each independently at least 80% complementary to one or more RNA molecules encoded by one or more of SEQ ID NOs: 15-17 (e.g., at least 80%, at least 85%, at least 90%, at least 95%, at least 96%, at least 97%, at least 98%, at least 99%, or 100% complementary).

In some embodiments, a transcript (e.g., a LAT, a TAL, or an ATAL gene transcript, or any combination of two or more thereof) of one or more of the following non-limiting viruses can be targeted: herpes simplex virus-1 (HHV-1), herpes simplex virus-2 (HHV-2), Varicella zoster virus (HHV-3), Epstein-Barr virus (HHV-4), Cytomegalovirus (HHV-5), Roseolovirus (HHV-6), HHV-7, and Kaposi's sarcoma-associated herpesvirus (HHV-8). In some embodiments, the Kaposi's sarcoma-associated herpesvirus is targeted at its latency-associated nuclear antigen (LANA). In some embodiments, the Epstein-Barr virus is targeted at Epstein-Barr virus (EBV)-encoded small RNAs (EBERs).

Alternatively or in addition to the targeting nucleic acids (e.g., ribozymes) described herein, the AAV particles of the disclosure can be used to target underlying HSV latency mechanisms by delivering repressors of genome editing machinery. For example, in some embodiments, an rAAV particle described herein can be used to deliver genome editing machinery, such as a Cas9 endonuclease and/or a transcription activator-like effector nuclease (TALEN). In certain embodiments, DNA endonucleases and/or other components of the genome editing systems, such as guide RNAs in the case of Cas9 genome editing, are encoded by RNAs or modified RNAs introduced into the cells. Descriptions of various CRISPR-Cas systems for use in gene editing can be found, e.g., in WO2013/176772, and in Nature Biotechnology 32, 347-355 (2014), and references cited therein. A variety of TALEN-based systems have been described in the art (see, e.g., Boch, Science 326(5959): 1509-12 (2009); Mak et al., Science 335(6069):716-9 (2012); and Moscou et al., Science 326(5959):1501 (2009)).

In some embodiments, a subject is a human subject. In some embodiments, a subject is a mammal (e.g., a rodent, a non-human primate, or other mammal). Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. Other non-limiting examples of subjects include domesticated animals such as dogs and cats; livestock such as horses, cows, pigs, sheep, goats, and chickens; and other animals such as mice, rats, guinea pigs, rabbits, and hamsters. In some embodiments, a subject (e.g., a human or other mammal) has, or is diagnosed as having a neurological disease or disorder, and/or an infection of neural cells or tissue (e.g., in the CNS and/or PNS).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Adeno-Associated Virus Vectors Efficiently Transduce Mouse and Rabbit Sensory Neurons Co-Infected with HSV-1 Following Peripheral Inoculation Following infection of epithelial tissues, Herpes Simplex Virus type 1 (HSV-1) virions travel via axonal transport to sensory ganglia and establish a lifelong latent infection within neurons. Recent studies have revealed that, following intraganglionic or intrathecal injection, recombinant adeno-associated virus (rAAV) vectors can also infect sensory neurons and are capable of stable, long-term transgene expression. Whether application of rAAV to peripheral nerve termini at the epithelial surface would allow rAAV to traffic to sensory ganglia in a manner similar to HSV was determined. It was determined whether footpad or ocular inoculation with rAAV8 would results in transduction of dorsal root ganglia (DRG) or trigeminal ganglia (TG), respectively. Footpads of mice were inoculated with varying amounts of rAAV as well as rAAV having capsid mutations. This method of inoculation can achieve transduction of >90% of the sensory neurons in the DRG that innervate the footpad. Similarly, corneal inoculation with rAAV vectors in the rabbit efficiently transduces >70% of the TG neurons in the optic tract. Finally, co-infection of mouse footpads or rabbit eyes with rAAV vectors and HSV-1 was shown to result in co-localization in nearly all of the HSV-1-positive neurons. These results suggest that rAAV is a useful tool for the study of HSV-1 infection and may provide a means to deliver therapeutic cargos for the treatment of HSV or sensory ganglia dysfunctions.

Adeno-associated virus (AAV) has been shown to transduce dorsal root ganglia sensory neurons following direct intraganglionic sciatic nerve injection, intraperitoneal and intravenous injection, as well as intrathecal injection. Whether rAAV vectors would be delivered to the same sensory neurons that herpes simplex virus (HSV-1) infects when applied peripherally, at an epithelial surface that has been treated to expose the underlying sensory nerve termini was examined. For this study, two well-established HSV-1 infection models were chosen: mouse footpad and rabbit ocular infection. The results presented here provide the first description of AAV vectors transducing neurons following delivery at the skin/epithelium/eye. The ability of AAV to co-transduce HSV-1 infected neurons both in the mouse and rabbit opens the opportunity to experimentally explore and disrupt host and viral proteins that are integral to the establishment of HSV-1 latency, to the maintenance of latency and to reactivation from latency in vivo.

Herpes Simplex Virus type 1 (HSV-1) establishes a life-long latent infection within the neurons of sensory ganglia. These ganglia are highly specialized structures composed of a diverse assemblage of neuronal and non-neuronal cells. Ganglionic neurons detect a wide variety of sensory inputs, including temperature, touch, and pain, and relay this information into the central nervous system (CNS). Immunohistochemical analyses of infected trigeminal ganglia (TG) indicate that HSV-1 preferentially establishes latency within certain neuronal subpopulations (1, 2). Historically, such studies have required the use of animal models, such as the rabbit eye to establish latent infections in TG neurons or the mouse footpad infection to establish latent infection in dorsal root ganglia (DRG) neurons. However, the fact that HSV-1 establishes latency within a heterogeneous population of cells with such a complex anatomical structure often makes mechanistic studies of HSV-1 latency challenging. In addition, the fact that most latency experiments are performed in in vivo models, and there are no good techniques to deliver RNA or plasmids to the sensory ganglia in vivo, makes it virtually impossible to use standard techniques such as siRNA knock-downs or over-expression of proteins to study gene function.

In an effort to overcome some of these challenges, a viral vector approach as a gene delivery method into sensory neurons was employed. Many features of adeno-associated virus (AAV) make it an ideal choice for this application. rAAV vectors are widely considered to be non-pathogenic, can infect a wide variety of cell types, and are capable of long-term gene expression in non-mitotic, terminally differentiated cells (3, 4). These vectors have a transgene carrying capacity of about 4.5 kb within their single stranded DNA genomes, however single-stranded AAV (ssAAV) genomes require second strand synthesis before the transgene can be transcribed, effectively slowing the onset of transgene expression (5, 6). To overcome this limitation, modified self-complementary (scAAV) genomes have been generated (7). These genomes encode a half-size genome dimer that base pairs to form a double-stranded DNA template that does not require second-strand synthesis. The cost of this modification is that the transgene capacity is reduced by half, although this is still ample space for promoters and ORFs encoding small interfering RNAs, as well as relatively small reporter genes such as GFP.

In addition to modifications of the genome which allow for more efficient transgene expression, the AAV capsid proteins can also be modified to allow for greater transduction efficiency, as capsid serotype is a major determinant of cell tropism (8). New serotypes are constantly being discovered or engineered and tested for efficacy in cell culture and animal models of disease (9, 10). Studies of intracellular vector trafficking revealed that phosphorylation of exposed tyrosine residues on the AAV capsid surface leads to vector degradation and reduced transgene expression (11). When certain capsid tyrosine residues were mutated to phenylalanine (e.g., Y733F), transduction efficiency was shown to be greatly increased relative to vectors with wild type capsids (12-20). AAV is capable of transducing DRG sensory neurons via direct intraganglionic sciatic nerve injection (21, 22), intraperitoneal and intravenous injection (23), as well as intrathecal injection following lumbar puncture (24-27). Whether rAAV vectors would be delivered to the same sensory neurons that HSV-1 infects when applied at an epithelial surface that has been treated to expose the underlying sensory nerve termini was examined. For this study, two well-established HSV-1 infection models were selected: mouse footpad and rabbit ocular infection. The efficacy of delivery of several different types of rAAV vectors, including ssAAV and scAAV, as well as tyrosine capsid mutants were also compared. The results presented here provide the first description of AAV vectors transducing neurons following delivery at the skin/epithelium.

Results rAAV vectors transduce a high percentage of murine DRG neurons. To determine if recombinant AAV vectors could transduce DRG sensory neurons following application of virus at the abraded epidermis, mouse footpads were inoculated with several different types of rAAV vectors. Mice were sacrificed at 4 and 14 dpi and DRG were analyzed by immunohistochemistry (IHC) for AAV reporter gene (GFP) expression (FIG. 1). All AAV-transduced ganglia exhibited brown DAB staining, indicating the presence of GFP. Staining was not apparent in tissues infected with KOS/62 alone (FIG. 1B). Tissue sections that did not receive primary anti-GFP antibody also had no apparent staining (FIGS. 1D, 1F, 1H). These data suggest that the staining is specific for GFP expression and that the rAAV vectors did indeed transduce DRG sensory neurons following external application. Counts of stained neurons indicated that nearly all sensory neurons were transduced.

Figure 2A:
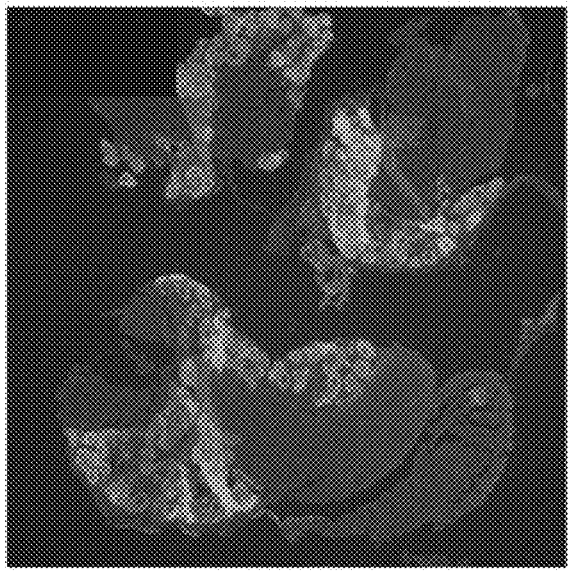
FIGS. 2A-2D show that single color immunofluorescence detects both rAAV8 and HSV-1 in mouse DRG.
Figure 2B:
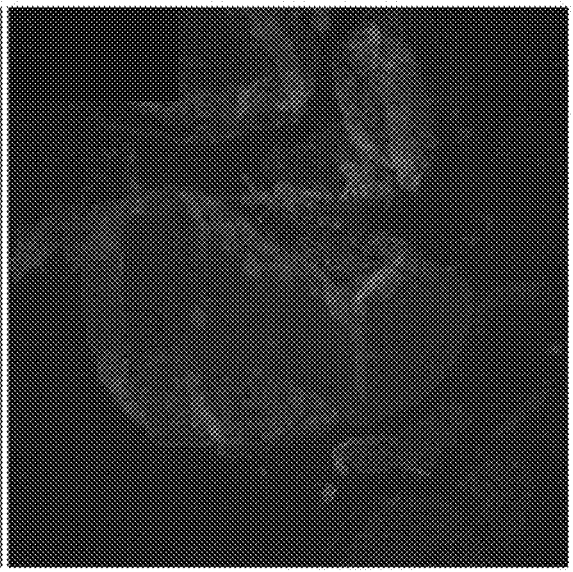
Figure 2C:
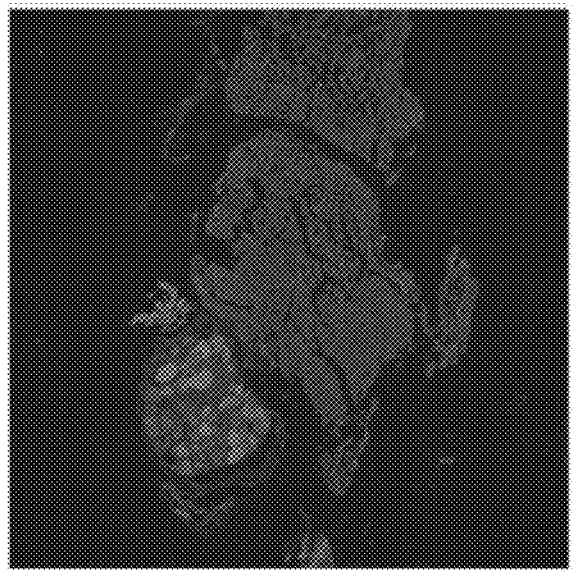
Figure 2D:
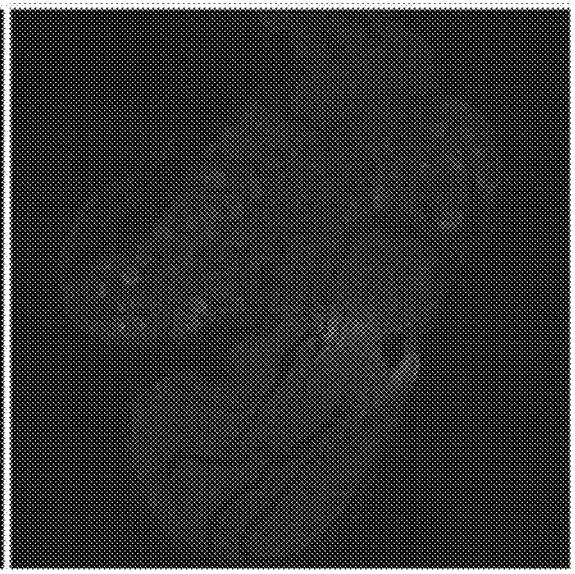
Figure 3A:
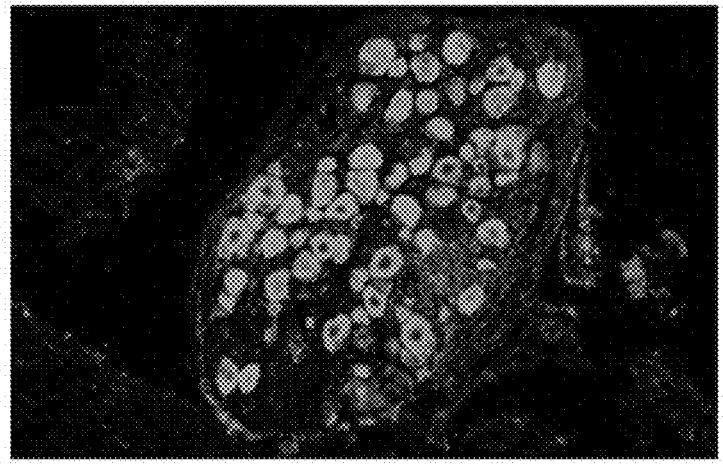
FIGS. 3A-3C show dual-color immunofluorescence demonstrating co-localization of rAAV8 and HSV-1 within a subset of sensory neurons in mouse DRG. Mice were infected with both $10^{10}$ particles of scAAV-GFP-WT and 5000 PFU of KOS/62. DRG were harvested 4 dpi. Tissue sections were incubated with both anti-GFP and anti-β-gal primary antibodies.
Figure 3B:
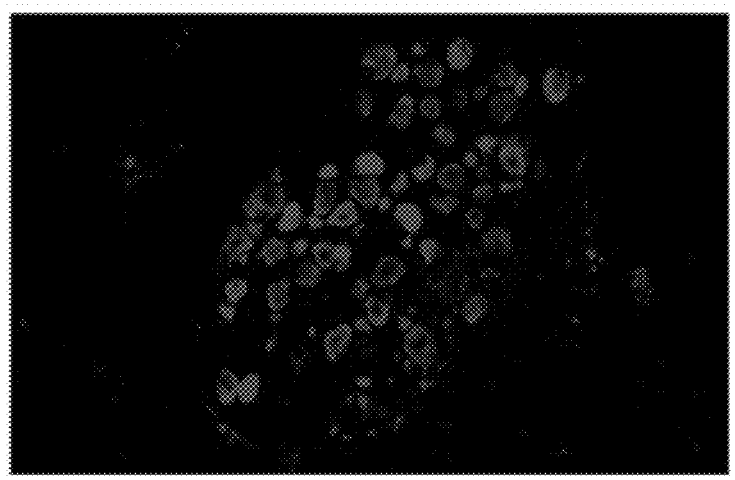
Figure 3C:
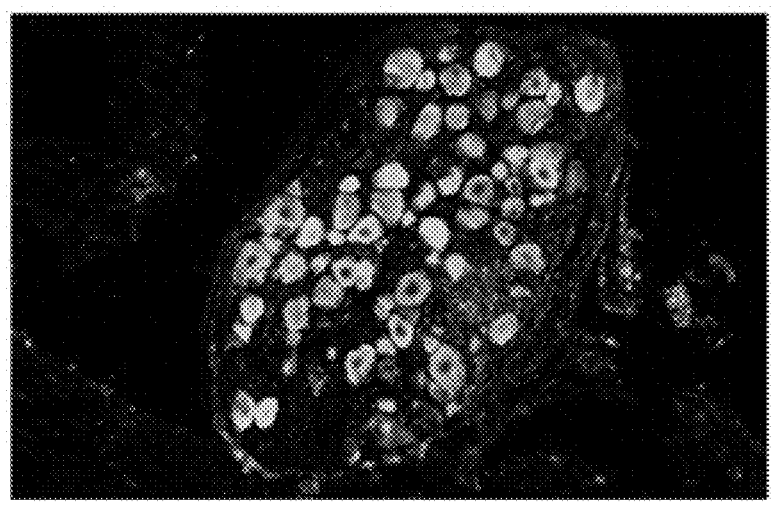
Figure 4A:
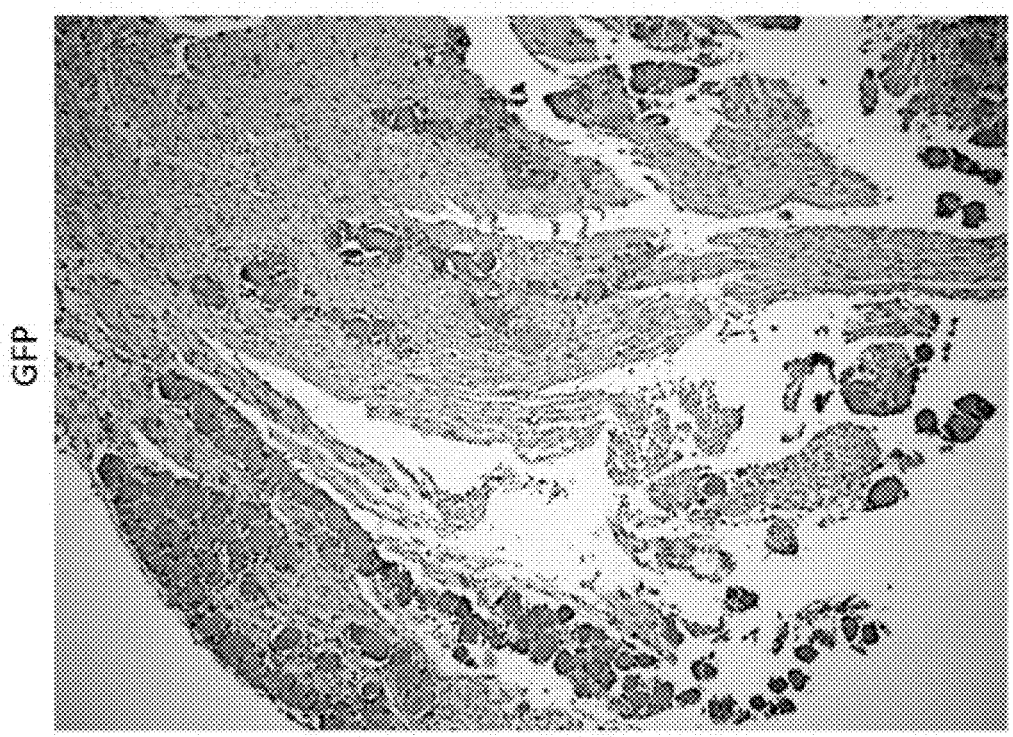
FIGS. 4A-4B show immunohistochemistry on rabbit TGs following corneal delivery of AAV8-GFP capsid mutant confirms AAV8 efficiently transduces neurons through a corneal route of delivery. Immunohistochemistry was done using rabbit TG following corneal inoculation with ssAAV8-GFP-Y733. All TG were harvested on post-inoculation day 16.
Figure 4B:
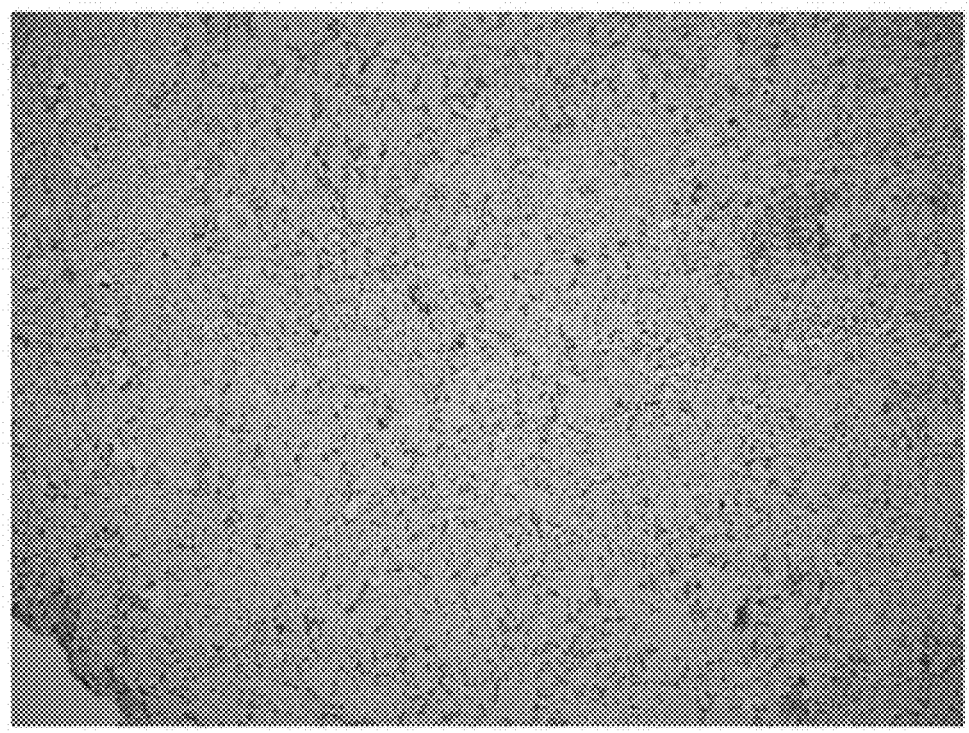
Figure 5:
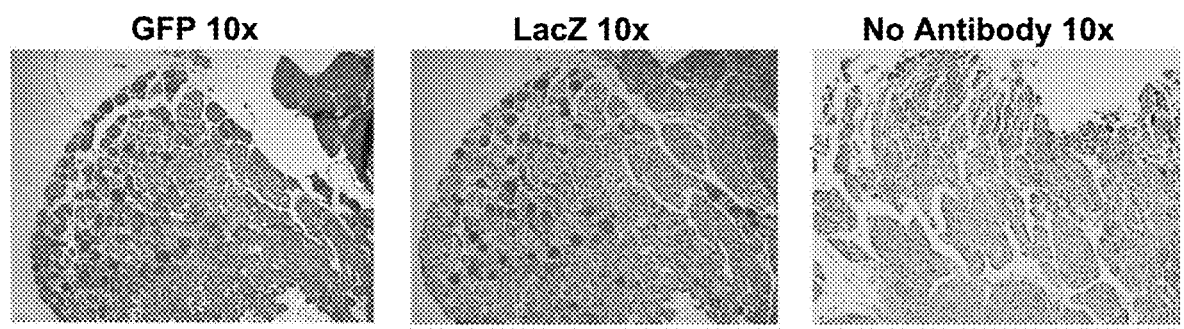
FIG. 5 shows immunohistochemistry using rabbit TGs following corneal delivery of ssAAV8-GFP-Y733 and a KOS/62 demonstrates co-localization of both the vector and HSV-1 in sensory neurons. Serial sections of TG from rabbits inoculated with ssAAV8-GFP-Y733 and KOS/62 were used to demonstrate that the vector and HSV-1 co-localize in neurons. Serial sections of <5 microns are presented at 10× magnifications. IHC to detect the presence of KOS/62 was done using a mouse anti-β-galactosidase primary (Abcam), followed by a biotinylated HRP secondary (Vector Labs). To detect AAV8-GFP in neurons, sections were incubated with mouse anti-GFP (Abcam), followed by incubation with a biotinylated HRP secondary (Vector Labs). IHC was done to detect either HSV-1 or AAV8 using serial sections to demonstrate that neurons harbor both the vector and the virus. Control slides were prepared from co-infected rabbit TG, subjected to IHC with no primary antibody.
Figure 6:
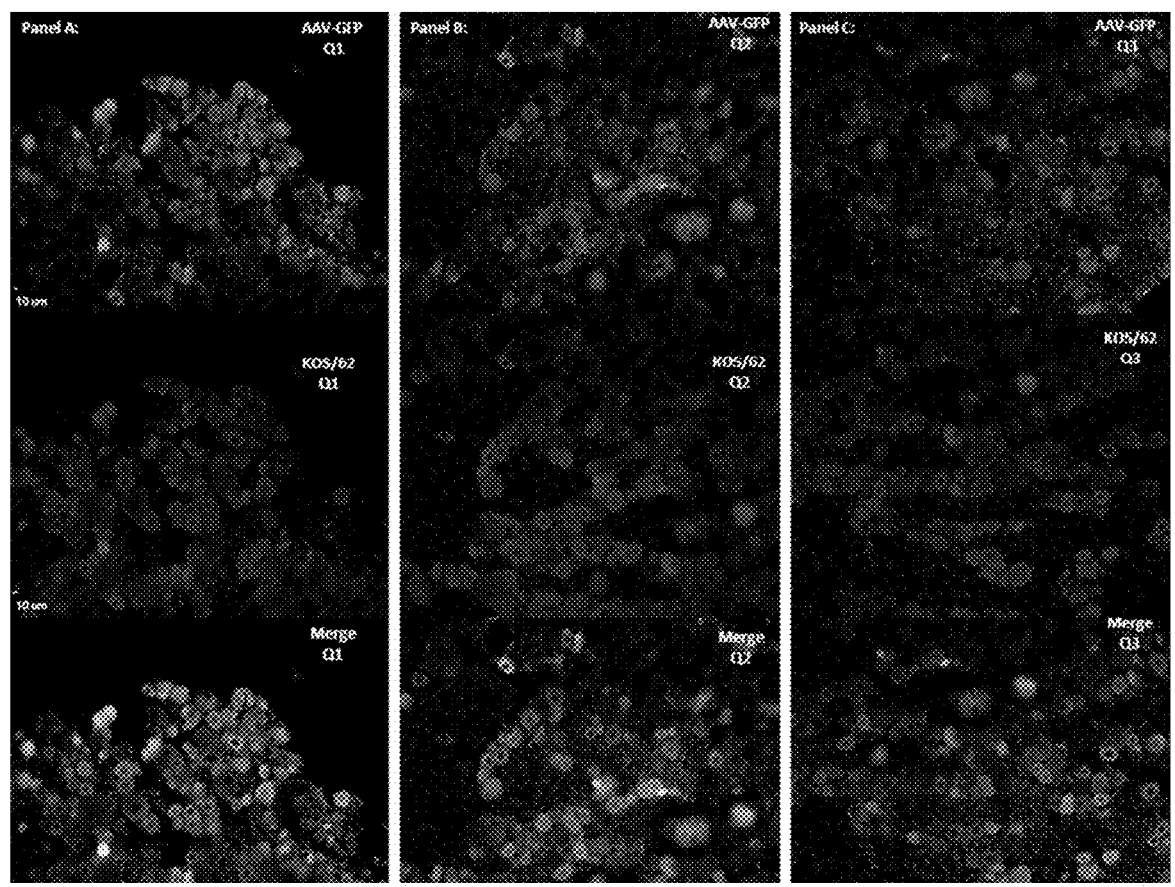
FIG. 6 shows immunofluorescence demonstrating long-term expression and co-localization of AAV8-GFP and KOS/62 in co-infected rabbit TG. IF was performed to demonstrate neuronal co-localization of vector and virus. Sections were incubated with either mouse anti-GFP or mouse anti-β-galactosidase primary antibodies. AlexaFluor 548 (Invitrogen) or goat anti-mouse AlexaFluor 488 (Invitrogen) were used as secondary antibodies for immunofluorescent visualization using a Leica de-convolution microscope with Slidebook 5.0. The TG section on the slide was divided into three equal quadrants (Q1-3, Panels A-C) to represent the co-localization of virus and vector over the entire TG cross-section. DAPI staining in blue represents nuclei of satellite cells present in the sections. All images are 10×.

Modified capsids increase transduction efficiency. Regardless of the rAAV vector used for infection, the percentage of stained neurons was the same across treatment groups. However, staining intensity was notably different depending upon the type of genome (single-stranded vs. self-complementary). Staining intensity was greater at 4 dpi for scAAV (FIG. 1C) than at 14 dpi for ssAAV (FIG. 1A). Moreover, staining intensity was affected by the type of capsid (wild-type vs. Y733F mutation). Sections of tissue infected with $10^9$ vg scAAV with the mutant capsid (FIG. 1E) had similar levels of expression compared to sections of tissue infected with $10^{10}$ vg scAAV with wild-type capsids (FIG. 1C). The most intense staining was observed in sections from tissue infected with $10^{10}$ vg scAAV8-GFP-Y733F (FIG. 1G). While staining intensity is not a perfect quantitative measure of reporter gene expression, the results strongly suggest that use of modified capsids will be beneficial in further experiments.

rAAV vectors and HSV-1 co-infect murine sensory neurons. To determine if the rAAV vectors were capable of transducing HSV-1 infected DRG neurons, mouse footpads were co-infected and DRG and were harvested for IF analysis. Similar to IHC results, GFP expression from AAV vectors was widespread within neurons (FIG. 2A). β-gal expression from KOS/62 was limited to a smaller subset of neurons (FIG. 2C). This result is consistent with previous findings demonstrating that not all DRG neurons are infected with HSV-1 following mouse footpad infection (28). Co-localization was observed in those neurons expressing β-gal (FIG. 3). Tissues transduced with rAAV8 alone did not stain for β-gal, and conversely tissues infected with HSV-1 alone did not stain for GFP. Tissue sections not receiving primary antibodies displayed only non-specific background fluorescence, demonstrating that antibody binding was specific for the intended targets, the GFP and β-gal reporters (FIGS. 2B, 2D).

rAAV vectors transduce a high percentage of rabbit TG neurons. Based on the efficiency of delivery of rAAV to the murine DRG via footpad delivery, this concept was extended to the HSV-1 ocular infection model. HSV-1 infection of mouse eyes is commonly used to study latency in the TG neurons, but the rabbit ocular model provides a robust model of induced reactivation. Therefore, whether corneal delivery of AAV might transduce TG neurons was examined. Rabbit eyes were abraded and the ssAAV8-GFP-Y733 vector applied to the corneas. Seventeen days post-inoculation, the TG were harvested and tissue sections stained with an anti-GFP antibody to assess AAV reporter gene (GFP) expression (FIG. 4). Regions of neurons in the TG corresponding to the ophthalmic branch of the trigeminal nerve exhibited DAB staining indicating the presence of GFP (FIG. 4), whereas neurons innervated by other branches of the TG and the untreated control did not. While a large number of neurons in this region stained for GFP, the number of transduced neurons approached 70%, as compared with the >90% seen in the murine DRG. The difference may reflect less efficient delivery to the sensory neuron fibers of the cornea than to the sensory nerve termini of the mouse footpad. Nevertheless, these results demonstrate that the AAV vector efficiently transduces the neurons in the ophthalmic branch following delivery to the cornea.

rAAV vectors and HSV-1 co-infect rabbit sensory neurons. In order to determine if rAAV could transduce HSV-1 infected neurons in the rabbit TG as it did in the mouse, the ssAAV-GFP-Y733 vector was applied to the rabbit cornea at the same time as the HSV-1 lacZ recombinant, KOS/62. At 28 days post treatment/infection, DAB staining for either GFP or lacZ demonstrate a large number of neurons infected with HSV and transduced with AAV (FIG. 5).

rAAV vectors display sustained expression in the co-infected rabbit sensory neurons. In order to more directly assess the co-localization of AAV transduced neurons with HSV infected ones and to establish long-term AAV expression in latently infected rabbits, ssAAV-GFP-Y733 was applied to the surface of the rabbit cornea at a titer of $1 \times 10^{10}$ vg/eye. The eyes were infected with KOS/62 17 days after AAV application. Rabbits were allowed to establish a latent infection (~30 days post-KOS/62 infection). TG were harvested and indirect immunofluorescence analyses of the same sections stained for both GFP and β-galactosidase were performed (FIG. 6). These results clearly demonstrate the presence of AAV-driven GFP expression in the majority of the same neurons that are expressing lacZ from the HSV-1 recombinant. It is striking that while the AAV does not transduce as high of a percentage of the neurons in the TG as was seen in the murine DRG, the majority of HSV-1 infected neurons also are transduced by AAV, suggesting that these neurons were accessible to both viruses at the site of infection, or that there is a shared propensity of these neurons for the transgene expression. These results demonstrate the ability of AAV to efficiently transduce TG neurons when applied to the treated eye surface, and that it is possible to efficiently transduce HSV infected neurons with this vector. Furthermore, this result confirms stable AAV expression at 6 weeks post treatment.

The ability to knockdown or augment cellular and viral gene products within sensory neurons would be invaluable to the study of HSV-1 latency. HSV-1 does not establish latency in standard tissue culture lines, and in vitro models of latency are only in early stages of development. Studies of the mechanisms silencing viral lytic gene expression will require in vivo animal models, in which it is difficult or impossible to perform techniques such as transfections or knockdowns. The primary aim of the experiments described here was to develop a method of performing these experiments in vivo.

Results of IHC experiments demonstrate that, following footpad inoculation, AAV vectors transduce DRG sensory neurons (FIG. 1). rAAV application at the foot, or peripheral epithelium, innervated by the DRG, or the eye innervated by the TG, has not been previously demonstrated. Axonal transport of AAV is serotype-dependent in the CNS (30, 31), and AAV9 transport following brain injection is driven by cytoplasmic dynein and kinesin proteins (32). AAV8 selectively transduces sensory neurons, but not motor neurons, in the PNS (23). It is likely that the vectors enter the neurons at nerve termini and are trafficked to cell bodies using the same transport machinery as HSV-1, and this conclusion is supported by the present findings. Most neurons stained positive for GFP expression, indicating that AAV8 did not preferentially infect any particular neuronal subtype. Expression from scAAV vectors was detected at 4 dpi, and staining intensity was greater than that observed from ssAAV vectors at 14 dpi. It was inferred that the self-complementary genomes bypassed the usual rate-limiting step of second-strand synthesis, resulting in earlier transgene turn-on. Staining intensity increased with dose and was also affected by capsid type. Consistent with previous reports of capsid tyrosine mutants (16, 17), the Y733F single mutation resulted in an approximately 10-fold increase in transduction efficiency. Additional studies were performed in the rabbit ocular model to ensure that co-infection/application of the AAV vector with virulent strains of HSV-1 does not enhance corneal lesions during the acute infection, or alter the HSV-1 reactivation efficiency of strain 17syn+. Neither corneal lesion score nor reactivation frequency was altered by the co-application of the AAV vector (data not shown).

Results of IF experiments indicate that, after application to the mouse footpad or rabbit cornea, AAV and HSV-1 co-infect the same DRG sensory neurons. From these data it was concluded that AAV is an effective gene delivery vector for sensory neurons and can be delivered efficiently from the periphery, making it a very useful tool for in vivo studies of not only HSV-1 latency, but also reactivation from latency as well. Further studies using AAV to deliver shRNA or to express other gene products such as signaling pathway agonists or chromatin modifiers will allow one to test this methodology in the relevant in vivo models, targeting genes or proteins in neurons that are co-localized with the AAV vector, rather than globally inhibiting or up-regulating gene expression. In some embodiments, these AAV vectors provide a useful tool to target HSV latency itself by delivering repressors or genome editing machinery such as TALENs or CRISPR-Cas9.

Materials and Methods

Viruses and cells. For co-localization, immunofluorescence (IF) and immunohistochemistry (IHC) were performed on dorsal root ganglia (DRG) sections from mice infected with either HSV-1 or rAAV vectors, or both. KOS/62, an avirulent HSV-1 LAT-recombinant that expresses β-gal from the LAT loci (28, 29), was used for co-localization. KOS/62 was grown and titered on rabbit skin cells using Eagle's minimal essential medium (Life Technologies) supplemented with 5% bovine serum, 250 U penicillin/mL, 250 μg streptomycin/mL, and 292 μg L-glutamine/mL (Life Technologies). A variety of rAAV vectors were used, including single stranded (ssAAV), self-complementary (scAAV), and with wild-type (WT) or modified capsids (Y733F) (11). All rAAV vectors expressed GFP driven by a chicken β-actin promoter and CMV immediate early enhancer and diluted in saline.

Mouse footpad infections. Six-week-old female ND4 Swiss mice were anesthetized with isoflurane and subcutaneously injected with 50 μL of a 10% sterile saline solution into both rear footpads. Three hours after saline treatment, mice were anesthetized by intramuscular injection of 20 μL of a cocktail of ketamine (30 to 45 mg/kg of body weight), xylazine (7.5 to 11.5 mg/kg), and acepromazine (2.5 to 3.75 mg/kg). Both rear footpads were abraded with an emery board to remove the keratinized epithelium. A total volume of 50 μL of virus per mouse was applied to the exposed dermis, and virus was allowed to adsorb for one hour while mice remained under anesthesia. Composition of the applied virus varied by treatment group as described below.

Treatment groups for co-localization experiments. Groups A-C were infected as shown and were sacrificed at 14 dpi. Groups D-G were sacrificed at 4 dpi.

Group A: $10^{10}$ viral genomes (vg) ssAAV8-GFP-WT only
Group B: 5000 PFU KOS/62 only
Group C: 5000 PFU KOS/62+$10^{10}$ vg ssAAV8-GFP-WT
Group D: 5000 PFU KOS/62+$10^{10}$ vg scAAV8-GFP-WT
Group E: 5000 PFU KOS/62+$10^{10}$ vg scAAV8-GFP-Y733F
Group F: 5000 PFU KOS/62+$10^{9}$ vg scAAV8-GFP-Y733F
Group G: 5000 PFU KOS/62+$10^{8}$ vg scAAV8-GFP-Y733F Rabbit ocular infections: New Zealand White rabbits were anesthetized using intramuscular injections of ketamine (30-45 mg/kg body weight) and xylazine (7.5-11.5 mg/kg body weight). Using a blunt-tip 27-gauge needle, a 3 by 3 crosshatch pattern was made on the corneal surface. ssAAV8-GFP-Y733 was applied to each eye at an initial inoculum of $1\times10^{10}$ viral genome equivalents(vg)/eye in a total volume of 20 μl. For co-infections with ssAAV8-GFP-Y733 and KOS/62, rabbits first received ssAAV8-GFP-Y733 at a titer of $1\times10^{10}$ vg/eye followed by re-scarification of the corneal surface and infection with KOS/62 at a titer of 200,000 pfu/eye (20 μl) 17 days following the application of AAV to the corneal surface. Mice were euthanized by isoflurane overdose, and death was ensured by cervical dislocation. For co-infected rabbits, rabbits were anesthetized with ketamine and then euthanized using an overdose of pentobarbital and ganglia were harvested at 31 days following the KOS infection. Prior to euthanasia, all rabbits underwent slit lamp examination to ensure no ocular lesions remained. Controls for experiments were either naïve rabbits or rabbits latent with HSV-1 strain KOS/62.

Mouse DRG tissue processing/sectioning. At the appropriate day after infection, mice were deeply anesthetized by intramuscular injection of 40 μL of a cocktail of ketamine (60 to 90 mg/kg of body weight), xylazine (15 to 23 mg/kg), and acepromazine (5 to 7.5 mg/kg). Cardiac perfusion was immediately performed with 15 mL of 0.1 M phosphate-buffered saline (PBS, pH 7.4), followed by 15 mL of 4% paraformaldehyde (PFA) in 0.1 M phosphate buffer (PB, pH 7.4). DRG from each mouse were fixed in ice-cold 4% PFA for one hour and then transferred to 70% ethanol and stored at 4° C. Tissue was dehydrated in a graded series of ethanol baths and xylene, embedded in paraffin, and 6 μm sections prepared and applied to glass microscope slides.

Rabbit TG tissue processing/sectioning. Immediately upon removal, TGs were placed in 10% neutral buffered formalin, stored at 4° C. overnight, and then transferred to 70% ethanol. All samples were then paraffin embedded and serial sectioned to 10 microns in thickness with 3-4 sections per each slide.

Dual-immunofluorescence Analysis of AAV/HSV-1 Co-localization in Mouse DRG. Tissue sections were de-paraffinized in xylene and re-hydrated through a graded series of ethanol baths to dd$H_2O$. Antigens that may have been obscured by fixation were exposed by heat-mediated epitope retrieval by heating tissue sections to 90-95° C. for 25 minutes in 0.01 M citrate buffer, pH 6.0. A 1.5% normal goat serum blocking solution (Vector Laboratories) was applied for 20 minutes to prevent non-specific antibody interactions. All incubations were performed in a dark moist chamber. Rabbit anti-GFP and chicken anti-β-galactosidase primary antibodies (Abcam) were incubated on tissue sections overnight at 4° C. at a dilution of 1:200. FITC-labeled goat anti-rabbit IgG (Vector Laboratories) and Texas Red-labeled goat anti-chicken IgG (Abcam) secondary antibodies were applied for 30 minutes at room temperature at dilutions of 1:50 and 1:200, respectively. Sections were washed for 2 minutes in water and then coverslips were mounted with PBS. Sections were washed with TBS-T (1% Tween-20 in Tris HCl-buffered saline, pH 7.5) between all steps. Slides were viewed immediately with a Zeiss Axioskop 2 microscope and dark field fluorescence images were captured using a SPOT digital camera and software package version 1.2.1 (Diagnostic Instruments). Twelve tissue sections from each mouse, each comprising profiles through 1 to 4 ganglia, were analyzed for fluorescence. As a negative control for primary antibody specificity, four sections from each mouse were treated as described, except that no primary antibodies were applied.

Immunohistochemical Analysis of AAV Reporter Gene Expression in Mouse DRG. Tissue sections were de-paraffinized in xylene and re-hydrated, then soaked in a 3% hydrogen peroxide solution in 70% methanol for 10 minutes to block endogenous peroxidase activity. Epitope retrieval was carried out by heating tissue sections to 90-95° C. for 25 minutes in 0.01 M citrate buffer, pH 6.0. A solution of 1.5% normal goat serum and 10% Avidin D (Vector Laboratories) was applied for 20 minutes to prevent non-specific antibody and avidin interactions with tissue. Slides were then placed in a moisture chamber to prevent evaporation of solutions. A solution of 10% biotin (Vector Laboratories) and a 1:1000 dilution of rabbit anti-GFP primary antibody (Abcam) was applied for 1 hour. Further processing was performed with the Vectastain ABC Elite Kit (Vector Laboratories). A biotinylated anti-rabbit secondary antibody was applied for 30 minutes at a dilution of 1:200, followed by incubation with avidin-biotin-conjugated horseradish peroxidase (HRP) enzyme for 30 minutes and finally development of the chromogen substrate 3,3'-diaminobenzidine (DAB) for 8 minutes. All incubations were performed at room temperature and sections were washed with TBS-T between all steps. Tissue sections were counterstained with hematoxylin, dehydrated in a graded series of ethanol baths, and cleared in xylene. Glass coverslips were permanently mounted with Cytoseal XYL (Richard-Allan Scientific). Slides were allowed to dry overnight before viewing with a Zeiss Axioskop 2 microscope. Bright field images were captured using a SPOT digital camera and software package version 1.2.1 (Diagnostic Instruments). Eight tissue sections from each mouse, each comprising profiles through 1 to 4 ganglia, were analyzed for brown DAB staining. Neuron cell bodies were identified by cell morphology and large blue-stained nuclei. The percentage of transduced neurons was calculated by dividing stained neurons by total neurons counted. Staining intensity between treatment groups was observed visually as a measure of reporter gene expression. As a control for primary antibody specificity, two sections from each mouse were treated as described, except that no primary antibody was applied.

Immunohistochemistry-Rabbit TG. Slides containing serial sections of rabbit TG were deparaffinized, hydrated, and peroxidase blocked through a series of washes that included: (1) Two xylene washes for five minutes each, (2) two 100% ethanol washes for 2 minutes each, (3) one 3% hydrogen peroxide wash (30% hydrogen peroxide was diluted 1:10 in 100% methanol) for 10 minutes, (4) one 95% ethanol wash for three minutes, (5) one 70% ethanol wash for one minute, and (6) one ddH$_2$O wash for one minute. Epitope retrieval was done by microwaving the slides in citrate buffer using a Coplin jar that was filled with 10 mM citrate buffer (pH=6.0) and then placed inside a beaker filled with ddH$_2$O. The apparatus was brought to a light boil by microwaving on high for 8 minutes and allowed to sit at room temperature for 25 minutes, so the samples could remain at 90° C. The slides were removed from the citrate buffer, rinsed in water, and washed in TBS-T. A serum and avidin block, followed by a biotin block was performed using normal serum from the species in which the secondary antibody was raised and avidin/biotin (Vector Labs avidin-biotin blocking kit) diluted in Zymed antibody diluent according to the manufacturer's instructions. Sections were then incubated with primary antibody (1:200 of either mouse anti-GFP or mouse anti-β-galactosidase antibody (Abcam) overnight at 4° C., followed by incubation with goat-anti-mouse biotinylated secondary antibody (1:200 dilution in Zymed diluent) at room temperature for 2 hours. Following secondary antibody incubation, slides were developed for IHC using ABC Elite reagent and DAB chromogen substrate according to the manufacturers protocols (Vector Labs). Counterstaining was done with hematoxylin QS (Vector Labs) and then dehydrated and cleared in xylene using another series of washes: one 1-minute water wash, one 1-minute 70% ethanol wash, one 1-minute 95% ethanol wash, two 1-minute 100% ethanol washes, and two 1-minute xylene washes. The slides were then allowed to dry at room temperature and were mounted with VectaMount (Vector Labs). Slides containing 4 serial sections per rabbit (with a total of 5 rabbits per treatment group) were used for each experiment. Sections were imaged on a Zeiss microscope equipped with AxioVision Rel 4.6. Negative controls included either naïve rabbit TG subjected to the full IHC protocol described above with antibody incubation, or rabbit TG latent with KOS/62 subjected to the above described IHC protocol without incubation with the primary antibody.

Immunofluorescence-Rabbit TG. Slides were processed in a manner identical to that described in the immunohistochemistry for rabbit TG section of this manuscript up through primary antibody incubation. Secondary antibody incubation was then performed using 1:1000 goat anti-chicken AlexaFluor 548 (Invitrogen) or 1:1000 goat anti-mouse AlexaFluor 488 (Invitrogen) for 2 hours at room temperature. The slides were mounted using ProLong gold mounting media (Invitrogen) and imaged using a Leica deconvolution microscope equipped with Slidebook 5.0. Five slides per rabbit were subjected to the IF protocol described above, and a total of 5 rabbits per treatment group were used.

References (Example 1)

1. Margolis T P, Dawson C R, LaVail J H. 1992. Herpes simplex viral infection of the mouse trigeminal ganglion. Immunohistochemical analysis of cell populations. Invest Ophthalmol Vis Sci 33:259-267.
2. Yang L, Voytek C C, Margolis T P. 2000. Immunohistochemical analysis of primary sensory neurons latently infected with herpes simplex virus type 1. J Virol 74:209-217.
3. Russell D W, Miller A D, Alexander I E. 1994. Adeno-associated virus vectors preferentially transduce cells in S phase. Proc Natl Acad Sci USA 91:8915-8919.
4. Lovric J, Mano M, Zentilin L, Eulalio A, Zacchigna S, Giacca M. 2012. Terminal differentiation of cardiac and skeletal myocytes induces permissivity to AAV transduction by relieving inhibition imposed by DNA damage response proteins. Mol Ther 20:2087-2097.
5. Ferrari F K, Samulski T, Shenk T, Samulski R J. 1996. Second-strand synthesis is a rate-limiting step for efficient transduction by recombinant adeno-associated virus vectors. J Virol 70:3227-3234.
6. Fisher K J, Gao G P, Weitzman M D, DeMatteo R, Burda J F, Wilson J M. 1996. Transduction with recombinant adeno-associated virus for gene therapy is limited by leading-strand synthesis. J Virol 70:520-532.
7. McCarty D M, Monahan P E, Samulski R J. 2001. Self-complementary recombinant adeno-associated virus (scAAV) vectors promote efficient transduction independently of DNA synthesis. Gene Ther 8:1248-1254.
8. Zincarelli C, Soltys S, Rengo G, Rabinowitz J E. 2008. Analysis of AAV serotypes 1-9 mediated gene expression and tropism in mice after systemic injection. Mol Ther 16:1073-1080.
9. Grieger J C, Samulski R J. 2012. Adeno-associated virus vectorology, manufacturing, and clinical applications. Methods Enzymol 507:229-254.
10. Grimm D, Zolotukhin S. 2015. E Pluribus Unum: 50 Years of Research, Millions of Viruses, and One Goal—Tailored Acceleration of AAV Evolution. Mol Ther 23:1819-1831.
11. Zhong L, Zhao W, Wu J, Li B, Zolotukhin S, Govindasamy L, Agbandje-McKenna M, Srivastava A. 2007. A dual role of EGFR protein tyrosine kinase signaling in ubiquitination of AAV2 capsids and viral second-strand DNA synthesis. Mol Ther 15:1323-1330.
12. Qi Y F, Li Q H, Shenoy V, Zingler M, Jun J Y, Verma A, Katovich M J, Raizada M K. 2013. Comparison of the transduction efficiency of tyrosine-mutant adeno-associated virus serotype vectors in kidney. Clin Exp Pharmacol Physiol 40:53-55.
13. Song L, Li X, Jayandharan G R, Wang Y, Aslanidi G V, Ling C, Zhong L, Gao G, Yoder M C, Ling C, Tan M, Srivastava A. 2013. High-efficiency transduction of primary human hematopoietic stem cells and erythroid lineage-restricted expression by optimized AAV6 serotype vectors in vitro and in a murine xenograft model in vivo. PLoS One 8:e58757.
14. Kay C N, Ryals R C, Aslanidi G V, Min S H, Ruan Q, Sun J, Dyka F M, Kasuga D, Ayala A E, Van Vliet K, Agbandje-McKenna M, Hauswirth W W, Boye S L, Boye S E. 2013. Targeting photoreceptors via intravitreal delivery using novel, capsid-mutated AAV vectors. PLoS One 8:e62097.
15. Dalkara D, Byrne L C, Lee T, Hoffmann N V, Schaffer D V, Flannery J G. 2012. Enhanced gene delivery to the neonatal retina through systemic administration of tyrosine-mutated AAV9. Gene Ther 19:176-181.
16. Li M, Jayandharan G R, Li B, Ling C, Ma W, Srivastava A, Zhong L. 2010. High-efficiency transduction of fibroblasts and mesenchymal stem cells by tyrosine-mutant AAV2 vectors for their potential use in cellular therapy. Hum Gene Ther 21:1527-1543.
17. Markusic D M, Herzog R W, Aslanidi G V, Hoffman B E, Li B, Li M, Jayandharan G R, Ling C, Zolotukhin I, Ma W, Zolotukhin S, Srivastava A, Zhong L. 2010. High-efficiency transduction and correction of murine hemophilia B using AAV2 vectors devoid of multiple surface-exposed tyrosines. Mol Ther 18:2048-2056.
18. Qiao C, Zhang W, Yuan Z, Shin J H, Li J, Jayandharan G R, Zhong L, Srivastava A, Xiao X, Duan D. 2010. Adeno-associated virus serotype 6 capsid tyrosine-to-phenylalanine mutations improve gene transfer to skeletal muscle. Hum Gene Ther 21:1343-1348.
19. Petrs-Silva H, Dinculescu A, Li Q, Min S H, Chiodo V, Pang J J, Zhong L, Zolotukhin S, Srivastava A, Lewin A S, Hauswirth W W. 2009. High-efficiency transduction of the mouse retina by tyrosine-mutant AAV serotype vectors. Mol Ther 17:463-471.
20. Zhong L, Li B, Mah C S, Govindasamy L, Agbandje-McKenna M, Cooper M, Herzog R W, Zolotukhin I, Warrington K H, Jr., Weigel-Van Aken K A, Hobbs J A, Zolotukhin S, Muzyczka N, Srivastava A. 2008. Next generation of adeno-associated virus 2 vectors: point mutations in tyrosines lead to high-efficiency transduction at lower doses. Proc Natl Acad Sci USA 105:7827-7832.
21. Yu H, Fischer G, Hogan Q H. 2016. AAV-Mediated Gene Transfer to Dorsal Root Ganglion. Methods Mol Biol 1382:251-261.
22. Fischer G, Kostic S, Nakai H, Park F, Sapunar D, Yu H, Hogan Q. 2011. Direct injection into the dorsal root ganglion: technical, behavioral, and histological observations. J Neurosci Methods 199:43-55.
23. Foust K D, Poirier A, Pacak C A, Mandel R J, Flotte T R. 2008. Neonatal intraperitoneal or intravenous injections of recombinant adeno-associated virus type 8 transduce dorsal root ganglia and lower motor neurons. Hum Gene Ther 19:61-70.
24. Storek B, Reinhardt M, Wang C, Janssen W G, Harder N M, Banck M S, Morrison J H, Beutler A S. 2008. Sensory neuron targeting by self-complementary AAV8 via lumbar puncture for chronic pain. Proc Natl Acad Sci USA 105:1055-1060.
25. Beutler A S, Banck M S, Walsh C E, Milligan E D. 2005. Intrathecal gene transfer by adeno-associated virus for pain. Curr Opin Mol Ther 7:431-439.
26. Wang X, Wang C, Zeng J, Xu X, Hwang P Y, Yee W C, Ng Y K, Wang S. 2005. Gene transfer to dorsal root ganglia by intrathecal injection: effects on regeneration of peripheral nerves. Mol Ther 12:314-320.
27. Vulchanova L, Schuster D J, Belur L R, Riedl M S, Podetz-Pedersen K M, Kitto K F, Wilcox G L, McIvor R S, Fairbanks C A. 2010. Differential adeno-associated virus mediated gene transfer to sensory neurons following intrathecal delivery by direct lumbar puncture. Mol Pain 6:31.
28. Margolis T P, Sedarati F, Dobson A T, Feldman L T, Stevens J G. 1992. Pathways of viral gene expression during acute neuronal infection with HSV-1. Virology 189:150-160.
29. Sawtell N M, Thompson R L. 1992. Herpes simplex virus type 1 latency-associated transcription unit promotes anatomical site-dependent establishment and reactivation from latency. J Virol 66:2157-2169.
30. Aschauer D F, Kreuz S, Rumpel S. 2013. Analysis of Transduction Efficiency, Tropism and Axonal Transport of AAV Serotypes 1, 2, 5, 6, 8 and 9 in the Mouse Brain. PLoS One 8:e76310.
31. Salegio E A, Samaranch L, Kells A P, Mittermeyer G, San Sebastian W, Zhou S, Beyer J, Forsayeth J, Bankiewicz K S. 2013. Axonal transport of adeno-associated viral vectors is serotype-dependent. Gene Ther 20:348-352.
32. Castle M J, Perlson E, Holzbaur E L, Wolfe J H. 2013. Long-Distance Axonal Transport of AAV9 is Driven by Dynein and Kinesin-2 and is Trafficked in a Highly Motile Rab7-Positive Compartment. Mol Ther doi:10.1038/mt.2013.237.

Example 2: In Vivo Knock-Down of the Herpes Simplex Virus Type 1 Latency-Associated Transcript Reduces Reactivation from Latency Herpes Simplex Virus (HSV) establishes a life-long latent infection within peripheral nerve ganglia, during which the latent viral genomes are maintained as circular episomes within the nucleus of the neuron. Periodically, the virus reactivates from individual neurons and the newly produced virions are transported via the nerve fibers to the original site of infection, typically the mucosal epithelium of the lip or mouth (HSV-1) or the genitalia (HSV-2) where it can cause cold sores or genital herpes, respectively. During latency, most viral genes are silenced with the exception of one region of the genome encoding the latency-associated transcript (LAT). This non-coding RNA was originally described to play a role in enhancing HSV-1 reactivation, however subsequent evidence that it blocks apoptosis and promotes efficient establishment of latency suggested that its effects on reactivation were secondary to establishment. An AAV vector was utilized to deliver a LAT-targeting hammerhead ribozyme to the latently infected neurons of rabbits that were previously infected with HSV-1. The rabbits were then induced to reactivate the latent HSV by transcorneal iontophoresis of epinephrine. The reduction of LAT accumulation after latency is established was shown to reduce the ability of the virus to reactivate. Therefore the HSV-1 LAT has separate functional roles during both the establishment and reactivation phases of the HSV infection.

Figure 7:
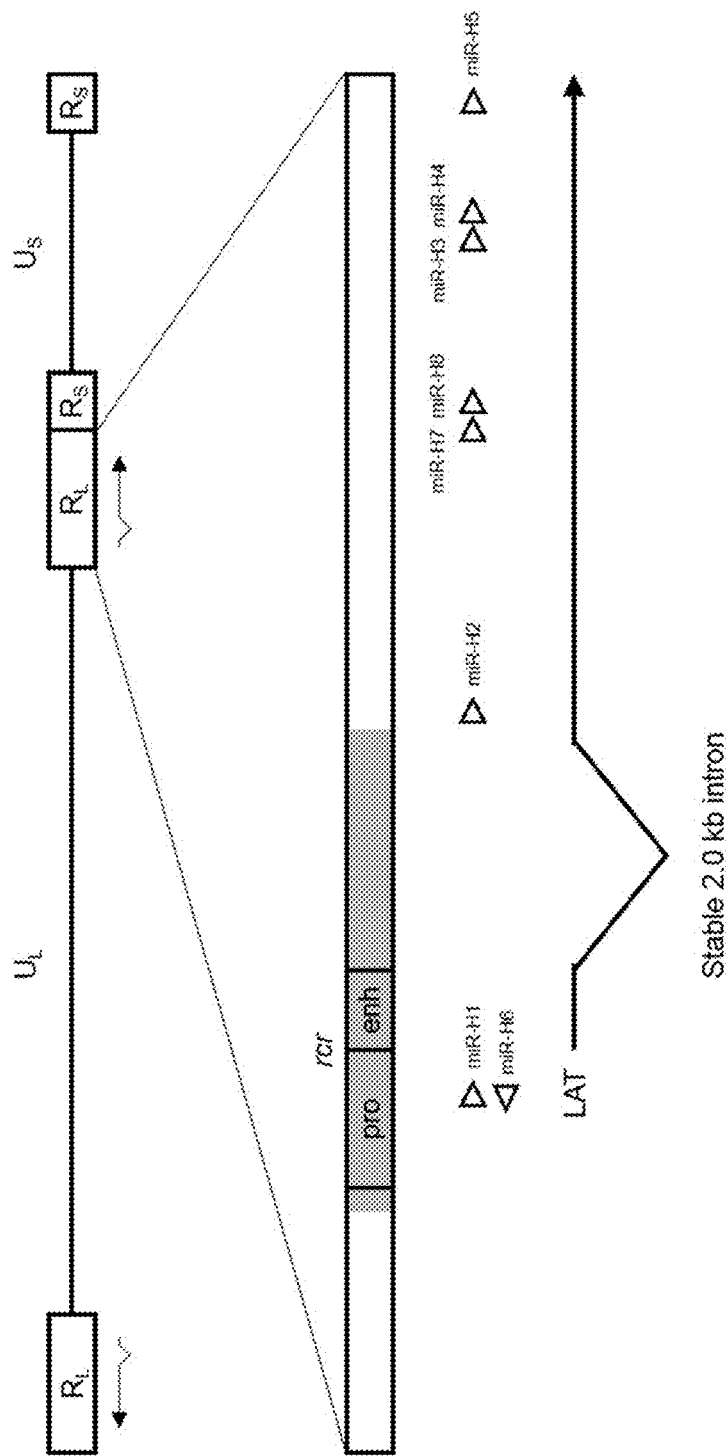
FIG. 7 is a schematic showing the HSV-1 genome and the regions encoding the HSV-1 LAT. The internal long repeat is expanded to show the 8.5 kb primary LAT and the stable 2.0 kb intron, as well as microRNAs encoded within the LAT region. The reactivation critical region (rcr) consists of the LAT promoter (pro), the LAT enhancer (enh), and the first half of the intron (blue shaded region).

The HSV-1 LAT is transcribed from the viral long repeats as a 8.3-8.5 kb polyadenylated primary transcript (FIG. 7). This noncoding RNA (ncRNA) is the only viral transcript to accumulate abundantly during latency (1). The primary transcript is spliced to yield a 2.0 kb intron. This intron is highly stable, with an observed half-life of 24 hours in cell culture (2, 3). It is also stable in vivo and is easily detectable by in situ hybridization within about 25-30% of infected ganglionic neurons (4). Consistent with transcriptional permissiveness of the LAT region during latency, histone H3 hyperacetylation was observed at the LAT region of latent genomes. In contrast, other regions of the HSV-1 genome containing the lytic genes were hypoacetylated, consistent with their repression during latency (5, 6). Genetic studies involving deletions and mutations within the LAT region have yielded a multitude of phenotypes. The LAT region is associated with apoptosis (7), anti-apoptosis (8, 9), neuronal protection (10), and neuronal tropism (11, 12). Study of the LAT region is further complicated by the fact that there are at least 8 microRNAs transcribed from the LAT region (13) whose functions are still being elucidated by mutational analysis (14). The LAT promoter and enhancer (termed the reactivation critical region, or rcr) are associated with reactivation (15, 16), leakiness of lytic gene transcription during latency (17), and histone H3 methylation (18, 19).

It has been difficult to tease apart the exact parts of the LAT region that are responsible for these phenotypes. Functions have often been assigned to cis DNA elements within the LAT region, but the possibility remains that the LAT RNA itself may play a functional role in HSV-1 biology. Another major difficulty in sorting out the function of the LAT is that some phenotypes attributed to the LAT, such as reactivation and establishment of latency, have been difficult to separate from the ability of the LAT to protect neurons from death (10) or block apoptosis (8, 9) during the acute infection, thus reducing establishment of latency in some models. Therefore the goals of this study were to determine if 1) the LAT RNA itself plays a role in HSV-1 biology, and will utilize methods to help separate the role of the RNA from functions of DNA elements in the LAT region, and 2) the LAT is directly involved in facilitating HSV-1 reactivation.

To examine the function of the LAT RNA without perturbing DNA sequence or interfering with transcription, in vivo knockdown of the LAT within sensory neurons was performed using AAV vectors delivered to the rabbit eye to target the HSV-1 LAT being expressed in latently infected sensory neurons. For targeting the LAT, a specifically designed hammerhead ribozyme, a class of catalytic RNA molecules composed of a catalytic loop and three stems that cleave RNAs with high specificity, were chosen (20). First characterized in the plus strand of the satellite RNA of tobacco ringspot virus (21), these molecules are found in many organisms where they act in cis to autolytically cleave RNAs. Soon after their discovery, hammerhead ribozymes were engineered to act in trans (22, 23). In this way, synthetic ribozymes could be designed to specifically target virtually any RNA sequence of interest. There is precedent in the literature for using ribozymes against HSV-1 targets. Multiple ribozymes have previously been designed against HSV-1 transcripts and have been tested for efficacy both in vitro and in vivo (24). However, to date, none of these ribozymes have been directed to the LAT RNA.

In this study it is shown that a ribozyme that targets the HSV-1 LAT, when delivered to the eye of a rabbit that has been latently infected with HSV-1, completely block reactivation of the virus in 50% of the eyes and rabbits compared to rabbits treated with an AAV vector expressing a ribozyme targeting a non-relevant target. This result finally proves that the HSV-1 LAT is directly involved in facilitating efficient reactivation, and opens the door to potentially using this approach to treat recurrent HSV-1 disease.

In Vitro Knockdown of the HSV-1 LAT 5' Exon by a Synthetic Ribozyme

Figure 9A:
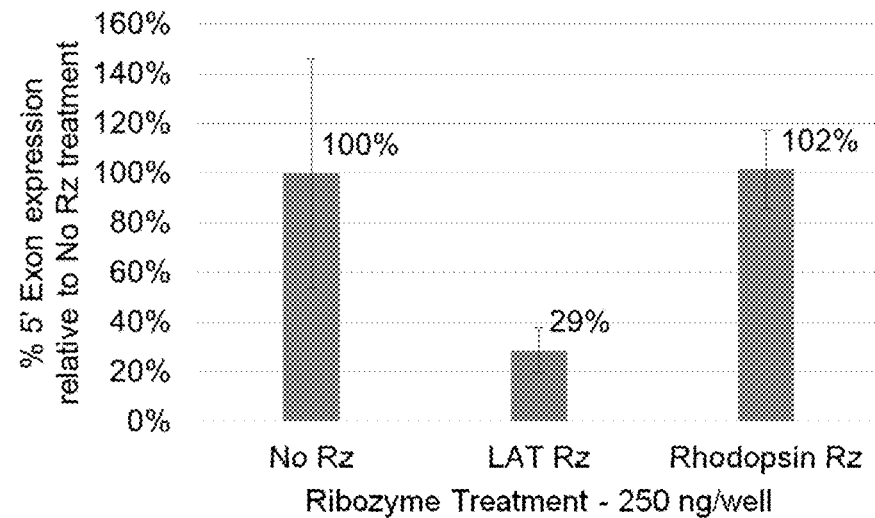
FIGS. 9A-9B show in vitro knockdown of HSV-1 5' exon by LATRz-235 in rabbit skin cells. 5' exon expression levels were analyzed by TaqMan real-time PCR and normalized to the untargeted cellular control rabbit GAPDH. Normalized data are graphed as percentage of 5' exon expression relative to untreated cells (No Rz). Each bar represents the average expression of four wells of a 24-well plate (n=4). Error bars represent standard deviation. Each well was treated with either 250 ng of plasmid (FIG. 9A) or 500 ng of plasmid (FIG. 9B).
Figure 9B:
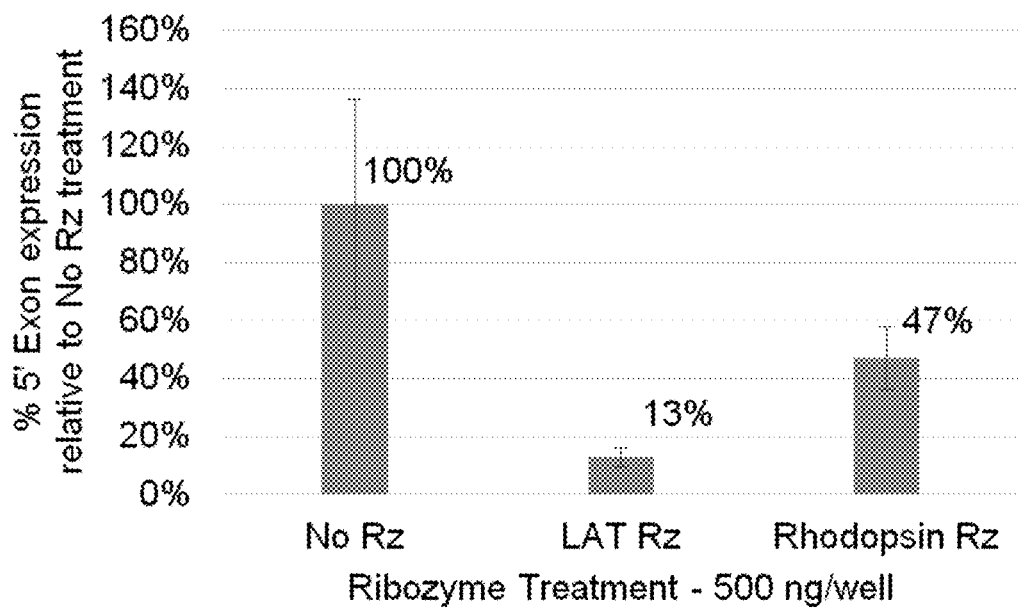

A synthetic hammerhead ribozyme targeting the HSV-1 LAT 5' exon (FIG. 7) was designed, synthesized, and cloned into a scAAV-GFP packaging plasmid. It was designated LATRz-235, indicating the target cleavage site at the 235$^{th}$ nucleotide of the LAT 5' exon sequence (FIG. 8 and Table 1). The efficiency of target knockdown was tested by co-transfecting rabbit skin cells with this plasmid along with a plasmid encoding the target sequence. RNA target knockdown was assayed by reverse transcription followed by TaqMan real-time PCR (FIGS. 9A-9B). Results were normalized to the non-targeted housekeeping gene GAPDH and compared to control transfections using a vector encoding an anti-rhodopsin ribozyme that was not predicted to have an effect on target gene expression.

TABLE 1

Sequence of LATRz-235 and its Target in the LAT 5' Exon

| Ribozyme | Sequence | SEQ ID NO: | Target Sequence | SEQ ID NO: |
|---|---|---|---|---|
| LATRz-235 | GGACACUGAUGAGCGCU UCGGCGCGAAACGAAC | 1 | GUUCGUCUG UCC | 2 |

A baseline of LAT expression was confirmed in cells transfected only with a plasmid encoding the LAT. Relative to this level, LAT 5' exon expression was reduced by 71% in cells co-transfected with the plasmid expressing LATRz-235, while LAT 5' exon expression was not changed by co-transfection of the non-specific anti-rhodopsin ribozyme (FIG. 9A). Doubling the amount of LATRz-235 plasmid resulted in an 87% knockdown of the target RNA. However, at this concentration of transfection DNA, treatment with the non-targeting rhodopsin ribozyme also resulted in a 53% knockdown of the LAT 5' exon (FIG. 9B). It is likely that some portion of the increased knockdown was due to toxicity of transfection conditions. No amplification was detected in no-RT controls. Overall, the performance of LATRz-235 was deemed to be satisfactory and it was selected for in vivo knockdown of the LAT.

Treatment of HSV-1 Latently Infected Rabbits with LATRz-235 Blocks Reactivation in 50% of the Rabbit Eyes.

NZW rabbits were infected by ocular scarification with strain HSV-1 17syn+ as described below. After 30 days, the virus is latent within the trigeminal ganglia (TG), and no infectious virus can be detected in the TG or in the tears, except for occasional spontaneous shedding (26, 27). The advantage of the rabbit model for the study of HSV-1 reactivation is that the latent virus can be efficiently and synchronously induced to reactivate following transcorneal iontophoresis of β-adrenergic agonists such as epinephrine (28). While previous studies had demonstrated that LAT promoter deletions were attenuated for reactivation in the rabbit model (29-31), other studies demonstrated that HSV-1 LAT mutants exhibit a 2-3 fold reduction in establishment of latency (32, 33), and therefore suggested that the effects of the LAT on reactivation were due to fewer HSV-1 genomes available to be reactivated (34). Similar effects of the LAT on establishment were observed in the mouse model (35-37). Therefore, the goal of this study was to determine if knocking down the LAT RNA after normal latency was established had an effect on the efficiency of epinephrine-induced reactivation in the rabbit model.

Latent rabbit eyes were treated with either of two rAAV vectors as described below. One set of rabbits were treated with an AAV vector expressing a ribozyme targeting human rhodopsin (AAV-rhodopsinRZ) as a control, whereas the other set of rabbits were treated with the HSV-1 LAT targeting ribozyme (AAV LATRz-235). It was previously demonstrated that AAV delivered to the rabbit eye is efficiently transported to the TG and can efficiently transduce >70% of the total neurons (Watson et al., in press). Seventeen days after treatment, the rabbit eyes were iontophoresed with epinephrine and swabbed daily for 8 days to collect tears. These swabs were then assayed for infectious virus.

No HSV-1 was detected in 50% of the rabbits that were treated with AAV LATRz-235, compared to 100% of the rabbits treated with AAV-rhodopsinRZ (Table 2). When the reactivation frequency was assessed on a per-eye basis, only 33% of rabbit eyes treated with AAV LATRz-235 had at least one positive swab compared to 79% treated with AAV-rhodopsinRZ. Finally, when total numbers of positive swabs were compared (as a means of assessing both frequency and duration of HSV-1 shedding in the tears), only 17% of the total swabs were positive after treatment with AAV LATRz-235, compared to 30% treated with AAV-rhodopsinRZ. These results indicate that the AAV LATRz-235 vector treatment blocked detectable reactivation in approximately 50% of the rabbits, eyes, and swabs compared to controls.

TABLE 2

Epinephrine-Induced Reactivation Data

| Treatment | Total Positive Rabbits | Total Positive Eyes | Total Positive Swabs |
|---|---|---|---|
| AAV-rhodopsinRz | 7/7 (100%) | 11/14 (79%) | 52/168 (30%) |
| AAV-LATRz | 3/6 (50%) | 4/12 (33%) | 25/144 (17%) |

Figure 10A:
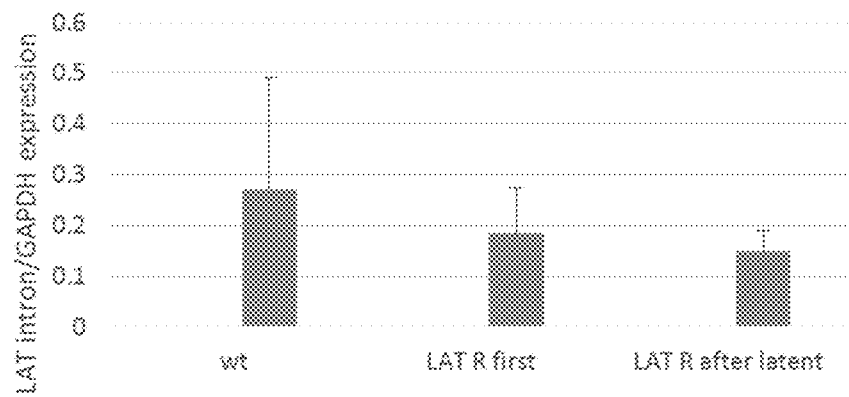
FIGS. 10A-10C show RT-PCR analysis of HSV-1 transcripts in latently infected rabbit TG after LATRz-235 treatment. RNA was isolated from rabbit TG that had been latently infected with HSV-1 and then either untreated, or treated with the LATRz-235. The RNA was then reverse transcribed and subjected to Q-PCR with primers specific for the LAT intron, ICP0 or gC as well as rabbit GAPDH. The values presented represent relative quantities of the LAT intron (FIG. 10A), ICP0 (FIG. 10B) or gC (FIG. 10C) RNA (normalized to cellular GAPDH).
Figure 10B:
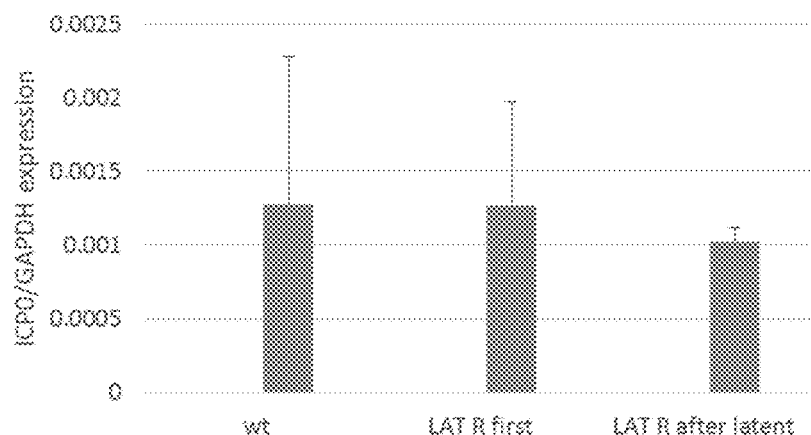
Figure 10C:
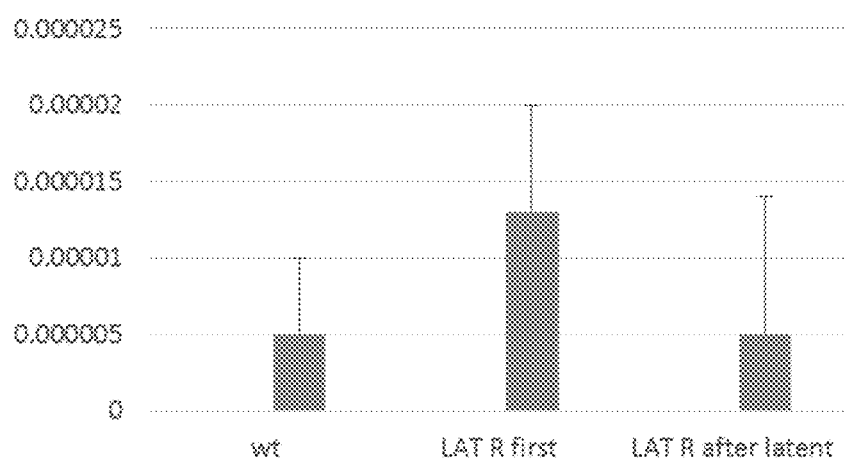
Figure 11:
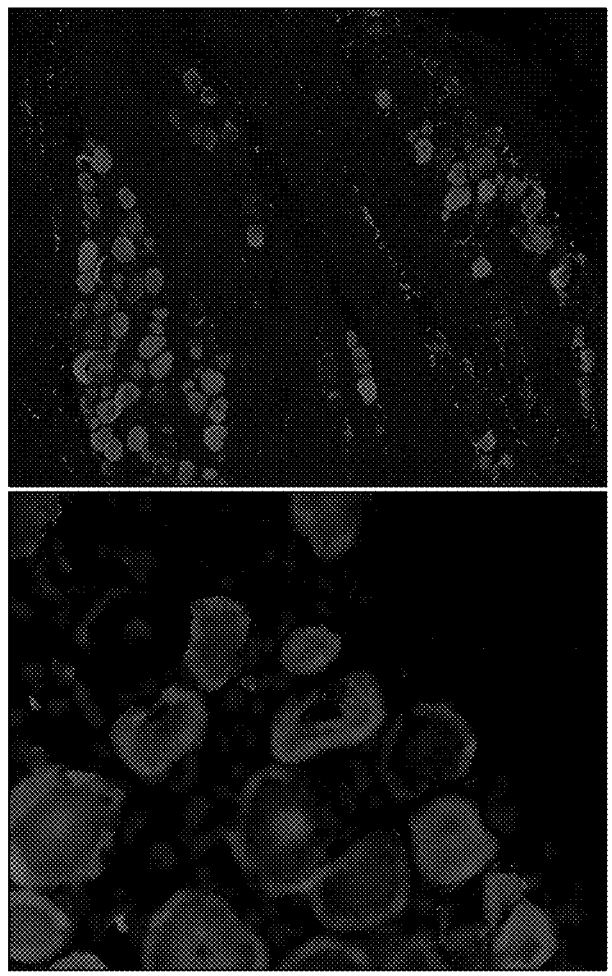
FIG. 11 shows immunofluorescence (IF) demonstrating long-term expression of AAV8-GFP in a high percentage of latently infected rabbit TG neurons. IF was performed to identify populations of neurons harboring the AAV8-GFP vector using rabbits latently infected with HSV-1 strain 17Syn+ that were treated with the AAV8-LAT ribozyme. Sections were incubated with mouse anti-GFP primary antibody. AlexaFluor 548 (Invitrogen) was used as the secondary antibody for immunofluorescent visualization using a Leica de-convolution microscope with Slidebook 5.0. The top panel represents a 10× image and the bottom panel a 40× image from the same section. DAPI staining in blue represents nuclei of satellite cells present in the sections.
Figure 12:
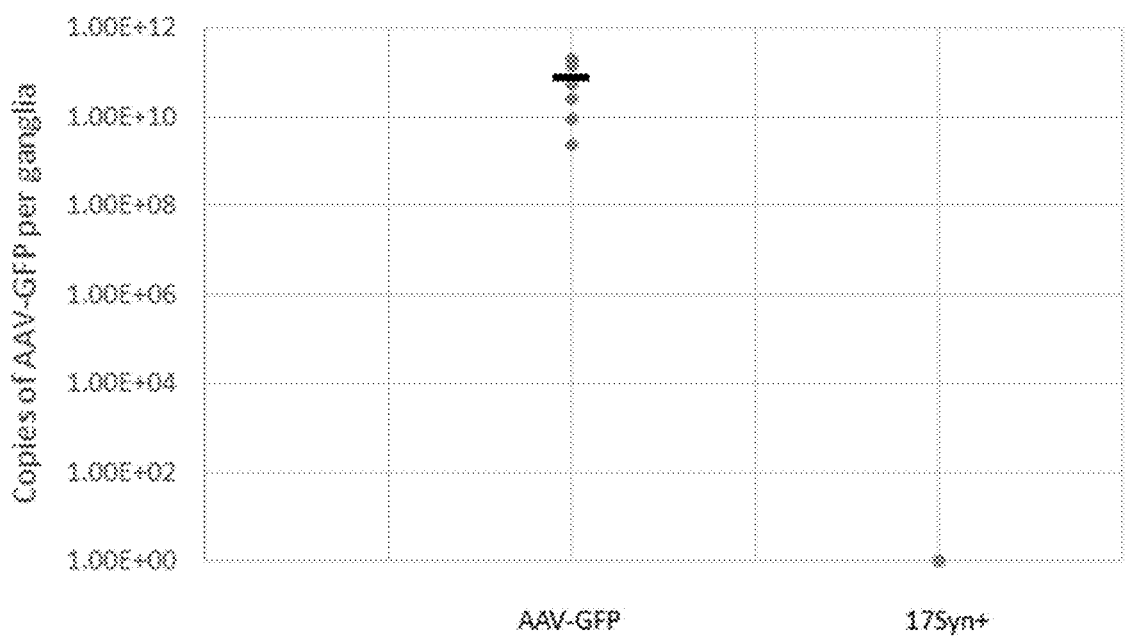
FIG. 12 shows quantification of AAV8-GFP copies per rabbit ganglia. The number of AAV8 genomes per ganglia was determined using real time PCR. Following DNA isolation and purification from rabbit TG latent with only HSV-1 17Syn+(negative control) and rabbit TG latent with 17Syn+ that were co-infected with AAV8-GFP, we performed endpoint PCR, followed by qPCR for GFP using the end-point sample as a DNA template. Our data show a range of 1.00 E+9 to 1.00 E+11 copies of GFP in rabbit ganglia.
Figure 13:
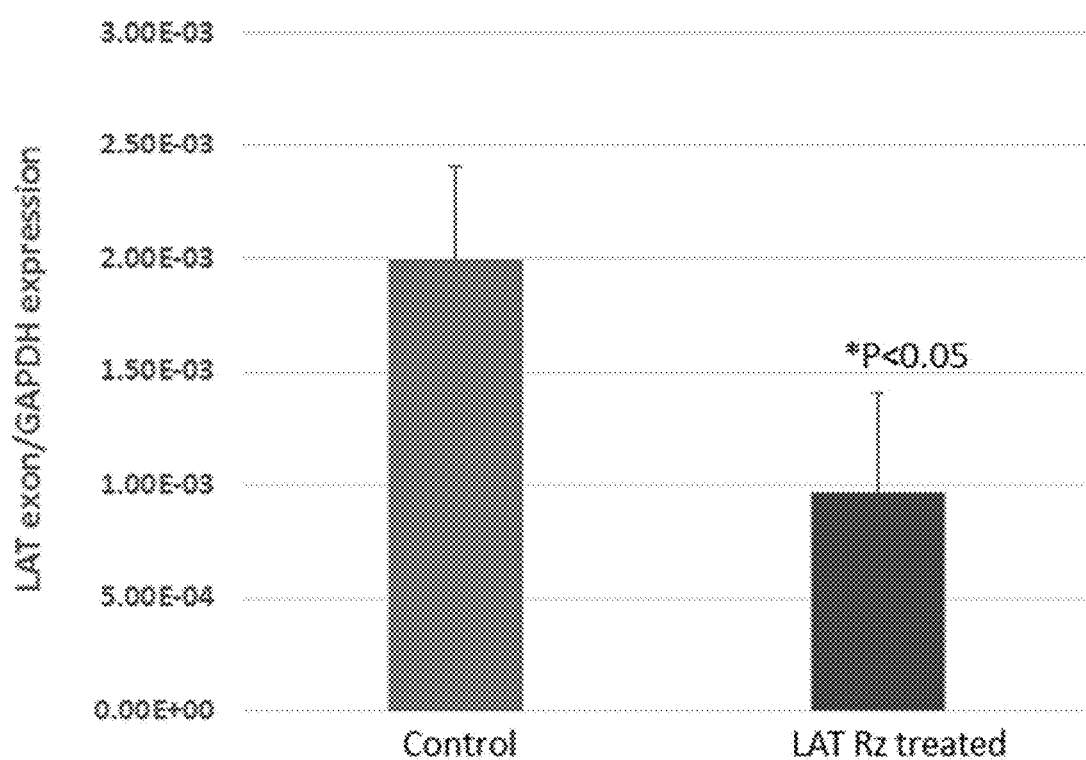
FIG. 13 shows LAT expression significantly decreased following treatment with AAV8-GFP/LAT Ribozyme. LAT transcript abundance was determined using latently infected rabbit TG. Control samples represent ganglia from rabbits infected with wt virus and treated only with the AAV8-Rhodposin control (N=7). The LAT Rz samples represent ganglia from rabbits infected with wt virus and treated with the AAV8-GFP/LAT Rz vector after latency (N=6). RNA was isolated and analyzed by RT-PCR using primers and probes specific for the LAT 5' exon region of the genome. Relative quantities were determined for LAT and then normalized to the relative quantities of rabbit GAPDH to account for variations between samples. The average values for each virus are presented along with standard deviations (P<0.05). All samples were done in triplicate and statistical analyses were performed as one-way ANOVA using SigmaPlot 12.5.

Finally, after the reactivation study was complete, rabbit TG were dissected and RNA extracted. The RNA was reverse transcribed and Q-PCR analysis was performed to determine amounts of the HSV-1 LAT, ICP0 (immediate early gene) and glycoprotein C (a late gene) (FIGS. 10A-10C). These data indicate less LAT was detected in the AAV LATRz-235 treated groups, whereas no significant changes in ICP0 or gC were detected. Further rabbit TG were dissected and one TG per rabbit was processed and analyzed by immunohistochemistry to detect AAV-GFP expression. These analyses revealed that >80% of the neurons in the TG were transduced by AAV and expressed GFP (FIG. 11, Table 3). The other TG was subjected to RNA extraction. The RNA was reverse transcribed and Q-PCR analysis was performed to determine amounts of the GFP RNA (FIG. 12) and HSV-1 LAT (FIG. 13). These data indicate less LAT was detected in the AAV LATRz-235 treated groups. These data confirm the ability of AAV LATRz-235 to decrease LAT levels in the latent ganglia and this reduction correlates with decreased reactivation.

TABLE 3

Treatment with AAV-LATRz Reduces Induced Reactivation in vivo

| Treatment | Rabbits Positive/ Total Rabbit Reactivating (%)[#] | Eyes Positive/ Total Eyes Reactivating (%) | Swabs Positive/Total Swabs (%) |
|---|---|---|---|
| Rhod Rz (control) | 10/10 (100%)* | 16/20 (80.0%)* | 66/254 (26.0%)* |
| LAT Rz | 4/9 (44.4%) | 6/18 (33.3%) | 38/228 (16.7%) |

*p < 0.0005 by Exact Version of Chi-square analysis for all pair-wise comparisons with Control (no LAT Rz)
[#]Reactivation was induced by transcorneal iontophoresis (0.8 mA for 8 minutes) of 0.01% epinephrine was performed on each eye once daily for 3 consecutive days, with daily ocular swabs for 10 days total. Swabs were placed in DMEM, plated on CV-1 cells and monitored for 7 days for evidence of CPE. The data presented in the table represents 2 separate consecutive experiments combined.

HSV-1 recombinants with deletions in the LAT promoter are associated with many phenotypes, including reactivation efficiency in various in vivo models (15, 16, 38, 39), leakiness of lytic gene transcription during latency (17, 40), and H3K27me3 enrichment on the latent HSV-1 genome (18, 19). Yet the biological mechanism for the link between the LAT region and these phenotypes remains elusive. It is considered that the influence of the LAT may be multifactorial. Deletions in the LAT promoter remove transcription factor binding sites and other cis DNA elements that may be important for regulation of latent-phase transcription. These deletions also abolish virtually all transcription at the LAT promoter, a region that is normally highly transcriptionally active during latency. Finally, the absence of transcription results in the absence of the LAT RNA itself, which is typically in high abundance within some infected neurons. Previous studies have often characterized LAT expression and its importance for HSV-1 biology, but none have explicitly examined the LAT RNA itself to determine if it plays a role. The primary aim of the experiments described here were to determine if the LAT RNA plays a role in facilitating HSV-1 reactivation from latency.

The reduction of LAT transcript levels after HSV-1 latency has been established results in a block in detectable reactivation in 50% of the rabbit treated was shown. This for the first time proves that the LAT is involved in directly facilitating reactivation, and that the reduced reactivation exhibited by LAT mutants in the past was not due exclusively (if at all) to a reduction in establishment of latency. This finding provides evidence that the LAT transcript has multiple functions, and that one of which is to facilitate induced reactivation. The fact that the ribozyme reduces the LAT post-transcriptionally, would seem to eliminate the model that the LAT functions by keeping the genome "open" by a transcriptional mechanism that facilitates reactivation. Instead, the data suggests that the LAT functions as a lncRNA, possibly by maintaining the genome in a transcriptionally permissive configuration possibly by the recruitment of chromatin modifiers. Similarly, some of the miRNAs that are encoded by the LAT could be involved in this process. Data that LAT promoter deletions are associated with increased heterochromatin modifications in the mouse, and have less "leaky" lytic gene transcription in the rabbit support this model (19, 41). However, it should be noted that LAT promoter deletions in the KOS background exhibit a different profile (18).

One of the striking observations of this study is that the AAV LATRz-235 only reduced the total LAT burden by 2-3 fold at the level of the whole ganglia. The fact that 50% of the rabbits exhibited no detectable reactivation suggests that either a reduction in a small amount of total LAT is sufficient to significantly reduce reactivation, or that the levels of LAT reduction may have been greater in some neurons than others. It should also be noted that this ribozyme reduced LAT levels in vitro by 70%. It is possible that more efficient LAT targeting or targeting the LAT with multiple ribozymes or shRNAs may have an even greater effect on blocking reactivation.

Finally, this is the first example of delivering a payload with therapeutic potential using an AAV vector to neurons from the periphery. Therefore, this study provides proof-of-principle that similar approaches have great potential to treat HSV recurrent disease in humans.

Materials and Methods

Viruses and cells. A low passage stock of HSV-1 strain 17syn+ was obtained. Viruses were propagated on rabbit skin (RS) cells as described previously (9). Briefly, RS cells were propagated in minimal essential medium (MEM, Gibco Life Technologies, Gaithersburg, Md.) with 5% fetal bovine serum (FBS) and antibiotics at 37° C. in a humidified 5% carbon dioxide atmosphere. To assess cytopathic effect (CPE) of tear film swabs in the reactivation studies, primary rabbit kidney (PRK) cells were propagated in MEM with 5% FBS using the same conditions.

Target selection and design of synthetic hammerhead ribozymes. The LAT 5' exon and intron regions of the HSV-1 genome (NCBI database accession number NC_001806) were scanned for hammerhead ribozyme cleavage sites. The nucleotide triplets GUC, CUC, and UUC were specifically selected as potential target sites. Hybridizing arms were designed complementary to sequence surrounding the cleavage site. MFOLD software (25) was used to predict secondary structure of each ribozyme. Ribozymes predicted to have a correctly folded catalytic core and open hybridizing arms were carried forward to in vitro testing. An example of sequence selection, design, and predicted folding is shown in FIG. 8.

Cloning synthetic ribozymes into AAV packaging plasmids. Selected synthetic hammerhead ribozymes were cloned into scAAV-GFP packaging plasmids for in vitro testing and subsequent vector production. The ribozyme sequence was placed downstream of an H1 promoter and terminated by an RNA polymerase III termination sequence. These mini-genes were synthesized by GenScript with SalI restriction endonuclease sites at each end. AAV packaging vector and the insert were digested with SalI (New England Biolabs) and ligated. Ligations were transformed into SURE electroporation competent cells (Stratagene) and grown in LB media. Plasmids were isolated and purified by CsCl centrifugation. Insertion was confirmed by PCR and Sanger sequencing.

In vitro testing of synthetic hammerhead ribozymes. Lipofectamine 2000 (Invitrogen) was used to co-transfect a plasmid encoding synthetic hammerhead ribozymes and a plasmid encoding the target LAT transcript into rabbit skin cells. Each transfection was performed in triplicate in 24-well plate format. A plasmid expressing an anti-rhodopsin ribozyme was co-transfected in control wells to account for off-target or non-specific effects. 24 hours post transfection, RNA was isolated using Trizol (Ambion) and used for subsequent reverse transcription and qPCR analysis.

Rabbit inoculation with HSV-1 and establishment of latency. New Zealand White rabbits (2-3 kg) were inoculated with $1-2\times10^5$ plaque-forming units (pfu) of virus per eye in a suspension of 25 µl MEM with 5% FBS. The viral suspension was placed in the cul-de-sac of the scarified eye, the eye closed and massaged for 30 seconds with care to prevent virus loss. On post-inoculation (PI) day 4, all corneas were examined by slit lamp microscopy (SLE) with 0.1% fluorescein for evidence of acute herpetic keratitis. Rabbits inoculated with 17syn+ demonstrated single to multiple punctate dendritic lesions on PI day 4. 17ΔA developed similar herpetic lesions by PI day 9. On PI day 30, all eyes were examined to ensure that the corneal epithelium was free of lesions. Only eyes that were normal by SLE were included in the reactivation study. Rabbits that exhibited acute lesions with subsequent recovery were considered latently infected.

Treatment of rabbit eyes with AAV LATRz-235 vector. Rabbit corneas were abraded as previously described (ref) and $1\times10^{11}$ g.e. of LATRz-235 was applied to both eyes in a volume of 250 per eye in saline.

Induction of HSV-1 reactivation in rabbits. Transcorneal iontophoresis (0.8 mA for 8 minutes) of 0.01% epinephrine was performed on each eye once daily for 3 consecutive days (PI days 31, 32, and 33) (21). To assess the frequency of reactivation, tears were collected daily on each of the three reactivation stimulus days (prior to each iontophoresis procedure) and for an additional seven days thereafter (total of 10 consecutive days post-iontophoresis initiation). Tear film collection consisted of inserting a Dacron™ swab (Puritan, Hardwood Products Company, Guilford, Me.) into the cul-de-sac of the eye and passed over the corneal surface and conjunctiva. Each eye was swabbed independently and the swab placed in a tube containing 1 mL DMEM (1% FBS). Tubes were place in a −80° C. freezer overnight and then thawed at 37° C. the following day. The dacron swabs were removed aseptically and the media was placed into a 24-well plate containing a monolayer of CV-1 cells. The plates were then monitored for 7 days for evidence of CPE.

PCR for AAV-GFP quantification. DNA was isolated from rabbit TG latently infected with 17Syn+ alone or with 17Syn+/AAV8-GFP using phenol-chloroform extraction. Following DNA purification, end point PCR was done using the Qiagen Hi Fidelity PCR kit, according to the manufacturer's instructions. Briefly, individual PCR reactions were done using samples with the following primers specific for GFP amplification: forward-TGATGCCACATACG-GAAAGC (SEQ ID NO: 68); reverse-AAAAGCACTGCACGCCATAG (SEQ ID NO: 69) with the following protocol: 95° C. for 5 minutes, followed by 35×95° C. for 30 seconds, 63° C. for 30 seconds, 72° C. for 30 seconds, then 1×72° C. for 10 minutes. Following end point PCR, 3 µl of sample was used to perform qPCR using Power-up SYBR green master mix (Applied Biosystems) according to the manufacturer's recommendations and the following PCR parameters: 50° C. —2 minutes; 95° C. —2 minutes; 35×95° C. —30 seconds, 63° C. —30 seconds.

Reverse transcription. To remove any DNA contamination, RNA samples from transfection experiments were DNase treated with TURBO DNA free (Ambion). cDNA was synthesized using OmniScript (Qiagen) with 10 µM random decamer primers (Ambion). To control for any residual genomic DNA in cDNA samples, no-RT controls reactions were performed. These reactions included all components except the OmniScript reverse transcription enzyme.

Real-time PCR. cDNA samples from transfection experiments were analyzed by TaqMan quantitative real-time PCR on a StepOnePlus thermocycler (Applied Biosystems). Quantities were normalized to a cellular housekeeping gene, rabbit GAPDH. Custom TaqMan assay sequences are given in Table 4.

TABLE 4

Custom TaqMan Assay Sequences

| Assay Name | Forward Primer | SEQ ID NO: | Reverse Primer | SEQ ID NO: | Probe | SEQ ID NO: |
|---|---|---|---|---|---|---|
| LAT 5' Exon | GGCTCCATCG CCTTTCCT | 3 | AAGGGAGGGAGGAG GGTACTG | 6 | TCTCGCTTC TCCCC | 9 |
| LAT Intron | CGCCCCAGAG GCTAAGG | 4 | GGGCTGGTGTGCTGT AACA | 7 | CCACGCCA CTCGCG | 10 |

TABLE 4-continued

Custom TaqMan Assay Sequences

| Assay Name | Forward Primer | SEQ ID NO: | Reverse Primer | SEQ ID NO: | Probe | SEQ ID NO: |
|---|---|---|---|---|---|---|
| Rabbit GAPDH | GCACCACCAACTGCTTAGC | 5 | CCTCCACAATGCCGAAGTG | 8 | CTGGCCAAGGTCATCC | 11 |

Immunofluorescence. Rabbit TG: Slides containing sections of rabbit TG were deparaffinized, hydrated, and peroxidase blocked through a series of washes that included: (1) Two xylene washes for five minutes each, (2) two 100% ethanol washes for 2 minutes each, (3) one 3% hydrogen peroxide wash (30% hydrogen peroxide was diluted 1:10 in 100% methanol) for 10 minutes, (4) one 95% ethanol wash for three minutes, (5) one 70% ethanol wash for one minute, and (6) one TBS-T wash for one minute. Epitope retrieval was done using the IHC-Tek Epitope Retrieval Steamer Set. The retrieval jar was filled with retrieval solution, slides were placed inside and the jar was placed in the steamer for 1 hour. The lid was removed from the jar and the solution was cooled to RT. Slides were washed with TBS-T and placed in a humidified chamber. Slides were blocked using 1.5% normal serum (goat) for 30 minutes and washed with TBS-T. Sections were then incubated with primary antibody (1:200 of mouse anti-GFP) for 24 hours at 4° C. Secondary antibody incubation was then performed using 1:1000 goat anti-mouse AlexaFluor 548 (Invitrogen) for 2 hours at room temperature, followed by a TBS-T wash. The slides were mounted using ProLong gold mounting media (Invitrogen) and imaged using a Leica deconvolution microscope equipped with Slidebook 5.0.

References (Example 2)

1. Stevens J G, Wagner E K, Devi-Rao G B, Cook M L, Feldman L T. 1987. RNA complementary to a herpesvirus alpha gene mRNA is prominent in latently infected neurons. *Science* 235:1056-1059.
2. Farrell M J, Dobson A T, Feldman L T. 1991. Herpes simplex virus latency-associated transcript is a stable intron. *Proc Natl Acad Sci USA* 88:790-794.
3. Thomas D L, Lock M, Zabolotny J M, Mohan B R, Fraser N W. 2002. The 2-kilobase intron of the herpes simplex virus type 1 latency-associated transcript has a half-life of approximately 24 hours in SY5Y and COS-1 cells. *J Virol* 76:532-540.
4. Wagner E K, Bloom D C. 1997. Experimental investigation of herpes simplex virus latency. *Clin Microbiol Rev* 10:419-443.
5. Kubat N J, Amelio A L, Giordani N V, Bloom D C. 2004. The Herpes Simplex Virus Type 1 Latency-Associated Transcript (LAT) Enhancer/rcr Is Hyperacetylated during Latency Independently of LAT Transcription. *J Virol* 78:12508-12518.
6. Kubat N J, Tran R K, McAnany P, Bloom D C. 2004. Specific histone tail modification and not DNA methylation is a determinant of herpes simplex virus type 1 latent gene expression. *J Virol* 78:1139-1149.
7. Perng G C, Maguen B, Jin L, Mott K R, Kurylo J, BenMohamed L, Yukht A, Osorio N, Nesburn A B, Henderson G, Inman M, Jones C, Wechsler S L. 2002. A novel herpes simplex virus type 1 transcript (A L-RNA) antisense to the 5' end of the latency-associated transcript produces a protein in infected rabbits. *J Virol* 76:8003-8010.
8. Perng G C, Jones C, Ciacci-Zanella J, Stone M, Henderson G, Yukht A, Slanina S M, Hofman F M, Ghiasi H, Nesburn A B, Wechsler S L. 2000. Virus-induced neuronal apoptosis blocked by the herpes simplex virus latency-associated transcript. *Science* 287:1500-1503.
9. Ahmed M, Lock M, Miller C G, Fraser N W. 2002. Regions of the herpes simplex virus type 1 latency-associated transcript that protect cells from apoptosis in vitro and protect neuronal cells in vivo. *J Virol* 76:717-729.
10. Thompson R L, Sawtell N M. 2001. Herpes simplex virus type 1 latency-associated transcript gene promotes neuronal survival. *J Virol* 75:6660-6675.
11. Margolis T P, Imai Y, Yang L, Vallas V, Krause P R. 2007. Herpes simplex virus type 2 (HSV-2) establishes latent infection in a different population of ganglionic neurons than HSV-1: role of latency-associated transcripts. *J Virol* 81:1872-1878.
12. Imai Y, Apakupakul K, Krause P R, Halford W P, Margolis T P. 2009. Investigation of the mechanism by which herpes simplex virus type 1 LAT sequences modulate preferential establishment of latent infection in mouse trigeminal ganglia. *J Virol* 83:7873-7882.
13. Umbach J L, Kramer M F, Jurak I, Karnowski H W, Coen D M, Cullen B R. 2008. MicroRNAs expressed by herpes simplex virus 1 during latent infection regulate viral mRNAs. *Nature* 454:780-783.
14. Flores O, Nakayama S, Whisnant A W, Javanbakht H, Cullen B R, Bloom D C. 2013. Mutational inactivation of herpes simplex virus 1 microRNAs identifies viral mRNA targets and reveals phenotypic effects in culture. *J Virol* 87:6589-6603.
15. Hill J M, Rayfield M A, Haruta Y. 1987. Strain specificity of spontaneous and adrenergically induced HSV-1 ocular reactivation in latently infected rabbits. *Curr Eye Res* 6:91-97.
16. Bloom D C, Hill J M, Devi-Rao G, Wagner E K, Feldman L T, Stevens J G. 1996. A 348-base-pair region in the latency-associated transcript facilitates herpes simplex virus type 1 reactivation. *J Virol* 70:2449-2459.
17. Giordani N V, Neumann D M, Kwiatkowski D L, Bhattacharjee P S, McAnany P K, Hill J M, Bloom D C. 2008. During herpes simplex virus type 1 infection of rabbits, the ability to express the latency-associated transcript increases latent-phase transcription of lytic genes. *J Virol* 82:6056-6060.
18. Cliffe A R, Garber D A, Knipe D M. 2009. Transcription of the herpes simplex virus latency-associated transcript promotes the formation of facultative heterochromatin on lytic promoters. *J Virol* 83:8182-8190.
19. Kwiatkowski D L, Thompson H W, Bloom D C. 2009. The polycomb group protein Bmi1 binds to the herpes simplex virus 1 latent genome and maintains repressive histone marks during latency. *J Virol* 83:8173-8181.

20. Forster A C, Symons R H. 1987. Self-cleavage of plus and minus RNAs of a virusoid and a structural model for the active sites. *Cell* 49:211-220.
21. Prody G A, Bakos J T, Buzayan J M, Schneider I R, Bruening G. 1986. Autolytic processing of dimeric plant virus satellite RNA. *Science* 231:1577-1580.
22. Haseloff J, Gerlach W L. 1992. Simple RNA enzymes with new and highly specific endoribonuclease activities. 1988. *Biotechnology* 24:264-269.
23. Uhlenbeck O C. 1987. A small catalytic oligoribonucleotide. *Nature* 328:596-600.
24. Liu J, Lewin A S, Tuli S S, Ghivizzani S C, Schultz G S, Bloom D C. 2008. Reduction in severity of a herpes simplex virus type 1 murine infection by treatment with a ribozyme targeting the UL20 gene RNA. *J Virol* 82:7467-7474.
25. Zuker M. 2003. Mfold web server for nucleic acid folding and hybridization prediction. *Nucleic Acids Res* 31:3406-3415.
26. Berman E J, Hill J M. 1985. Spontaneous ocular shedding of HSV-1 in latently infected rabbits. *Invest Opthalmol Vis Sci* 26:587-590.
27. Nesburn A B, Elliot J H, Leibowitz H M. 1967. Spontaneous reactivation of experimental herpes simplex keratitis in rabbits. *Arch Ophthalmol* 78:523-529.
28. Hill J M, Haruta Y, Rootman D S. 1987. Adrenergically induced recurrent HSV-1 corneal epithelial lesions. *Curr Eye Res* 6:1065-1071.
29. Perng G-C, Dunkel E C, Geary P A, Slanina S M, Ghiasi H, Kaiwar R, Nesburn A B, Wechsler S L. 1994. The latency-associated transcript gene of herpes simplex virus type 1 (HSV-1) is required for efficient in vivo spontaneous reactivation of HSV-1 from latency. *J Virol* 68:8045-8055.
30. Hill J M, Sedarati F, Javier R T, Wagner E K, Stevens J G. 1990. Herpes simplex virus latent phase transcription facilitates in vivo reactivation. *Virology* 174:117-125.
31. Bloom D C, Devi-Rao G B, Hill J M, Stevens J G, Wagner E K. 1994. Molecular analysis of herpes simplex virus type 1 during epinephrine induced reactivation of latently infected rabbits in vivo. *J Virol* 68:1283-1292.
32. Perng G C, Jones C, Ciacci-Zanella J, Stone M, Henderson G, Yukht A, Slanina S M, Hofman F M, Ghiasi H, Nesburn A B, Wechsler S L. 2000. Virus-induced neuronal apoptosis blocked by the herpes simplex virus latency-associated transcript. *Science* 287:1500-1503.
33. Perng G C, Slanina S M, Yukht A, Ghiasi H, Nesburn A B, Wechsler S L. 2000. The latency-associated transcript gene enhances establishment of herpes simplex virus type 1 latency in rabbits. *J Virol* 74:1885-1891.
34. Sawtell N M, Poon D K, Tansky C S, Thompson R L. 1998. The latent herpes simplex virus type 1 genome copy number in individual neurons is virus strain specific and correlates with reactivation. *J Virol* 72:5343-5350.
35. Thompson R L, Sawtell N M. 2001. Herpes simplex virus type 1 latency-associated transcript gene promotes neuronal survival. *J Virol* 75:6660-6675.
36. Thompson R L, Sawtell N M. 2000. HSV latency-associated transcript and neuronal apoptosis. *Science* 289:1651.
37. Thompson R L, Sawtell N M. 1997. The herpes simplex virus type 1 latency-associated transcript gene regulates the establishment of latency. *J Virol* 71:5432-5440.
38. Bloom D C, Devi-Rao G B, Hill J M, Stevens J G, Wagner E K. 1994. Molecular analysis of herpes simplex virus type 1 during epinephrine-induced reactivation of latently infected rabbits in vivo. *J Virol* 68:1283-1292.
39. Perng G C, Dunkel E C, Geary P A, Slanina S M, Ghiasi H, Kaiwar R, Nesburn A B, Wechsler S L. 1994. The latency-associated transcript gene of herpes simplex virus type 1 (HSV-1) is required for efficient in vivo spontaneous reactivation of HSV-1 from latency. *J Virol* 68:8045-8055.
40. Chen S H, Kramer M F, Schaffer P A, Coen D M. 1997. A viral function represses accumulation of transcripts from productive-cycle genes in mouse ganglia latently infected with herpes simplex virus. *J Virol* 71:5878-5884.
41. Giordani N V, Neumann D M, Kwiatkowski D L, Bhattacharjee P S, McAnany P K, Hill J M, Bloom D C. 2008. During HSV-1 Infection of Rabbits, the Ability to Express the LAT Increases Latent-Phase Transcription of Lytic Genes. *J Virol* 82:6056-6060.

Example 3: Identification of Additional Latent Transcripts

Figure 14:
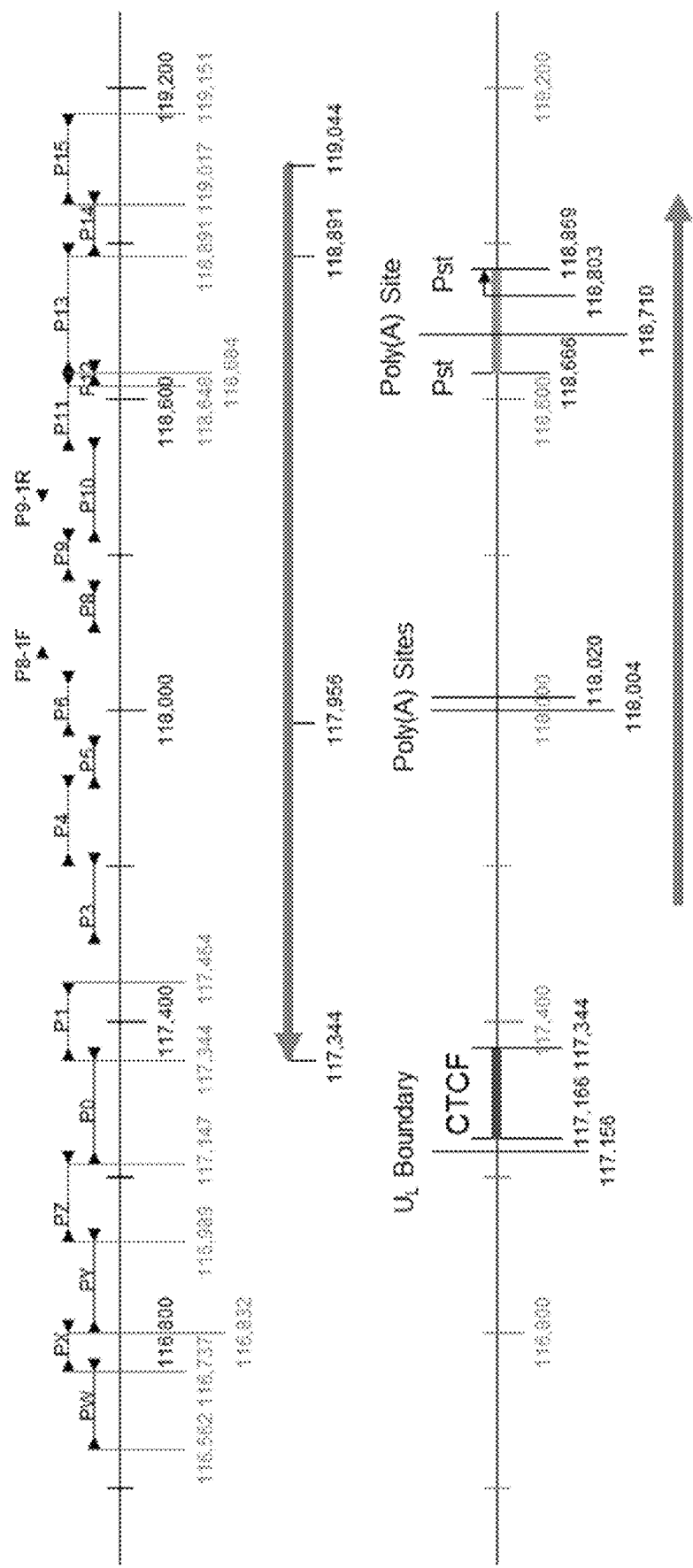
FIG. 14 shows strand-specific RT-PCR fine-mapping, which revealed the presence of two upstream transcripts: TAL and ATAL.

Previously unidentified long non-coding RNAs (lncRNAs) were identified that overlap with the 5' exon region of the LAT (e.g., the "LAT" latency-associated transcript described in detail in Examples 1 and 2) that are believed to be contributing to the regulation of HSV reactivation. The additional latency associated transcripts are referred to herein as "TAL" and "ATAL" (antisense TAL), which were identified by strand-specific RT-PCR fine-mapping (FIG. 14). It is thought that at least two microRNAs are transcribed from the TAL and ATAL regions (e.g., miR-H1 and miR-H6).

Figure 15:
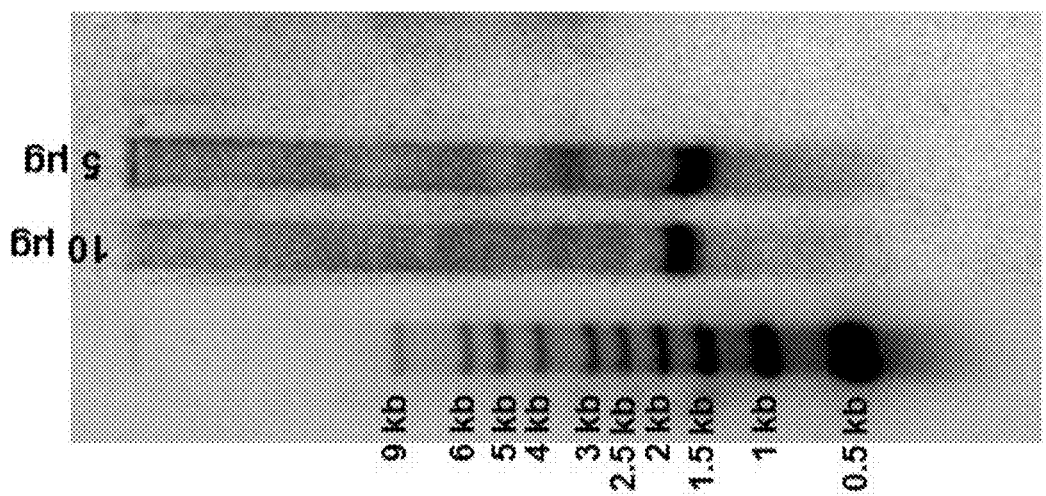
FIG. 15 shows Northern blot analysis of the ATAL transcript. Total RNA was isolated and pooled from 2 rabbit TG latently-infected with 17syn+. Northern blot analysis using a DNA probe generated from a LAT promoter primer set (PCR primers that transcribe a region of the LAT promoter) is shown. The size of transcript was determined to be approximately 1.7 kb.
Figure 16:
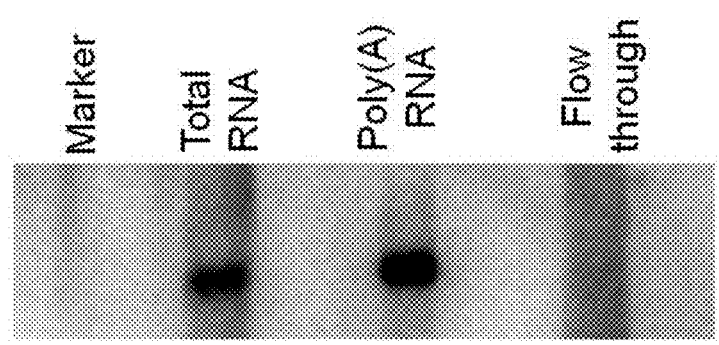
FIG. 16 shows further Northern blot analysis of the ATAL transcript indicating that the ATAL transcript is polyadenylated. RNA was isolated from 2 pooled latently-infected rabbit TG. The total RNA was passed through an oligo(dT) column to yield poly(A) RNA. Northern blot analysis using a DNA probe generated from a LAT promoter primer set is shown.

Total RNA was isolated and pooled from 2 rabbit TG latently-infected with 17syn+. Northern blot analysis revealed the size of ATAL transcript to be approximately 1.7 kb (FIG. 15). The total RNA was passed through an oligo (dT) column to yield poly(A) RNA, and Northern blot analysis confirmed that the ATAL transcript was polyadenylated (FIG. 16). FIG. 17 illustrates mapping of TAL and ATAL transcripts. Primer extension was conducted to map the 5' and 3' ends of the ATAL and TAL transcripts (FIG. 18).

Figure 19:
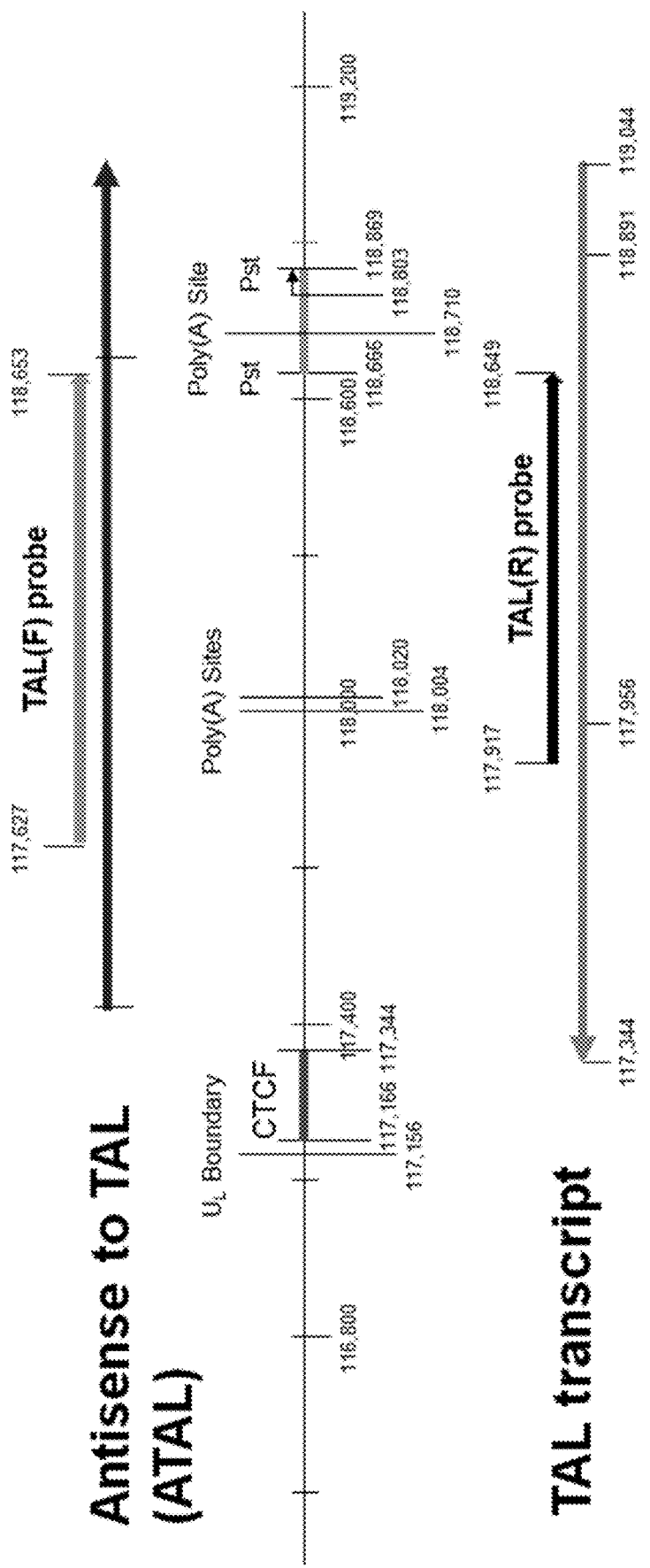
FIG. 19 shows a map of strand-specific probes for in situ studies for both the ATAL and TAL transcripts.
Figure 20:
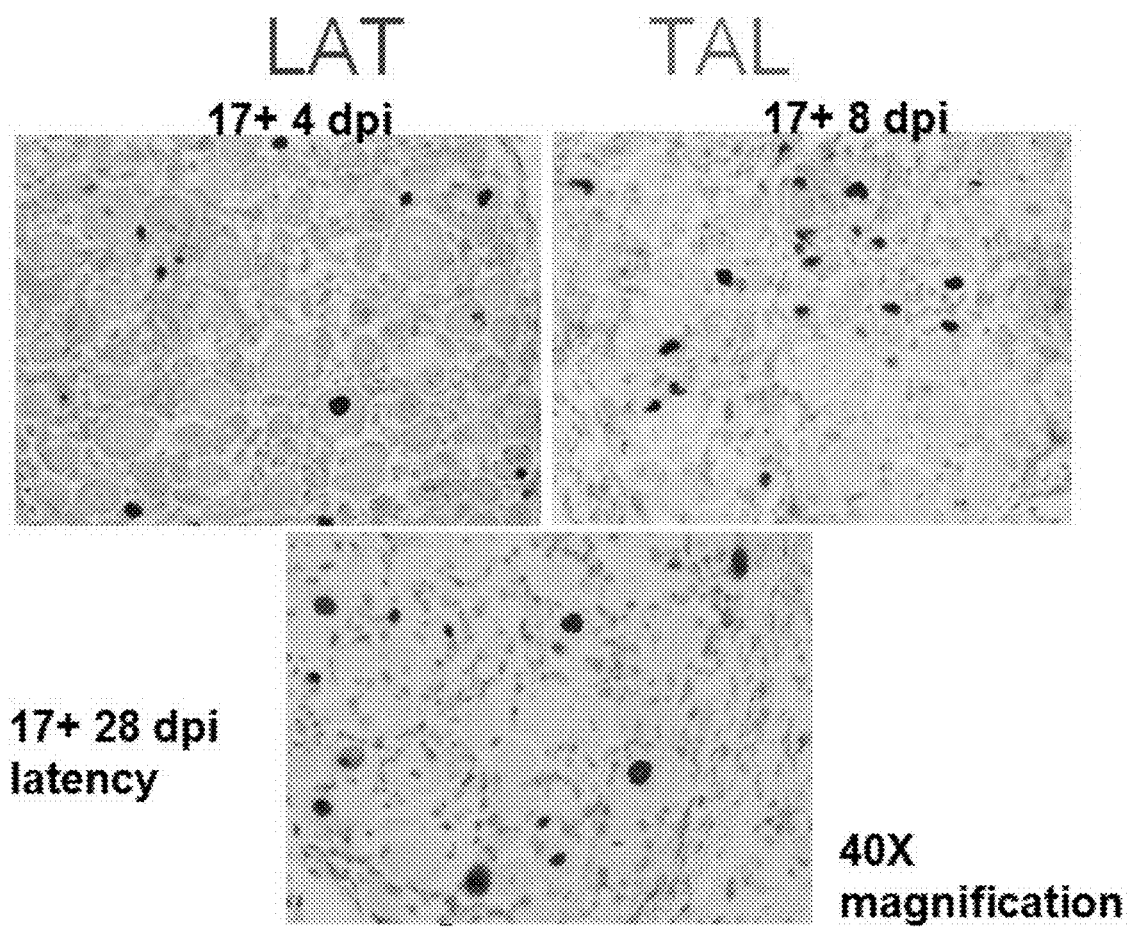
FIG. 20 shows images of LAT and TAL expression at various stages.
Figures 21, 22:
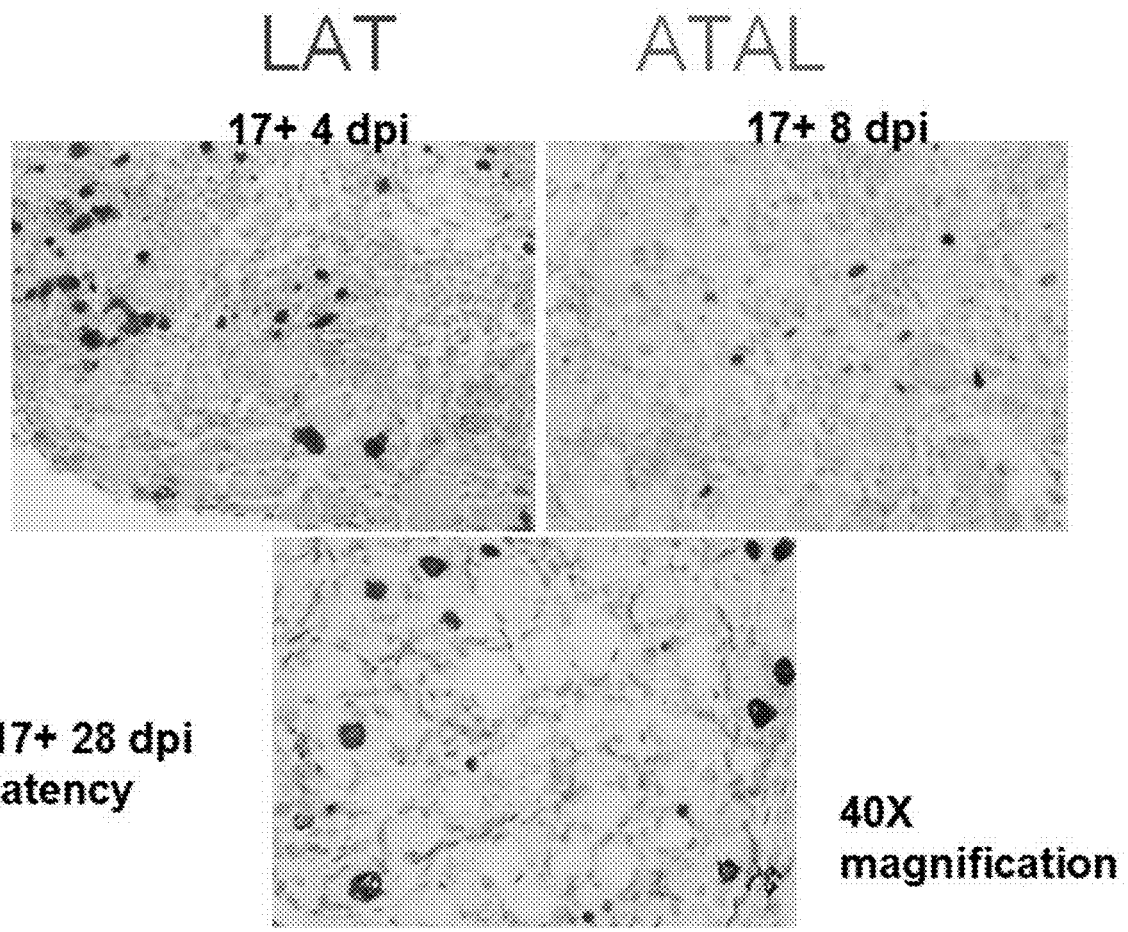
FIG. 21 shows images of LAT and ATAL expression at various stages.
FIG. 22 provides a summary of TAL/ATAL expression.
Figure 23A:
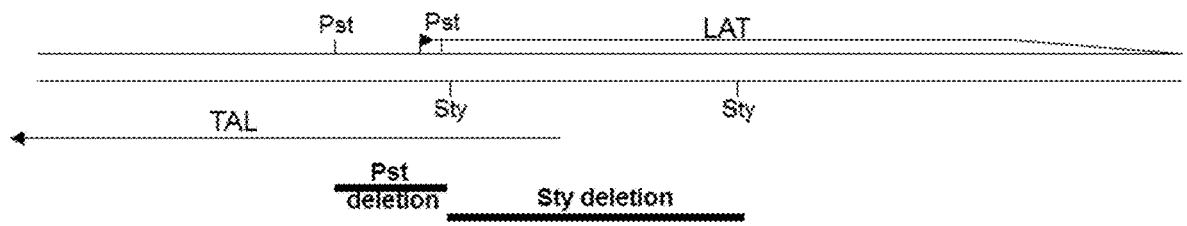
FIGS. 23A-23C show that the deletion of either the PstI-PstI fragment or the StyI-StyI fragment of the LAT region abrogates the transcript's expression. A map of the Pst and Sty deletions is shown in FIG. 23A. The relative RNA levels for the PstI deleted fragment and the relative quantity of TAL for the StyI deleted construct are shown in FIG. 23B and FIG. 23C, respectively.
Figure 23B:
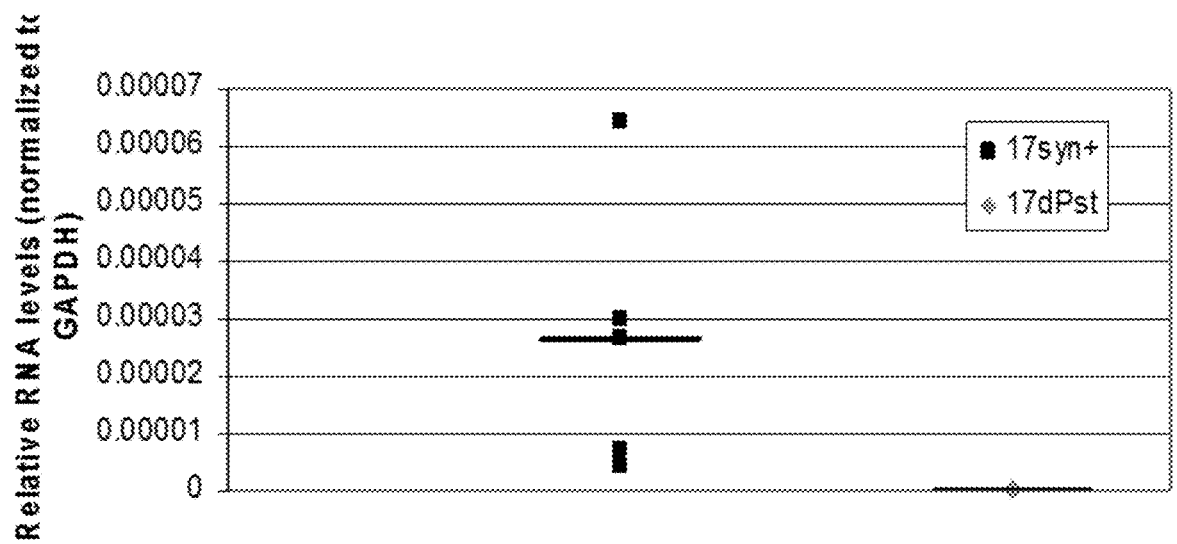
Figure 23C:
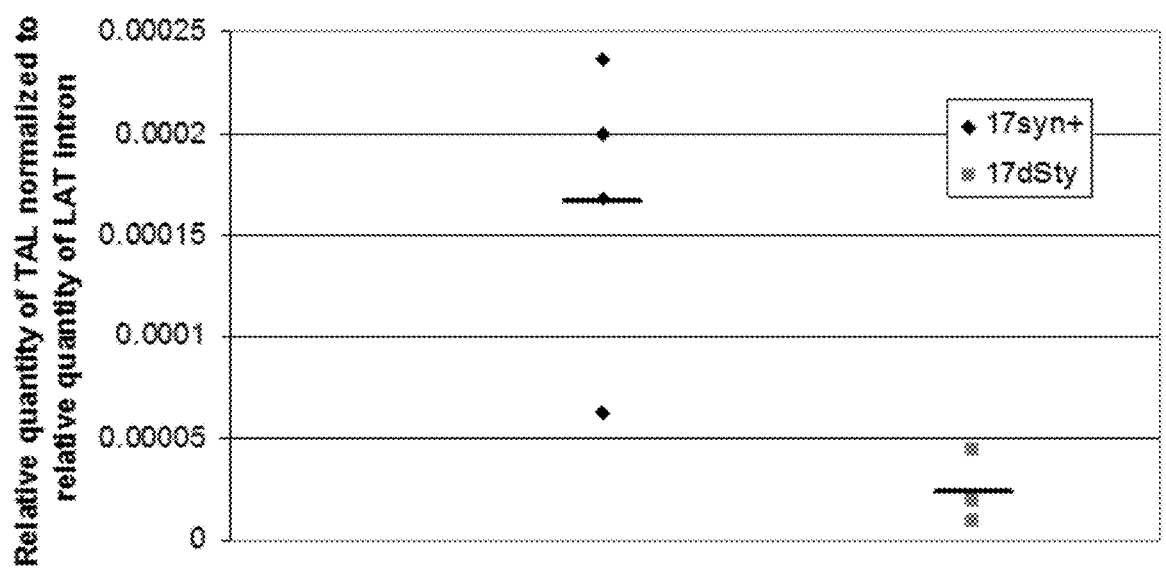

Strand-specific probes were utilized for in situ studies with both TAL and ATAL transcripts (FIG. 19). TAL and ATAL presence in cells were detected microscopically in comparison with LAT (FIG. 20 and FIG. 21, respectively). Results of the comparative evaluation of expression levels are shown in FIG. 22. It was further shown that the deletion of either the PstI-PstI fragment or the StyI-StyI fragment of the LAT region abrogates the transcript's expression. A map of the Pst and Sty deletions is shown in FIG. 23A. The relative RNA levels for the PstI deleted fragment and the relative quantity of TAL for the StyI deleted construct are depicted in FIG. 23B and FIG. 23C, respectively.

Based on the identification and characterization of TAL and ATAL described above, a number of targeting nucleic acids were designed based on various target sequences identified in these transcripts. Non-limiting examples of ribozyme sequences designed to target TAL transcript are listed in Table I. These TAL-targeting ribozymes were designed based on the corresponding target sequences listed in Table II. Several physical parameters were determined for each TAL-targeting sequence in order to evaluate ribozyme effectiveness and are listed in Table III. Non-limiting examples of ribozyme sequences designed to target ATAL transcript are listed in Table IV. These ATAL-targeting ribozymes were designed based on the corresponding target sequences listed in Table V. Several physical parameters were determined for each TAL-targeting sequence in order to evaluate ribozyme effectiveness and are listed in Table VI.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be non-limiting examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

SEQUENCE LISTING

<160> NUMBER OF SEQ ID NOS: 69

<210> SEQ ID NO 1
<211> LENGTH: 33
<212> TYPE: RNA
<213> ORGANISM: Artificial Sequence
<220> FEATURE:
<223> OTHER INFORMATION: Synthetic Polynucleotide

<400> SEQUENCE: 1
ggacacugau gagcgcuucg gcgcgaaacg aac                          33

<210> SEQ ID NO 2
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 2
guucgucugu cc                                                12

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
ggctccatcg cctttcct                                          18

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4
cgccccagag gctaagg                                           17

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
gcaccaccaa ctgcttagc                                         19

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 6
aagggaggga ggagggtact g                                      21

<210> SEQ ID NO 7
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 7
gggctggtgt gctgtaaca                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
cctccacaat gccgaagtg                                                19

<210> SEQ ID NO 9
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 9
tctcgcttct cccc                                                     14

<210> SEQ ID NO 10
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 10
ccacgccact cgcg                                                     14

<210> SEQ ID NO 11
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 11
ctggccaagg tcatcc                                                   16

<210> SEQ ID NO 12
<211> LENGTH: 662
<212> TYPE: RNA
<213> ORGANISM: Artificial Sequence
<220> FEATURE:
<223> OTHER INFORMATION: Synthetic Polynucleotide

<400> SEQUENCE: 12
gaucgcgggu ggugcgaaag acuuccggg  cgcguccggg ugccgcggcu cuccgggccc    60
cccugcagcc ggggcggcca aggggcgucg gcgacauccu ccccuaagc gccggccggc   120 cgcuggucug uuuuuucguu uuccccguuu cggggguggu ggggguugcg guuucuguuu   180
cuuuaacccg ucuggggugu uuuucguucc gucgccggaa uguuucguuc gucuguccccc  240 ucacggggcg aaggccgcgu acggcccggg acagggggcc cccgaccgcg gcguccggg   300 ccccguccgg acccgcucgc cggcacgcga cgcgaaaaag gccccccgga ggcuuuccg   360 gguucccggc ccggggccug agaugaacac ucgggguuac cgccaacggc cggccccgu   420

```
ggcggcccgg cccggggccc cggcggaccc aagggqcccc ggcccgqgqc cccacaacgq      480 cccggcgcau gcgcuguggu uuuuuuucc ucgguguucu gccgggcucc aucgccuuuc      540 cguucucgc uucucccccc cccuucuuc acccccagua cccuccuccc ucccuuccuc       600 ccccquuauc ccacucgucg agggcgcccc ggugucguuc aacaaagacg ccgcguuucc    660
ag                                                                     662

<210> SEQ ID NO 13
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 13
guucgucugu cc                                                          12

<210> SEQ ID NO 14
<211> LENGTH: 33
<212> TYPE: RNA
<213> ORGANISM: Artificial Sequence
<220> FEATURE:
<223> OTHER INFORMATION: Synthetic Polynucleotide

<400> SEQUENCE: 14
ggacacugau gagcgcuucg gcgcgaaacg aac                                   33

<210> SEQ ID NO 15
<211> LENGTH: 8346
<212> TYPE: DNA
<213> ORGANISM: Human herpesvirus 1

<400> SEQUENCE: 15
cgcgggtggt gcgaaagact ttccgggcgc gtccgggtgc cgcggctctc cgggcccccc      60
tgcagccggg gcggccaagg ggcgtcggcg acatcctccc cctaagcgcc ggccggccgc     120
tggtctgttt tttcgttttc cccgtttcgg gggtggtggg ggttgcggtt tctgtttctt     180
taacccgtct ggggtgtttt tcgttccgtc gccggaatgt ttcgttcgtc tgtcccctca     240
cggggcgaag gccgcgtacg gccgcgggacg aggggccccc gaccgcggcg gtccgggccc    300
cgtccggacc cgctcgccgg cacgcgacgc gaaaaaggcc ccccggaggc ttttccgggt     360
tcccggcccg gggcctgaga tgaacactcg gggttaccgc caacggccgg cccccgtggc    420
ggcccggccc ggggccccgg cggacccaag gggcccccggc ccggggcccc acaacggccc   480
ggcgcatgcg ctgtggtttt tttttcctcg gtgttctgcc gggctccatc gccttttcctg  540 ttctcgcttc tccccccccc cttcttcacc cccagtaccc tcctccctcc cttcctcccc    600
cgttatccca ctcgtcgagg gcgccccggt gtcgttcaac aaagacgccg cgtttccagg   660
taggttagac acctgcttct ccccaataga gggggggac ccaaacgaca gggggcgccc   720
cagaggctaa ggtcggccac gccactcgcg ggtgggctcg tgttacagca caccagcccg  780
ttcttttccc cccctcccac ccttagtcag actctgttac ttacccgtcc gaccaccaac  840 tgcccccttta tctaagggcc ggctggaaga ccgccagggg gtcggccggt gtcgctgtaa   900 cccccccacgc caatgaccca cgtactccaa gaaggcatgt gtcccacccc gcctgtgttt  960
ttgtgcctgg ctctctatgc ttgggtctta ctgcctgggg gggggagtg cgggggaggg    1020 ggggtgtgga aggaaatgca cggcgcgtgt gtaccccccc taaagttgtt cctaaagcga   1080
ggatacggag gagtggcggg tgccggggga ccggggtgat ctctggcacg cgggggtggg   1140
```

```
aagggtcggg ggaggggggg atggagtacc ggcccacctg gccgcgcggg tgcgcgtgcc    1200
tttgcacacc aacccacgt ccccggcgg tctctaagaa gcaccgcccc cctccttca       1260 taccaccgag catgcctggg tgtgggttgg taaccaacac gcccatcccc tcgtctcctg    1320
tgattctctg gctgcaccgc attcttgttt tctaactatg ttcctgtttc tgtctccccc    1380
ccccccaccc ctccgcccca cccccaaca cccacgtctg tggtgtggcc gaccccctttt   1440 tgggcgcccc gtcccgcccc gccacccctc ccatcctttg ttgccctata gtgtagttaa    1500 cccccccgc cctttgtggc ggccagaggc caggtcagtc cgggcgggca ggcgctcgcg     1560
gaaacttaac acccacaccc aacccactgt ggttctggct ccatgccagt ggcaggatgc    1620
tttcggggat cggtggtcag gcagcccggg ccgcggctct gtggttaaca ccagagcctg    1680
cccaacatgg cacccccact cccacgcacc cccactccca cgcaccccca ctcccacgca    1740 ccccactcc cacgcaccc cactcccacg cacccccact cccacgcacc cccactccca     1800
cgcaccccca ctcccacgca ccccactcc cacgcatccc cgcgatacat ccaacacaga    1860
cagggaaaag atacaaaagt aaacctttat ttcccaacag acagcaaaaa tcccctgagt   1920
ttttttttat tagggccaac acaaaagacc cgctggtgtg tggtgcccgt gtctttcact    1980
tttcccctcc ccgacacgga ttggctggtg tagtgggcgc ggccagagac cacccagcgc   2040 ccgaccccc cctccccaca aacacggggg gcgtcccctta ttgttttccc tcgtcccggg   2100
tcgacgcccc ctgctccccg gaccacgggt gccgagaccg caggctgcgg aagtccaggg   2160
cgcccactag ggtgccctgg tcgaacagca tgttccccac gggggtcatc cagaggctgt    2220
tccactccga cgcgggggcc gtcgggtact cgggggcat cacgtggtta cccgcggtct    2280
cggggagcag ggtgcggcgg ctccagccgg ggaccgcggc ccgcagccgg gtcgccatgt    2340
ttcccgtctg gtccaccagg accacgtacg cccgatgtt ccccgtctcc atgtccagga    2400
tgggcaggca gtccccgtg atagtcttgt tcacgtaagg cgacagggcg accacgctag    2460
agacccccga gatgggcagg tagcgcgtga ggccgcccgc ggggacggcc ccggaagtct    2520
ccgcgtggcg cgtcttccgg gcacacttcc tcggcccccg cggccagaa gcagcgcggg    2580 ggccgaggga ggtttcctct tgtctccctc ccagggcacc gacggccccg cccgaggagg    2640
cggaagcgga ggaggacgcg gccccggcgg cggaagaggc ggcccccgcg ggggtcgggg    2700
ccgaggagga agaggcagag gaggaagagg cggaggccgc cgaggacgtc agggggtcc    2760 cgggcccacc ctggccgcgc ccccccggcc ctgagtcgga ggggggtgc gtcgccgccc    2820 tcttggcccc tgccgcgcg aggggggac gcgtggactg ggggagggg ttttcctggc     2880 ccgacccgcg cctcttcctc ggacgcaccg ccgcctcctg ctcgacagag gcggcggagg    2940
ggagcggggc ggcgccggag ggggcggcgc cgcgggaggg cccgtgccca ccctccacgc    3000 ccggccccccc cgagccgcgc gccaccgtcg cacgcgcccg gcacagactc tgttcttggt    3060
tcgcggcctg agccagggac gagtgcgact ggggcacacg gcgcgcgtcc gcggggcggg    3120
cggccggctc cgccccgggg gccggggcgc ggggccggg cccggaggc ggcgctcgca     3180 cgcacggggc cacggccgcg cggggcgcg cgggtcccga cgcggccgcg gacgcggggg    3240
gcccggggcg gggggcggag cctggcatgg gcgccgcggg gggcctgtgg ggagaggccg   3300 gggggggagtc gctgatcact atggggtctc tgttgtttgc aagggggcg ggtctgttga    3360 caaggggcc cgtccggccc ctcggccgcc ccgcctccgc ttcaacaacc ccaaccccaa    3420
ccccaacccc cccggaggg ccagacgccc ccgcgcgcg cgcggctcgc gactggcggg      3480
```

```
agccgccgcc gccgctgctg ttggtggtgg tgttggtgtt actgctgccg tgtggcccga    3540
tgggcgccga gggggggcgct gtccgagccg cggccggctg gggggctgcg tgagacgccc    3600
cgcccgtcac gggggggcgcg gcggcgcctc tgcgtggggg ggcgcggggc gtccggcggg    3660
gggcgggcgg tacgtagtct gctgcaagag acaacggggg gcgcgatcag gttacgcccc    3720
ctccccggcc cgcccttttcc tcgcccgccc gcctattcct ccctcccccc cctcctcct    3780
cctcctcccc cagggtcctt gccgcccccc gcctcaccgt cgtccaggtc gtcgtcatcc    3840
tcgtccgtgg tgggctccgg gtgggtgggc gacagggccc tcaccgtgtg ccccccccagg    3900
gtcaggtacc gcggggcgaa ccgctgattg cccgtccaga taaagtccac ggccgtgccc    3960
gccctgacgg cctcctcggc tccatgcgg gtctgggggt cgttcacgat cgggatggtg    4020
ctgaacgacc cgctgggcgt cacgcccact atcaggtaca ccagcttggc gttgcacagc    4080
gggcaggtgt tgcgcaattg catccaggtt ttcatgcacg ggatgcagaa gcggtgcatg    4140
cacgggaagg tgtcgcagcg caggtggggc gcgatctcat ccgtgcacac ggcgcacacg    4200
tcgccctcgt cgctcccccc gtcctctcga ggggggggcgc cccgcaact gccggggtct    4260
tcctcgcggg gggggctccc ccccgagacc gccccccat ccacgccctg cggccccagc    4320
agccccgtct cgaacagttc cgtgtccgtg ctgtccgcct cggaggcgga gtcgtcgtca    4380
tggtggtcgg cgtccccccg ccccccccact tcggtctccg cctcagagtc gctgctgtcc    4440
ggcaggtctc ggtcgcaggg aaacaccag acatccgggg cgggctaagg ggaaaaaagg    4500
ggggcgggta agaatggggg gggatttccc gcgtcaatca gcacccacga gttccccctc    4560
tcccccccc gcctcacaaa gtcctgcccc cctgctggcc tcggaagagg ggggagaaag    4620
gggtctgcaa ccaaaggtgg tctgggtccg tcctttggat cccgacccct cttcttccct    4680
cttctcccgc cctccagacg caccggagtc gggggtccca cggcgtcccc caaatatggc    4740
gggcggctcc tccccacccc cctagatgcg tgtgagtaag gggggcctgc gtatgagtca    4800
gtggggacca cgccccaac acggcgaccc cggtccttgt gtgtttgttg tgggggcgtg    4860
tctctgtgta tgagtcaggg ggtcccacgg cgaccccggg ccctgcgtct gagtcaaagg    4920
ggccatgtgt atgtgttggg ggtctgtata tataaagtca gggggtcaca tggcgacccc    4980
caacagggcg accccggtcc ctgtatatat agggtcaggg ggttccgcac ccctaacat    5040
ggcgccccccg gtccctgtat atatagtgtc acggggttcc acgccccta acatggcgcc    5100
ccaacatggc gcccggctcc cgtgtatgag tgggggtccc ccaacatggc ggccggttcc    5160
agtgtaaggg tcgggggtcc cccaacatgg cgcccccaa tatggcgccc ccaatatgg    5220
cgccccagac atggcgcccg gccctcacc tcgcgctggg ggcggccctc aggccggcgg    5280
gtactcgctc cggggcgggg ctccatgggg gtcgtatgcg gctggagggt cgcggacgga    5340
gggtccctgg gggtcgcaac gtaggcgggg cttctgtggt gatgcggaga gggggcggcc    5400
cgagtctgcc tggctgctgc gtctcgctcc gagtgccgag gtgcaaatgc gaccagactg    5460
tcgggccagg gctaacttat accccacgcc tttccccctcc ccaaagggc ggcagtgacg    5520
attccccccaa tggccgcgcg tcccagggga ggcaggccca ccgcggggcg gccccgtccc    5580
cggggaccaa cccggcgccc ccaaagaata tcattagcat gcacgcccg gccccgatt    5640
tgggggccca accggtgtc ccccaaagaa ccccattagc atgcccctcc cgccgacgca    5700
acagggggctt ggcctgcgtc ggtgcccccg ggcttcccgc cttccgaag aaactcatta    5760
ccatacccgg aaccccaggg gaccaatgcg ggttcattga gcgacccgcg ggccaatgcg    5820
cgaggggccg tgtgttccgc caaaaaagca attagcataa cccggaaccc caggggagtg    5880
```

```
gttacgcgcg gcgcgggagg cggggaatac cggggttgcc cattaagggc cgcgggaatt    5940
gccggaagcg ggaagggcgg ccggggccgc ccattaatga gtttctaatt accataccgg    6000
gaagcggaac aaggcctctt gcaagttttt aattaccata ccgggaagtg ggcggcccgg    6060
cccattgggc ggtaactccc gcccaatggg ccgggccccg aagactcggc ggacgctggt    6120
tggccgggcc ccgccgcgct ggcggccgcc gattggccag tcccgccccc gaggcggccc    6180
gccctgtgag ggcgggctgg ctccaagcgt atatatgcgc ggctcctgcc atcgtctctc    6240
cggagagcgg cttggtgcgg agctcccggg agctccgcgg aagacccagg ccgcctcggg    6300
tgtaacgtta gaccgagttc gccgggccgg ctccgcgggc cagggcccgg gcacgggcct    6360
cgggccccag gcacggcccg atgaccgcct cggcctccgc cacccggcgc cggaaccgag    6420
cccggtcggc ccgctcgcgg gcccacgagc gcggcgcgc caggcgggcg gccgaggccc    6480
agaccaccag gtggcgcacc cggacgtggg gcgagaagcg caccgcgcg ggggtcgcgg    6540
gggtcgcggg ggtcgcgggg gtcgcggggg tcgcggggg ctccggcgcc ccctccccgc    6600
ccgcgcgtcg caggcgcagg cgcgccaggt gctccgcggt gacgcgcagg cggagggcga    6660
ggcgcggcgg aaggcggaag gggcgcgagg ggggtggga ggggtcagcc ccgccccccg    6720
ggcccacgcc gggcggtggg ggccggggcc gggggcggc ggcggtgggc cgggcctctg    6780
gcgccggctc gggcgggggg ctgtccggcc agtcgtcgtc atcgtcgtcg tcggacgcgg    6840
actcgggaac gtggagccac tggcgcagca gcagcgaaca agaaggcggg ggcccaccgg    6900
cggggggcgg cggcggggcg gccgcgggcg cgctcctgac cgcgggttcc gagttgggcg    6960
tggaggttac ctgggactgt gcggttggga cggcgcccgt gggcccgggc ggccggggc    7020
ggcggggcc gcgatggcgg cggcggcggg ccatggagac agagagcgtg ccggggtggt    7080
agagtttgac aggcaagcat gtgcgtgcag aggcgagtag tgcttgcctg tctaactcgc    7140
tagtctcggc cgcggggggc ccgggctgcc cgccgccacc gctttaaagg gccgcgcgcg    7200
accccgggg ggtgtgtttt ggggggggcc cgttttcggc gtctggccgc tcctcccccc    7260
gctcctcccc ccgctcctcc ccccgctcct cccccgctc ctccccccgc tcctcccccc    7320
gctcctcccc ccgctcctcc ccccgctcct cccccgctc ctccccccgc tcctcccccc    7380
gctcctcccc ccgctcctcc ccccgctcct cccccgctc ctccccccgc tcctcccccc    7440
gctcctcccc ccgctcctcc ccccgctccc gggccccgc ccccacgcc cgccgcgcg    7500
gcgcacgccg cccggaccgc cgcccgcctt ttttgcgcgc gcgcgcgccc gcggggggcc    7560
cgggctgcca caggtgaaac caacagagca cggcgcactc cgcacgtcac acgtcacgtc    7620
atccaccaca cctgcccaac aacacaactc acagcgacaa ctcaccgcgc aacaactcct    7680
gttcctcatc cacacgtcac cgcgcacctc ccgtcctcc agacgtaccc cggcgcaaca    7740
caccgctcct gctacacacc accgcccccct cccccagcccc agccctcccc agcccccagcc    7800
ctccccggcc ccagccctcc ccggcccag ccctccccgg cccagccct ccccggcccc    7860
agccctcccc ggccccagcc ctccccgcc ccagccctcc ccggcgcgtc ccgcgctccc    7920
tcgggggggt cgggcatct ctacctcagt gccgccaatc tcaggtcaga gatccaaacc    7980
ctccggggc gccgcgcac caccaccgcc cctcgccccc tcccgccccct cgccccctcc    8040
cgccccctcgc ccctcccgcc cctcgccccc ctcccgcccc tcgccccctc ccgcccctcg    8100
cccccctcccg ccctcgccc cctcccgccc ctcgccccct cccgccccctc gccccctccc    8160
gccccctcgcc ccctcccgcc ccctcgcccc ctcccgcccc tcgccccctcc cgccccctcgc    8220
```

| | |
|---|---|
| ccccteccge ccctcgcccc ctcccgcccc tcgcccccte ccgcccctcg ccccctcccg | 8280 |
| ccccctcgccc cctcccgccc ctcgcccccct cccgcccctc gccccctccc gccccctcgaa | 8340 |
| taaaca | 8346 |

<210> SEQ ID NO 16
<211> LENGTH: 1701
<212> TYPE: DNA
<213> ORGANISM: Human herpesvirus 1

<400> SEQUENCE: 16

| | |
|---|---|
| tgaggggaca gacgaacgaa acattccggc gacggaacga aaacaccccc agacgggtta | 60 |
| aagaaacaga aaccgcaacc cccaccaccc ccgaaacggg gaaaacgaaa aaacagacca | 120 |
| gcggccggcc ggcgcttagg gggaggatgt cgccgacgcc ccttggccgc cccggctgca | 180 |
| ggggggcccg gagagccgcg gcacccggac gcgcccggaa agtctttcgc accacccgcg | 240 |
| atcggcacgg ccgcgccccc gcttttataa aggctgagat gacgcagcaa aaacaggcca | 300 |
| cagcaccacg tgggtaggtg atgtaatttt attttcctcg tctgcggcct aatggatttc | 360 |
| cgggcgcggt gcccctgtct gcagagcact taacggattg atatctcgcg ggcacgcgcg | 420 |
| cccttaatgg accggcgcgg ggcggggggc cggatacccca cacgggcggg ggggggtgt | 480 |
| cgcgggccgt ctgctggccc gcggccacat aaacaatgac tctgggcctt tctgcctctg | 540 |
| ccgcttgtga gtgcgcgcgc cggctctgcg gtgtcggcgg cggctgcggc ggctgcggcg | 600 |
| gccgccgtgt tcggtctcgg tagccggccg gcgggtggac tcgcgggggg ccggagggtg | 660 |
| gaaggcaggg gggtgtagga tgggtatcag gacttccact tcccgtcctt ccatccccg | 720 |
| ttcccctcgg ttgttcctcg cctcccccaa caccccgccg cttccgttg gggttgttat | 780 |
| tgttgtcgga atcgtgcggg ccgggggtcg cggggcagg ggcgggggcg tgggcggggg | 840 |
| tgctcgtcga tcgaccgggc tcagtggggg cgtggggtgg gtgggagaag gcgaggagac | 900 |
| tggggtgggg gtgtcggtgg gtggttgttt tttgtggttg tttttgtgtc tgttcccgtc | 960 |
| ccccgtcacc ccctccctcc gtccctccg tccccccgtc gcgggtgttt gtgtttgttt | 1020 |
| attccgacat tggtttattt aaataaacac agccgttctg cgtgtctgtt cttgcgtgtg | 1080 |
| gctgggggct tatatgtggg gtcccgggg cgggatgggg tttagcggcg gggggcggcg | 1140 |
| cgccggacgg ggcgctggag ataacggccc ccggggaacg ggggaccggg gctgggtatc | 1200 |
| ccgaggtggg tgggtgggcg gcggtggccg ggccggccg ggccgggccg ggccgggtgg | 1260 |
| gcggggtttg gaaaaacgag gaggaggagg agaaggcggg ggggggggag acggggggaa | 1320 |
| agcaaggaca cggcccgggg ggtgggagcg cgggccgggc cgctcgtaag agccgcgacc | 1380 |
| cggccgccgg ggagcgttgt cgccgtcggt ctgccggccc ccgtccctcc ctttttgac | 1440 |
| caaccagcgc ccccccccc tcaccaccat tcctactacc accaccacca ccaccaccga | 1500 |
| cacctcccgc gcaccccgc ccacatcccc cccaacccg caccaccagc acgggttggg | 1560 |
| ggtagcaggg gatcaaaggg gggcaaagcc ggcggggcgg ttcgggggg ggggggggg | 1620 |
| gcgggaaacc aagtaggccc gcccatccgc ggcccctccc ggcagccacg cccccagcgt | 1680 |
| cgggtgtcac ggggaaagag c | 1701 |

<210> SEQ ID NO 17
<211> LENGTH: 1311
<212> TYPE: DNA
<213> ORGANISM: Human herpesvirus 1

<400> SEQUENCE: 17

```
tgggcgggcc tacttggttt cccgcccccc cccccccccc ccgaaccgcc ccgccggctt    60 tgccccccctt tgatcccctg ctaccccccaa cccgtgctgg tggtgcgggt tggggggggga  120 tgtgggcggg ggtgcgcggg aggtgtcggt ggtggtggtg gtggtggtag taggaatggt   180
ggtgaggggg gggggcgct ggttggtcaa aaaagggagg gacgggggcc ggcagaccga    240
cggcgacaac gctccccggc ggccgggtcg cggctcttac gagcggcccg gcccgcgctc   300 ccacccccccg gccgtgtcc ttgctttccc ccgtctccc ccccccccgc cttcctctcc    360
tcctcctcgt ttttccaaac cccgcccacc cggcccggcc cggcccggcc cggcccggcc   420
accgccgccc acccacccac ctcgggatac ccagccccgg tccccgcgttc cccggggggcc  480 gttatctcca gcgccccgtc cggcgcgccg ccccccgccg ctaaaccccca tcccgccccc  540 gggaccccac atataagccc ccagccacac gcaagaacag acacgcagaa cggctgtgtt   600
tatttaaata aaccaatgtc ggaataaaca aacacaaaca cccgcgacgg ggggacggag   660
gggacggagg gaggggggtga cggggggacgg gaacagacac aaaaacaacc acaaaaaaca  720
accacccacc gacacccccca ccccagtctc ctcgccttct cccacccacc ccacgccccc   780
actgagcccg gtcgatcgac gagcacccccc gcccacgccc ccgcccctgc cccggcgacc   840
cccggcccgc acgatcccga caacaataac aaccccaacg gaaagcggcg gggtgttggg    900
ggaggcgagg aacaaccgag gggaacgggg gatggaagga cgggaagtgg aagtcctgat   960
acccatccta caccccccctg ccttccaccc tccggccccc cgcgagtcca cccgccggcc  1020
ggctaccgag accgaacacg gcggccgccg cagccgccgc agccgccgcc gacaccgcag  1080
agccggcgcg cgcactcaca agcggcagag gcagaaaggc ccagagtcat tgtttatgtg  1140
gccgcgggcc agcagacggc ccgcgacacc cccccccgc ccgtgtgggt atccggcccc  1200
ccgccccgcg ccggtccatt aagggcgcgc gtgcccgcga gatatcaatc cgttaagtgc  1260
tctgcagaca ggggcaccgc gcccggaaat ccattaggcc gcagacgagg a           1311
```

<210> SEQ ID NO 18
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 18
uguuucuucu gaugaggccg aaaggccgaa aacccg                               36

<210> SEQ ID NO 19
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 19
cuguuucuuc ugaugaggcc gaaaggccga aacccgu                              38

<210> SEQ ID NO 20
<211> LENGTH: 34
<212> TYPE: RNA
<213> ORGANISM: Artificial Sequence
<220> FEATURE:
<223> OTHER INFORMATION: Synthetic Polynucleotide

<400> SEQUENCE: 20

```
ugcgacugau gaggccgaaa ggccgaaaga cuuu              34

<210> SEQ ID NO 21
<211> LENGTH: 39
<212> TYPE: RNA
<213> ORGANISM: Artificial Sequence
<220> FEATURE:
<223> OTHER INFORMATION: Synthetic Polynucleotide

<400> SEQUENCE: 21
ggaaaauaac ugaugaggcc gaaaggccga aauuacauc         39

<210> SEQ ID NO 22
<211> LENGTH: 39
<212> TYPE: RNA
<213> ORGANISM: Artificial Sequence
<220> FEATURE:
<223> OTHER INFORMATION: Synthetic Polynucleotide

<400> SEQUENCE: 22
aggaaaaucu gaugaggccg aaaggccgaa aaauuacau         39

<210> SEQ ID NO 23
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 23
aggaaaacug augaggccga aaggccgaaa aaauuaca          38

<210> SEQ ID NO 24
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 24
gaggaacuga ugaggccgaa aggccgaaau aaaauuac          38

<210> SEQ ID NO 25
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 25
gagauauccu gaugaggccg aaaggccgaa auccguua          38

<210> SEQ ID NO 26
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 26
aaguccucug augaggccga aaggccgaaa uaccca            36

<210> SEQ ID NO 27
<211> LENGTH: 38
<212> TYPE: RNA
<213> ORGANISM: Artificial Sequence
```

```
<220> FEATURE:
<223> OTHER INFORMATION: Synthetic Polynucleotide

<400> SEQUENCE: 27
gacaacaauc ugaugaggcc gaaaggccga aacaaccc                              38

<210> SEQ ID NO 28
<211> LENGTH: 37
<212> TYPE: RNA
<213> ORGANISM: Artificial Sequence
<220> FEATURE:
<223> OTHER INFORMATION: Synthetic Polynucleotide

<400> SEQUENCE: 28
cccgaccuga ugaggccgaa aggccgaaac aauaaca                               37

<210> SEQ ID NO 29
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 29
caagaacacu gaugaggccg aaaggccgaa acacgc                                36

<210> SEQ ID NO 30
<211> LENGTH: 15
<212> TYPE: RNA
<213> ORGANISM: Artificial Sequence
<220> FEATURE:
<223> OTHER INFORMATION: Synthetic Polynucleotide

<400> SEQUENCE: 30
cggguuaaag aaaca                                                       15

<210> SEQ ID NO 31
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 31
acggguuaaa gaaacag                                                     17

<210> SEQ ID NO 32
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 32
aaagucuuuc gca                                                         13

<210> SEQ ID NO 33
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 33
gauguaauuu uauuuucc                                                    18
```

```
<210> SEQ ID NO 34
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 34
auguaauuuu auuuuccu                                                 18

<210> SEQ ID NO 35
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 35
uguaauuuua uuuuccu                                                  17

<210> SEQ ID NO 36
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 36
guaauuuuau uuccuc                                                   17

<210> SEQ ID NO 37
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 37
uaacggauug auaucuc                                                  17

<210> SEQ ID NO 38
<211> LENGTH: 15
<212> TYPE: RNA
<213> ORGANISM: Artificial Sequence
<220> FEATURE:
<223> OTHER INFORMATION: Synthetic Polynucleotide

<400> SEQUENCE: 38
uggguaucag gacuu                                                    15

<210> SEQ ID NO 39
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 39
gggUuguuau uguuguc                                                  17

<210> SEQ ID NO 40
<211> LENGTH: 16
<212> TYPE: RNA
<213> ORGANISM: Artificial Sequence
<220> FEATURE:
<223> OTHER INFORMATION: Synthetic Polynucleotide
```

```
<400> SEQUENCE: 40
uguuauuguu gucggg                                                    16

<210> SEQ ID NO 41
<211> LENGTH: 15
<212> TYPE: RNA
<213> ORGANISM: Artificial Sequence
<220> FEATURE:
<223> OTHER INFORMATION: Synthetic Polynucleotide

<400> SEQUENCE: 41
gcgugucugu ucuug                                                     15

<210> SEQ ID NO 42
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 42
cccuuuuuuc ugaugaggcc gaaaggccga aaccaacc                            38

<210> SEQ ID NO 43
<211> LENGTH: 34
<212> TYPE: RNA
<213> ORGANISM: Artificial Sequence
<220> FEATURE:
<223> OTHER INFORMATION: Synthetic Polynucleotide

<400> SEQUENCE: 43
ugggacugau gaggccgaaa ggccgaaaag gcga                                34

<210> SEQ ID NO 44
<211> LENGTH: 37
<212> TYPE: RNA
<213> ORGANISM: Artificial Sequence
<220> FEATURE:
<223> OTHER INFORMATION: Synthetic Polynucleotide

<400> SEQUENCE: 44
auaaacaauc ugaugaggcc gaaaggccga aacucug                             37

<210> SEQ ID NO 45
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 45
cacauaaacc ugaugaggcc gaaaggccga aaugacuc                            38

<210> SEQ ID NO 46
<211> LENGTH: 41
<212> TYPE: RNA
<213> ORGANISM: Artificial Sequence
<220> FEATURE:
<223> OTHER INFORMATION: Synthetic Polynucleotide

<400> SEQUENCE: 46
cacuuaacgc ugaugaggcc gaaaggccga aauugauauc u                        41

<210> SEQ ID NO 47
```

```
<211> LENGTH: 37
<212> TYPE: RNA
<213> ORGANISM: Artificial Sequence
<220> FEATURE:
<223> OTHER INFORMATION: Synthetic Polynucleotide

<400> SEQUENCE: 47
guaggucuga ugaggccgaa aggccgaaau guaauuu                              37

<210> SEQ ID NO 48
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 48
guaggucuga ugaggccgaa aggccgaaau guaauuuu                             38

<210> SEQ ID NO 49
<211> LENGTH: 41
<212> TYPE: RNA
<213> ORGANISM: Artificial Sequence
<220> FEATURE:
<223> OTHER INFORMATION: Synthetic Polynucleotide

<400> SEQUENCE: 49
gguaggucug augaggccga aaggccgaaa uguaauuuua u                         41

<210> SEQ ID NO 50
<211> LENGTH: 42
<212> TYPE: RNA
<213> ORGANISM: Artificial Sequence
<220> FEATURE:
<223> OTHER INFORMATION: Synthetic Polynucleotide

<400> SEQUENCE: 50
gguaggucug augaggccga aaggccgaaa uguaauuuua uu                        42

<210> SEQ ID NO 51
<211> LENGTH: 33
<212> TYPE: RNA
<213> ORGANISM: Artificial Sequence
<220> FEATURE:
<223> OTHER INFORMATION: Synthetic Polynucleotide

<400> SEQUENCE: 51
ugagaucuga ugaggccgaa aggccgaaac gca                                  33

<210> SEQ ID NO 52
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 52
aaaggcucug augaggccga aaggccgaaa gaugac                               36

<210> SEQ ID NO 53
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 53
```

```
gacagaccug augaggccga aaggccgaaa acgaaaca                              38

<210> SEQ ID NO 54
<211> LENGTH: 33
<212> TYPE: RNA
<213> ORGANISM: Artificial Sequence
<220> FEATURE:
<223> OTHER INFORMATION: Synthetic Polynucleotide

<400> SEQUENCE: 54
ggacacugau gaggccgaaa ggccgaaacg aac                                   33

<210> SEQ ID NO 55
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 55
gguuggucaa aaaaggg                                                     17

<210> SEQ ID NO 56
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 56
ucgccuucuc ccac                                                        14

<210> SEQ ID NO 57
<211> LENGTH: 16
<212> TYPE: RNA
<213> ORGANISM: Artificial Sequence
<220> FEATURE:
<223> OTHER INFORMATION: Synthetic Polynucleotide

<400> SEQUENCE: 57
cagagucauu guuuau                                                      16

<210> SEQ ID NO 58
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 58
gagucauugu uuaugug                                                     17

<210> SEQ ID NO 59
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 59
agauaucaau ccguuaagug                                                  20

<210> SEQ ID NO 60
<211> LENGTH: 16
<212> TYPE: RNA
```

```
<213> ORGANISM: Artificial Sequence
<220> FEATURE:
<223> OTHER INFORMATION: Synthetic Polynucleotide

<400> SEQUENCE: 60
aaauuacauc accuac                                                   16

<210> SEQ ID NO 61
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 61
aaaauuacau caccuac                                                  17

<210> SEQ ID NO 62
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 62
auaaaauuac aucaccuacc                                               20

<210> SEQ ID NO 63
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 63
aauaaaauua caucaccuac c                                             21

<210> SEQ ID NO 64
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 64
ugcgucaucu ca                                                       12

<210> SEQ ID NO 65
<211> LENGTH: 15
<212> TYPE: RNA
<213> ORGANISM: Artificial Sequence
<220> FEATURE:
<223> OTHER INFORMATION: Synthetic Polynucleotide

<400> SEQUENCE: 65
gucaucucag ccuuu                                                    15

<210> SEQ ID NO 66
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 66
uguuucguuc gucuguc                                                  17
```

```
<210> SEQ ID NO 67
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 67
guucgucugu cc                                                         12

<210> SEQ ID NO 68
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 68
tgatgccaca tacggaaagc                                                 20

<210> SEQ ID NO 69
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 69
aaaagcactg cacgccatag                                                 20
```

What is claimed is:

1. A method comprising administering a recombinant viral vector to a subject having a neurotropic virus infection, wherein the vector comprises a nucleic acid encoding a ribozyme that specifically binds and/or cleaves a latency-associated region transcript of a neurotropic virus, wherein the latency-associated region transcript comprises a TAL transcript, and wherein the ribozyme comprises any one of the nucleic acid sequences of SEQ ID NOs: 18, 19, 20, 21, 22, 23, 24, 25, 26, 27, 28, and 29.

2. A method comprising administering a recombinant viral vector to a subject having a neurotropic virus infection, wherein the vector comprises a nucleic acid encoding a ribozyme that specifically binds and/or cleaves a latency-associated region transcript of a neurotropic virus, wherein the latency-associated region transcript comprises an ATAL transcript, and wherein the ribozyme comprises any one of the nucleic acid sequences of SEQ ID NOs: 42, 43, 44, 45, 46, 47, 48, 49, 50, 51, 52, 53, and 54.

3. The method of claim 1, wherein the neurotropic virus is herpes virus.

4. The method of claim 1, wherein the neurotropic virus is selected from the group consisting of herpes simplex virus-1 (HHV-1), herpes simplex virus-2 (HHV-2), Varicella zoster virus (HHV-3), Epstein-Barr virus (HHV-4), Cytomegalovirus (HHV-5), Roseolovirus (HHV-6), HHV-7, and Kaposi's sarcoma-associated herpesvirus (HHV-8).

5. The method of claim 1, wherein the subject is a human subject.

6. The method of claim 1, wherein the viral vector is a single-stranded AAV (ssAAV) or a self-complementary AAV (scAAV).

7. The method of claim 1, wherein the viral vector is encapsidated by an AAV capsid.

8. The method of claim 7, wherein the AAV capsid is an AAV1, AAV5, AAV7, or AAV8 capsid, AAV8(Y733F) capsid, or a modified variant thereof.

9. The method of claim 2, wherein the neurotropic virus is herpes virus.

10. The method of claim 2, wherein the neurotropic virus is selected from the group consisting of herpes simplex virus-1 (HHV-1), herpes simplex virus-2 (HHV-2), Varicella zoster virus (HHV-3), Epstein-Barr virus (HHV-4), Cytomegalovirus (HHV-5), Roseolovirus (HHV-6), HHV-7, and Kaposi's sarcoma-associated herpesvirus (HHV-8).

11. The method of claim 2, wherein the subject is a human subject.

12. The method of claim 2, wherein the viral vector is a single-stranded AAV (ssAAV) or a self-complementary AAV (scAAV).

13. The method of claim 2, wherein the viral vector is encapsidated by an AAV capsid.

14. The method of claim 13, wherein the AAV capsid is an AAV1, AAV5, AAV7, or AAV8 capsid, AAV8(Y733F) capsid, or a modified variant thereof.

* * * * *